(12) United States Patent
Bradner et al.

(10) Patent No.: US 12,129,248 B2
(45) Date of Patent: Oct. 29, 2024

(54) CHROMOBOX PROTEIN INHIBITORS AND USES THEREOF

(71) Applicant: Dana-Farber Cancer Institute, Inc., Boston, MA (US)

(72) Inventors: James Bradner, Weston, MA (US); Jun Qi, Sharon, MA (US); Alexander Federation, Seattle, WA (US); Zoe Jacobson, Boston, MA (US); Anthony Varca, Wethersfield, CT (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/335,951

(22) PCT Filed: Sep. 25, 2017

(86) PCT No.: PCT/US2017/053229
§ 371 (c)(1),
(2) Date: Mar. 22, 2019

(87) PCT Pub. No.: WO2018/058029
PCT Pub. Date: Mar. 29, 2018

(65) Prior Publication Data
US 2020/0024267 A1    Jan. 23, 2020

Related U.S. Application Data

(60) Provisional application No. 62/399,857, filed on Sep. 26, 2016.

(51) Int. Cl.
| | |
|---|---|
| C07D 417/12 | (2006.01) |
| A61P 35/00 | (2006.01) |
| C07D 277/54 | (2006.01) |
| C07D 405/04 | (2006.01) |
| C07D 417/14 | (2006.01) |
| C07D 471/04 | (2006.01) |

(52) U.S. Cl.
CPC ............ *C07D 417/12* (2013.01); *A61P 35/00* (2018.01); *C07D 277/54* (2013.01); *C07D 405/04* (2013.01); *C07D 417/14* (2013.01); *C07D 471/04* (2013.01)

(58) Field of Classification Search
CPC .. C07D 405/04; C07D 417/12; C07D 417/14; C07D 471/04; C07D 277/54
See application file for complete search history.

(56) References Cited

U.S. PATENT DOCUMENTS

| | | |
|---|---|---|
| 5,645,988 A | 7/1997 | Vande Woude et al. |
| 8,846,320 B2 | 9/2014 | Kosmeder et al. |
| 2007/0099970 A1 | 5/2007 | Mackerell et al. |
| 2009/0088420 A1 | 4/2009 | Neamati et al. |
| 2009/0163545 A1 | 6/2009 | Goldfarb |
| 2014/0356322 A1 | 12/2014 | Crews et al. |
| 2016/0130261 A1 | 5/2016 | Burgess et al. |

FOREIGN PATENT DOCUMENTS

| | | | |
|---|---|---|---|
| EP | 2325181 A1 | 5/2011 | |
| WO | WO-1998/057931 A2 | 12/1998 | |
| WO | WO-2006/044826 A2 | 4/2006 | |
| WO | WO 2006/094237 * | 8/2006 | ........... C07D 401/12 |
| WO | WO-2007/062399 A2 | 5/2007 | |
| WO | WO-2008/090327 A1 | 7/2008 | |
| WO | WO-2008/154207 A1 | 12/2008 | |
| WO | WO-2009/089277 A2 | 7/2009 | |
| WO | WO-2010/004761 A1 | 1/2010 | |
| WO | WO-2010/039538 A2 | 4/2010 | |
| WO | WO-2010/151799 A2 | 12/2010 | |
| WO | WO-2011/094708 A2 | 8/2011 | |
| WO | WO-2012/122370 A2 | 9/2012 | |
| WO | WO-2013/059944 A1 | 5/2013 | |
| WO | WO-2013/074059 A2 | 5/2013 | |
| WO | WO-2014/062811 A2 | 4/2014 | |
| WO | WO-2014/113467 A1 | 7/2014 | |
| WO | WO-2014/147611 A1 | 9/2014 | |
| WO | WO-2016/004035 A1 | 1/2016 | |
| WO | WO-2016/077632 A2 | 5/2016 | |

OTHER PUBLICATIONS

Registry No. 296244-19-4, File Registry on STN, Oct. 17, 2000.*
Registry No. 730948-00-2, File Registry on STN, Aug. 23, 2004.*
Registry No. 1624164-86-8, File Registry on STN, Sep. 22, 2014.*
Registry No. 1061510-34-6, File Registry on STN, Oct. 15, 2008.*
Registry No. 400011-90-7, File Registry on STN, Mar. 11, 2002.*
Registry No. 399577-48-1, File Registry on STN, Mar. 8, 2002.*
Registry No. 1279912-36-5, File Registry on STN, Apr. 14, 2011.*
Registry No. 1278080-53-7, File Registry on STN, Apr. 10, 2011.*
Registry No. 1378176-70-5, File Registry on STN, Jun. 14, 2012.*
Podvinec et al., "Novel inhibitors of dengue virus methyltransferase discovery by in vitro-driven virtual screening on a desktop computer grid," Journal of Medicinal Chemistry, 53(4):1483-1495 (2010).
Supplemental European Search Report for EP Application No. 17854068.8 dated Apr. 1, 2020.
Extended European Search Report for EP Application No. 17854068.8 mailed Jul. 3, 2020.
International Search Report and Written Opinion for International Application No. PCT/US17/53229 dated Jan. 29, 2018.
Spinks et al., "Investigation of trypanothione reductase as a drug target in Trypanosoma brucei," ChemMedChem, 4(12): 2060-2069 (2009).
Abd El-Aal, H. A. K. et al., "Efficient synthesis, characterization and biological evaluation of some new atophan carbohydrazide derivatives," Journal of Chemical and Pharmaceutical Research 6: pp. 90-99 (2014).

(Continued)

*Primary Examiner* — Rebecca L Anderson
(74) *Attorney, Agent, or Firm* — Foley Hoag LLP; DeAnn F. Smith; Lucas P. Watkins

(57) ABSTRACT

Provided herein are compounds useful as inhibitors of CBX. Also described are pharmaceutical compositions and medical uses of these compounds.

10 Claims, 21 Drawing Sheets

(56) References Cited

OTHER PUBLICATIONS

Belen'kaya, R. S. et al., "Synthesis of nitrogenous derivatives of 2-phenyl- and 1-(2,2'-dithienyl-5-yl)cinchoninic acid," Khimiko-Farmatsevticheskii Zhurnal 8: pp. 19-23 (1974).
Dahal, U. P. et al., "Small Molecule Quantification by Liquid Chromatography-Mass Spectrometry for Metabolites of Drugs and Drug Candidates," Drug Metabolism and Disposition 39: pp. 2355-2360 (2011).
Registry No. 1625513-10-1, File Registry on STN, Sep. 24, 2014.
Matsuno et al., "Identification of a new series of STAT3 inhibitors by virtual screening," ACS Medicinal Chemistry Letters, 1(8):371-375 (2010).
Balasubramaniyan et al., "Reactions of cyclic anhydrides. Part XIX. Heterocyclisation of maleic anhydride derivatives with thiourea: Synthesis of 5-substituted-2-imino-4-oxo-1,3-thiazolidines", Indian Journal of Chemistry, Section B: Organic Chemistry Including Medicinal Chemistry, vol. 29B (12): pp. 1092-1096 (1990).
Extended European Search Report for EP Application No. 23182319.6 dated Dec. 18, 2023.
Havrylyuk et al., "Synthesis and anticancer activity of novel nonfused bicyclic thiazolidinone derivatives", *Phosphorus, Sulfur, and Silicon* 184(3): 638-650 (2009).
Dahal et al., "Comparative Study of the Affinity and Metabolism of Type I and Type II Binding Quinoline Carboxamide Analogues by Cytochrome P450 3A4", Journal of Medicinal Chemistry, 55(1), pp. 280-290, 2012.
Metwally et al., "Hydrazones of 2-aryl-quinoline-4-carboxylic acid hydrazides: Synthesis and preliminary evaluation as antimicrobial agents", Bioorganic & Medicinal Chemistry, 14(24), pp. 8675-8682, Dec. 15, 2006.
Peng et al., "Cytochrome P450 2C9 Type II Binding Studies on Quinoline-4-Carboxamide Analogues", J. Med. Chem., 51, pp. 8000-8011, 2008.

* cited by examiner

CHROMOBOX PROTEIN INHIBITORS AND USES THEREOF

RELATED APPLICATIONS

This application is the U.S. National Stage of International Patent Application No. PCT/US2017/053229, filed Sep. 25, 2017, which claims the benefit of priority to U.S. Provisional Patent Application Ser. No. 62/399,857, filed Sep. 26, 2016, the contents of each of which are hereby incorporated herein by reference in their entirety.

GOVERNMENT SUPPORT

This invention was made with government support under grant number R21 CA179159 awarded by The National Institutes of Health. The government has certain rights in the invention.

BACKGROUND

The polycomb complexes have been shown to be important for the maintenance of cellular identity and play important roles in stem cell differentiation. Two canonical polycomb complexes have been described in mammalian cells, polycomb repressive complex 1 and 2 (PRC1 and PRC2). The catalytic component of PRC2 is the Enhancer of Zeste Homologue 2 (EZH2), which mediates trimethylation of H3K27me3. This mark is considered a repressive histone modification and is usually found at the promoters of developmental genes in adult organisms. H3K27me3 at promoters serves as a docking site for chromobox (CBX) proteins, which all contain a conserved chromodomain responsible for binding to the methylated lysine. CBX proteins are one component of PRC1 and recruit the complex to its target genes. Two other PRC1 subunits, RING1b and BMI1, coordinate to catalyze ubiquitination of lysine 119 of histone 2A, which contributes to gene silencing. Levels of H3K27me3 are found to be deregulated in many cancers, with the repressive mark occupying tumor suppressor genes, allowing the cancerous cells to escape cell cycle checkpoints and continue uncontrolled growth. Numerous examples exist in cancer biology where hyperactivity of the polycomb complex has been linked to the pathogenesis of cancer.

Overexpression of EZH2, resulting in high global levels of H3K27me3, is observed in metastatic breast and prostate cancer and has been implicated in the development of oral squamous carcinoma and colorectal cancer. BMI1 is elevated in squamous cell carcinomas, neuroblastoma, and bladder tumors; furthermore, several studies describe its deregulation in leukemia. Mutations of EZH2 that increase catalytic activity on H3K27me2 toward elaboration of high levels of H3K27me3 have been observed in non-Hodgkin's lymphoma, and render these cancers sensitive to EZH2 inhibition. Additionally, inactivating mutations of UTX, one of two validated H3K27me3 demethylases, have been observed in numerous solid and hematologic malignancies, lending further evidence for the oncogenic activity of PRC2.

Interestingly, recent research has identified a putative tumor suppressor function for PRC2 in T-cell acute lymphoblastic leukemia. As such, chemical probes of H3K27me3 biology are urgently needed for mechanistic and translational research. Recent studies demonstrate that EZH2 knockdown in murine models of a genetically-defined subtype of acute leukemia (MLL-AF9) results in a less aggressive phenotype and cellular differentiation. PRC2 target genes are reactivated by RNA interference, including the tumor suppressors p16 and p19. Additionally, the well-studied MYC gene set that is associated with aggressive cancers was observed to be suppressed following EZH2 inactivation. The effect was generally modest as EZH1 could compensate and residual H3K27me3 was present in the EZH2 knockdown mice. An alternative knockdown of EED, another PRC2 subunit led to complete depletion of H3K27me3, and a dramatic response in the mouse model of leukemia. These data would suggest that, rather than blocking the methyltransferase activity of EZH2 in cancer, a more effective approach may be inhibition of CBX chromodomain binding to the H3K27me3 mark placed by EZH1 and EZH2. In support of this hypothesis, a discrete chromobox homolog (CBX8) has been shown to be required for MLL-AF9 induced leukemogenesis, using genetic constructs. Importantly, these studies using Cbx8-deficient mice failed to identify a lethal or debilitating phenotype, even with respect to hematopoiesis, supporting a putative therapeutic window for CBX inhibitors. As CBX chromodomains are the only reported chromatin readers for H3K27me3, molecules that inhibit the ability of CBX to bind H3K27me3 would serve as valuable chemical probes of polycomb biology in cancer, as well as in stem cell and developmental biology. CBX inhibitors could be used to address the hypothesis that polycomb readers are promising nodes for pharmacologic intervention in H3K27me3 enriched cancers.

Thus, there is a continuing need for pharmacologic agents that antagonize CBX chromodomains and that can be used to manipulate CBX in therapeutic or experimental applications.

SUMMARY OF INVENTION

In one aspect, the invention relates to compounds having the structure of Formula I or a pharmaceutically acceptable salt thereof:

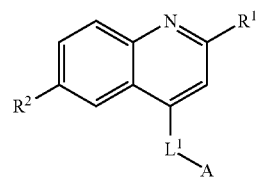

I wherein $R^1$, $R^2$, $L^1$ and A are defined herein.

In another aspect, the invention relates to compounds having the structure of Formula II or a pharmaceutically acceptable salt thereof:

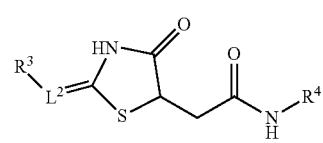

II wherein $R^3$, $R^4$, and $L^2$ are defined herein.

In another aspect, the invention relates to compounds having the structure of Formula III or a pharmaceutically acceptable salt thereof:

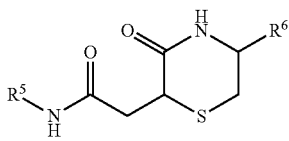

III wherein R⁵ and R⁶ are defined herein.

In another aspect, the invention relates to compounds having the structure of Formula IV, V, or IX or a pharmaceutically acceptable salt thereof:

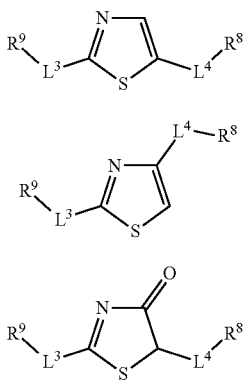

IV

V

IX wherein $R^8$, $R^9$, $L^3$ and $L^4$ are defined herein.

In another aspect, the invention relates to compounds having a structure of Formula VI or a pharmaceutically acceptable salt thereof:

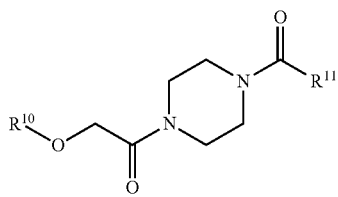

VI wherein $R^{10}$ and $R^{11}$ are defined herein.

In another aspect, the invention relates to compounds having a structure of Formula VII or a pharmaceutically acceptable salt thereof:

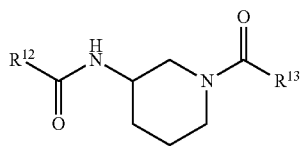

VII wherein $R^{12}$ and $R^{13}$ are defined herein.

In another aspect, the invention relates to compounds having a structure of Formula VIII or a pharmaceutically acceptable salt thereof:

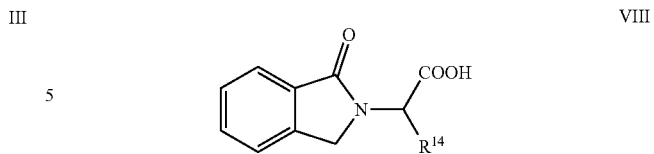

VIII wherein $R^{14}$ is defined herein.

In another aspect, the invention relates to pharmaceutical compositions of a compound of one of Formulas I-IX and a pharmaceutically acceptable carrier.

The invention also relates to methods of treating or preventing a disease or condition comprising administering a compound or composition of the invention. In certain embodiments, the disease is cancer. The invention further relates to methods of inhibiting proliferation of a cancer cell, comprising contacting a cancer cell with a compound or composition of the invention.

The invention also relates to methods of inhibiting CBX, comprising contacting a cell with a compound or composition of the invention.

DETAILED DESCRIPTION OF THE INVENTION

Figure 1:
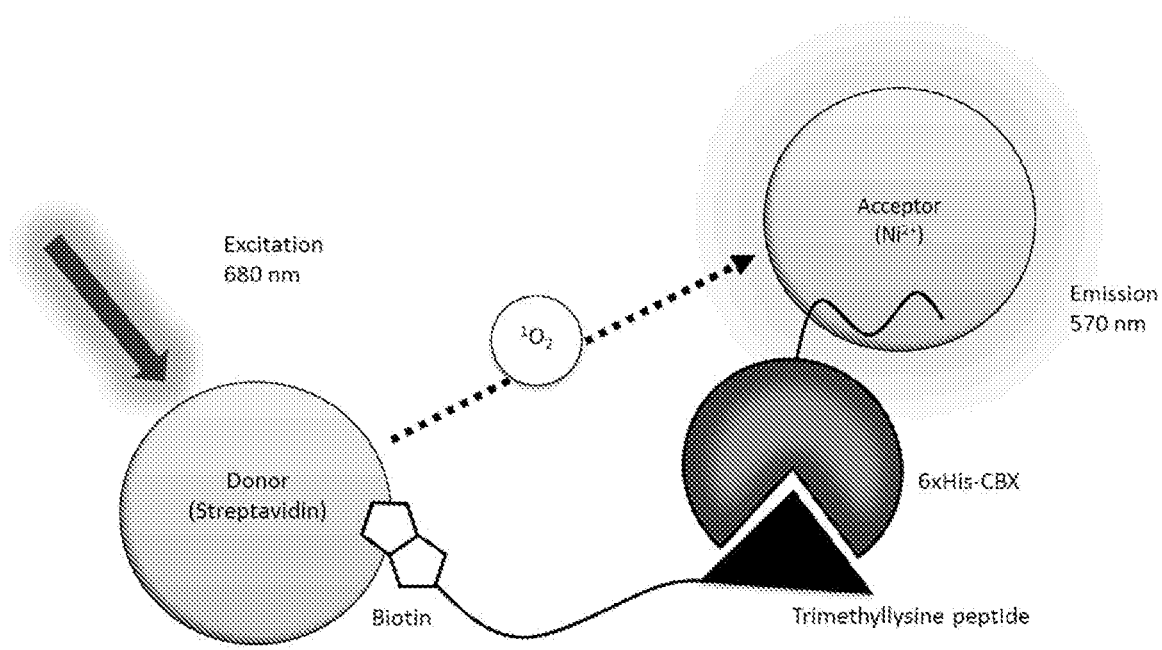
FIG. 1 is a schematic representation of the CBX AlphaScreen Assay.

In certain aspects, the invention provides various novel compounds, and pharmaceutical compositions thereof. In particular, such compounds are useful as CBX inhibitors, and thus can be used to treat or prevent a disease or condition (e.g., cancer).

I. Compounds

In certain embodiments, the invention relates to compounds having the structure of Formula (I), or a pharmaceutically acceptable salt thereof:

I

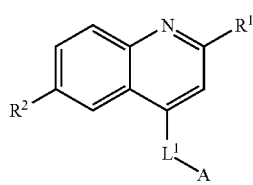

wherein $R^1$ is optionally substituted aryl or heteroaryl;

$R^2$ is H, halo, optionally substituted aryl, or optionally substituted heteroaryl;

$L^1$ is —C(O)—, —C(O)NH—, optionally substituted —C(O)NH-alkylene-, or —C(O)NHNCH—; and A is OH or optionally substituted heterocyclyl, aryl, or heteroaryl.

In certain embodiments, $R^1$ is

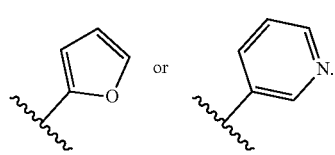 [SMILES: *c1ccco1 ; "or" ; *c1cccnc1]

In certain embodiments, $R^2$ is Br.

In certain embodiments, $R^2$ is

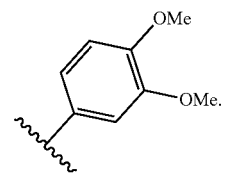 [SMILES: *c1ccc(OC)c(OC)c1]

In certain embodiments, A is

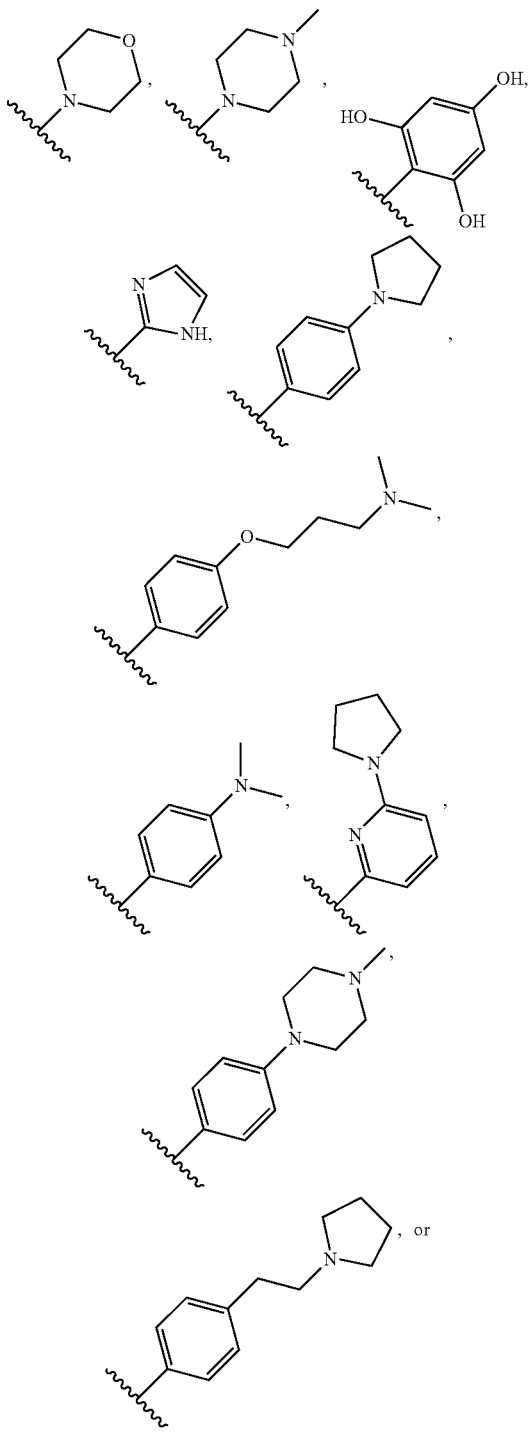

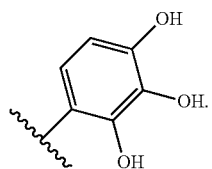 [SMILES: *c1ccc(O)c(O)c1O]

In certain embodiments, $L^1$ is

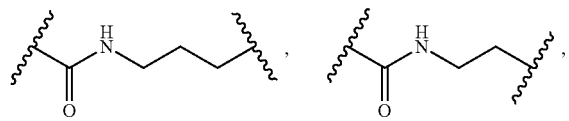

In certain embodiments, $L^1$-A is

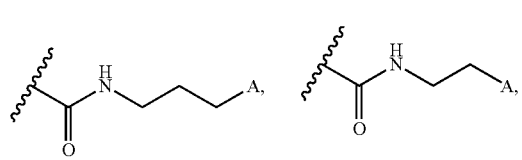

In certain embodiments, $L^1$ is

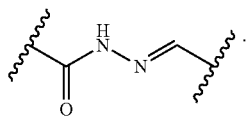 [SMILES: */C=N/NC(*)=O]

In certain embodiments, $L^1$-A is

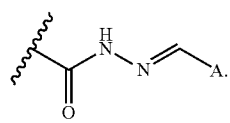

In certain embodiments, the invention relates to compounds having the structure compound having a structure of Formula II or a pharmaceutically acceptable salt thereof:

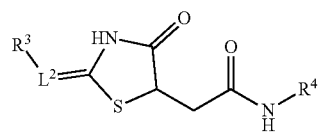

wherein $R^3$ is optionally substituted aryl, heteroaryl, —C(O)-aryl, alkyl, or alkoxycarbonyl;

$R^4$ is optionally substituted alkyl, aryl or heteroaryl; and $L^2$ is =N—C(O)—, =N—NCH—, =N—, or =N—NH—.

In certain embodiments, $R^3$ is

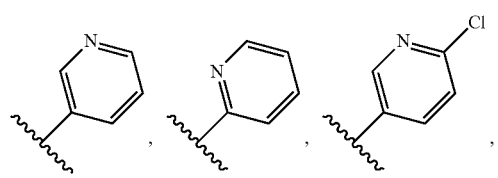

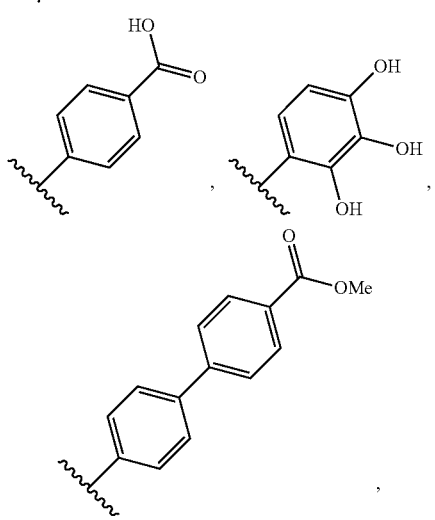

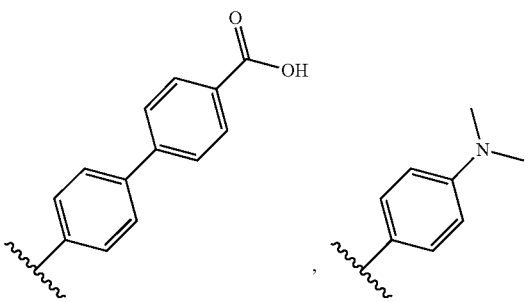

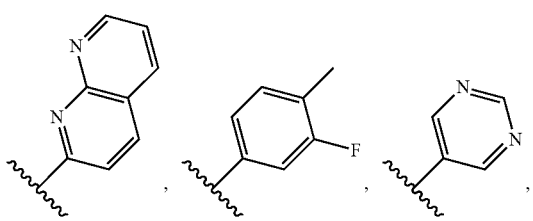

-continued

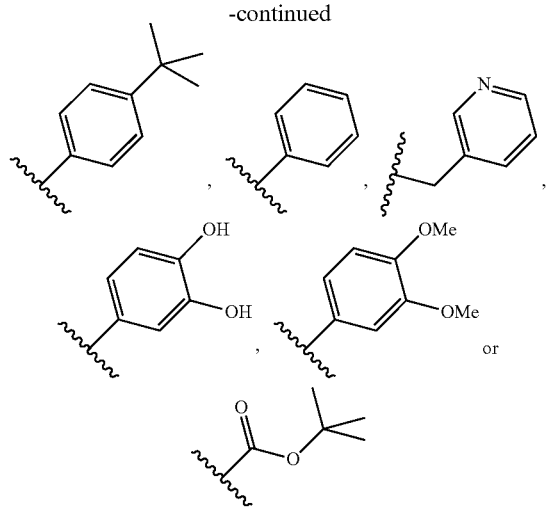

In certain embodiments, R⁴ is

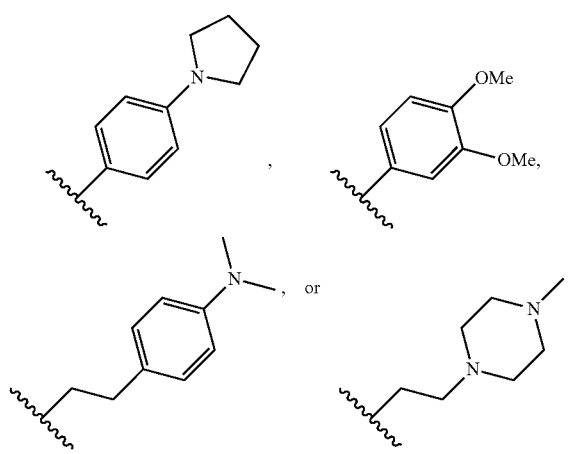

In certain embodiments, L² is

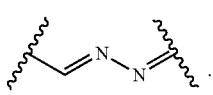 [SMILES: */C=N/N=*]

In certain embodiments, the invention relates to compounds having a structure of Formula III or a pharmaceutically acceptable salt thereof:

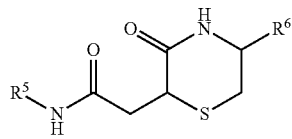

III wherein
R⁵ is optionally substituted aryl or heteroaryl;
R⁶ is —C(O)NH—NCH—R⁷ or —C(O)O-alkyl; and
R⁷ is optionally substituted aryl or heteroaryl.

In certain embodiments, R⁵ is

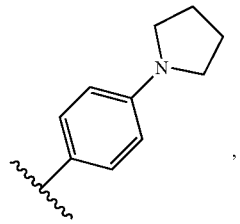 [SMILES: *c1ccc(N2CCCC2)cc1]

In certain embodiments, R⁷ is

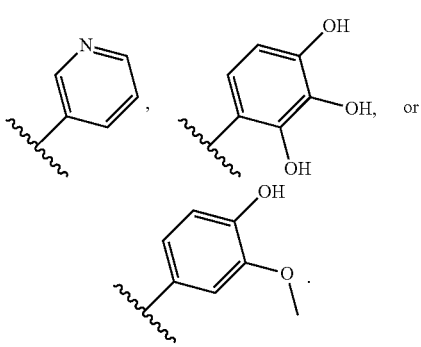

In certain embodiments, R⁶ is

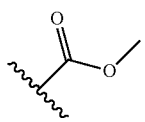

In certain embodiments, the invention relates to compounds having a structure of Formula IV, V, IX or a pharmaceutically acceptable salt thereof:

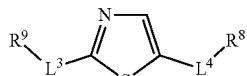

IV

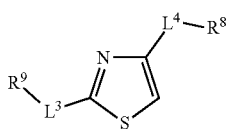

V

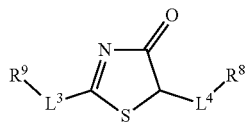

IX wherein
R⁸ is optionally substituted alkyl, aryl, or heteroaryl;
R⁹ is optionally substituted aryl or heteroaryl;
L³ is —NH—CO—NH—, —NH—CO—, —NH—NCH₂—, —NH—, —CH₂—, or —CH₂—NH—CO—; and $L^4$ is absent or is
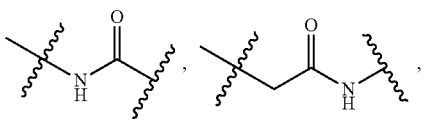
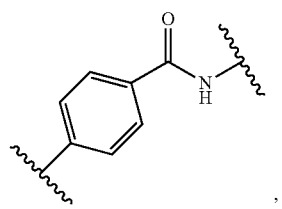
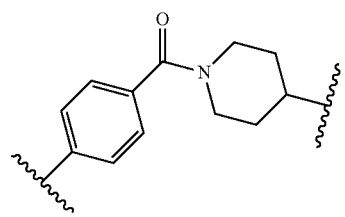
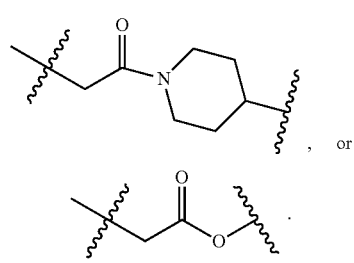, or
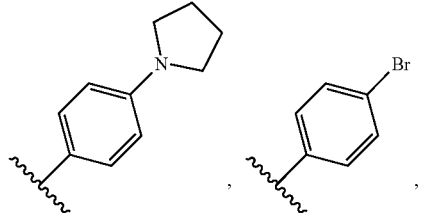.
In certain embodiments, $R^8$ is
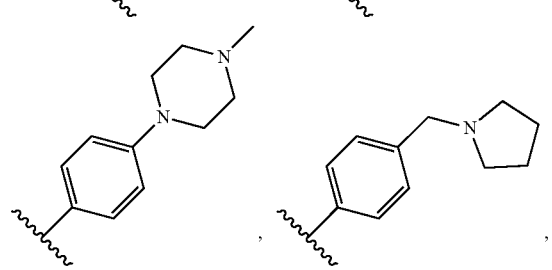
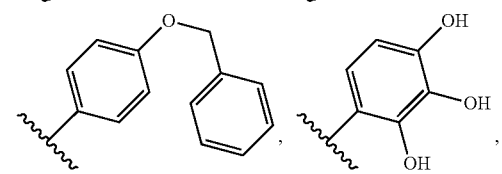
-continued
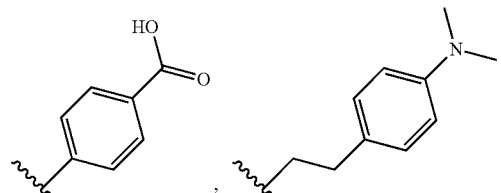
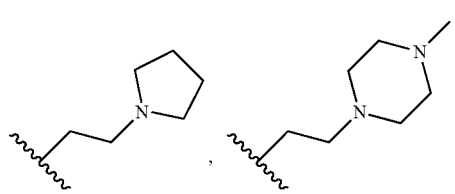
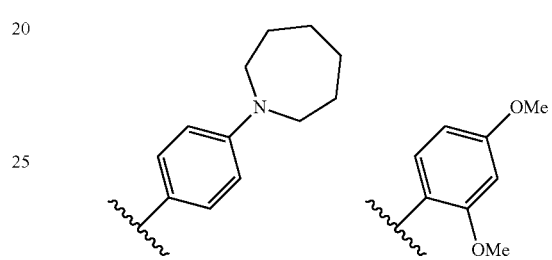
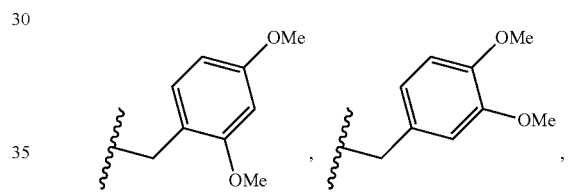
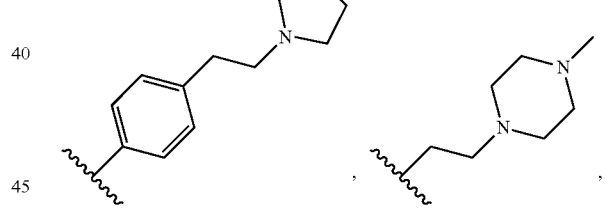
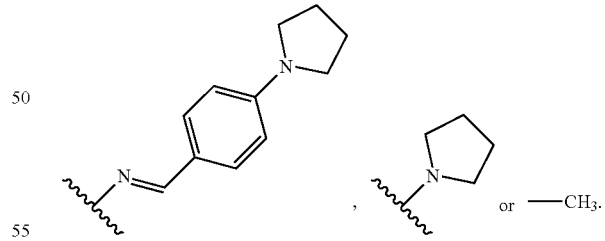 or —CH$_3$.
In certain embodiments, $R^9$ is
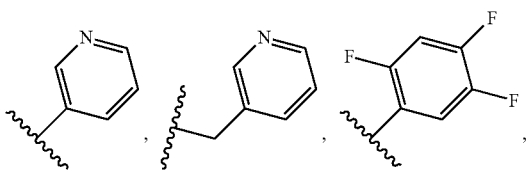

In certain embodiments, $L^4$ is

In certain embodiments, the invention relates to compounds having a structure of Formula VI or a pharmaceutically acceptable salt thereof:

VI wherein
$R^{10}$ is optionally substituted alkyl, aryl or heteroaryl; and
$R^{11}$ is optionally substituted aryl or heteroaryl.

In certain embodiments, $R^{10}$ is

In certain embodiments, $L^3$-$R^9$ is —NH—CO—NH—$R^9$, —NH—CO—$R^9$, —NH—NCH$_2$—$R^9$, or —CH$_2$—NH—CO—$R^9$.

In certain embodiments, $R^{11}$ is

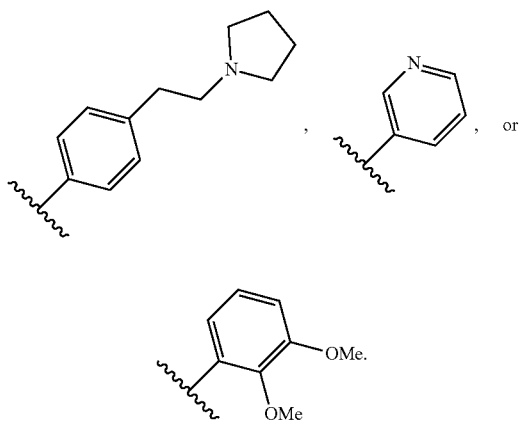 [SMILES: *c1ccc(CCN2CCCC2)cc1 ; *c1cccnc1 ; *c1cccc(OC)c1OC]

In certain embodiments, the invention relates to compounds having a structure of Formula VII or a pharmaceutically acceptable salt thereof:

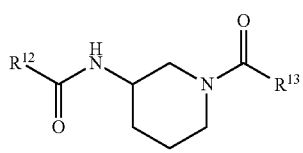

VII wherein
$R^{12}$ is optionally substituted alkyl, aryl or heteroaryl; and
$R^{13}$ is optionally substituted aryl or heteroaryl.

In certain embodiments, $R^{13}$ is

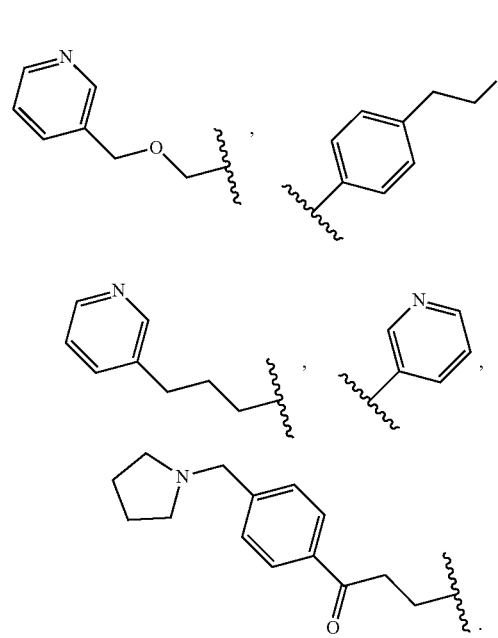

In certain embodiments, $R^{12}$ is

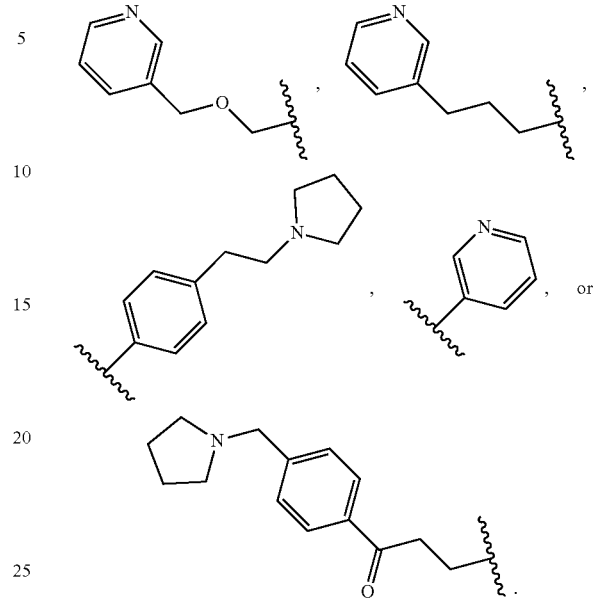

In certain embodiments, the invention relates to compounds having a structure of Formula VIII or a pharmaceutically acceptable salt thereof:

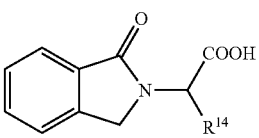

VIII wherein $R^{14}$ is optionally substituted alkyl or aryl.
In certain embodiments, $R^{14}$ is -ethyl,

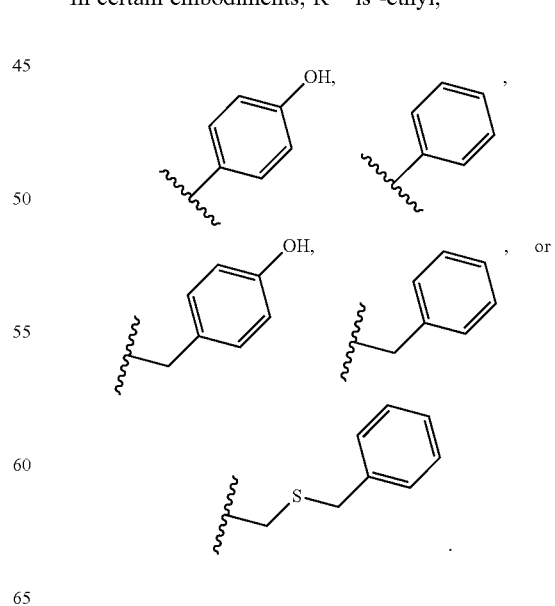

In certain embodiments, the compound is any of those described herein provided that the compound is not

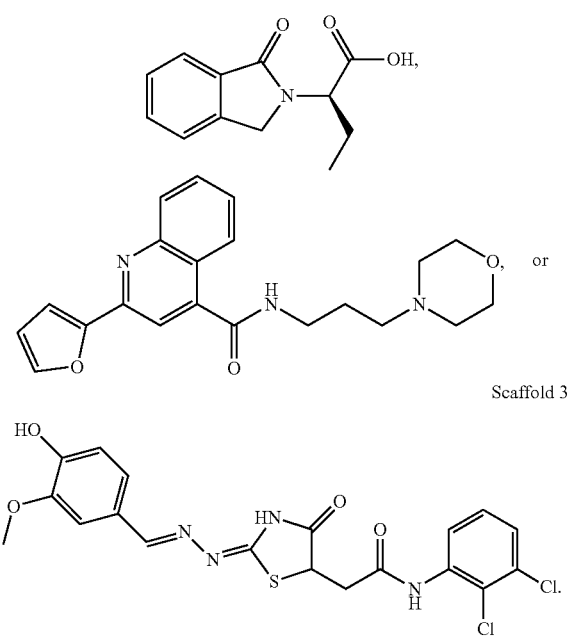

Scaffold 3

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, as will be described in detail below, the present invention relates to methods of treating or preventing a disease or condition with a compound of Formula I, or a pharmaceutically acceptable salt thereof. In certain embodiments, the therapeutic preparation may be enriched to provide predominantly one enantiomer of a compound of one of Formulas I-IX. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound of one of Formulas I-IX. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient in the treatment of a disease or condition, comprising an effective amount of any compound of one of Formulas I-IX, and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Exemplary compounds of the invention are depicted in Table 1. The compounds of Table 1 are understood to encompass both the free base and the conjugate acid. For example, the compounds in Table 1 may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

TABLE 1

Exemplary Compounds

| Structure | Compound Name | Alternate name |
|---|---|---|
| 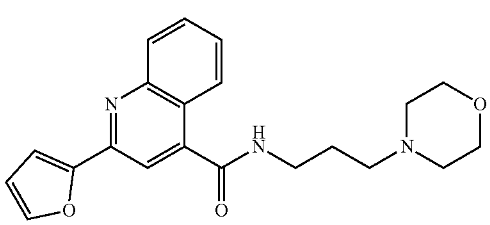 [SMILES: O=C(NCCCN1CCOCC1)c1cc(-c2ccco2)nc2ccccc12] | ACV-01 | ACV-1-180 |

TABLE 1-continued
Exemplary Compounds
| Structure | Compound Name | Alternate name |
|---|---|---|
| 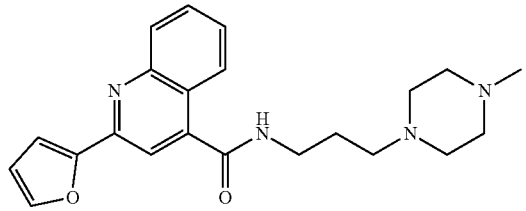 [SMILES: CN1CCN(CCCNC(=O)c2cc(-c3ccco3)nc3ccccc23)CC1] | ACV-02 | ACV-1-182 |
| 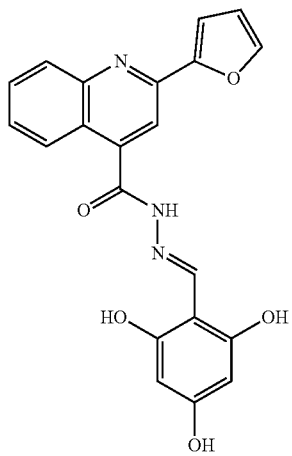 [SMILES: O=C(N/N=C/c1c(O)cc(O)cc1O)c1cc(-c2ccco2)nc2ccccc12] | ACV-03 | ACV-1-183-A |
| 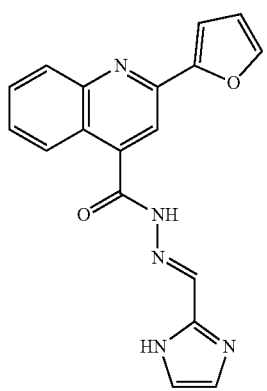 [SMILES: O=C(N/N=C/c1ncc[nH]1)c1cc(-c2ccco2)nc2ccccc12] | ACV-04 | ACV-1-183-B |

TABLE 1-continued

Exemplary Compounds

| Structure | Compound Name | Alternate name |
|---|---|---|
| 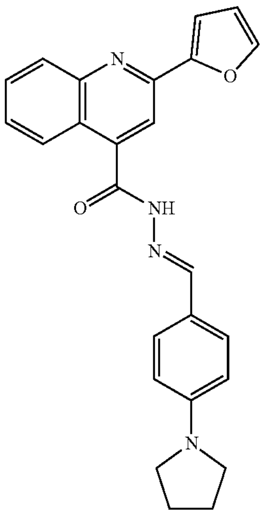 [SMILES: O=C(N/N=C/c1ccc(N2CCCC2)cc1)c1cc(-c2ccco2)nc2ccccc12] | ACV-05 | ACV-1-183-D |
| 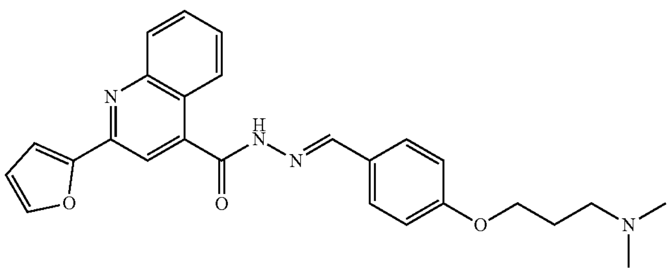 [SMILES: CN(C)CCCOc1ccc(/C=N/NC(=O)c2cc(-c3ccco3)nc3ccccc23)cc1] | ACV-06 | ACV-1-183-E |
| 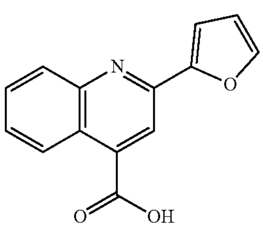 [SMILES: O=C(O)c1cc(-c2ccco2)nc2ccccc12] | ACV-07 (1) | ACV-1-190, AJF-109 |
| | ACV-07 (2) | ACV-2-192 |
| 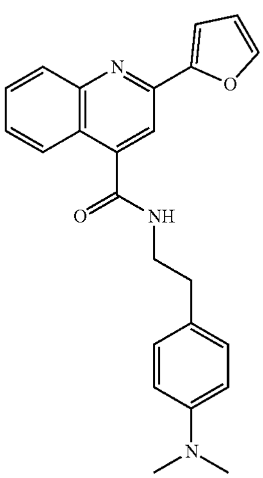 [SMILES: CN(C)c1ccc(CCNC(=O)c2cc(-c3ccco3)nc3ccccc23)cc1] | ACV-08 | ACV-1-191 |

TABLE 1-continued

Exemplary Compounds

| Structure | Compound Name | Alternate name |
|---|---|---|
| 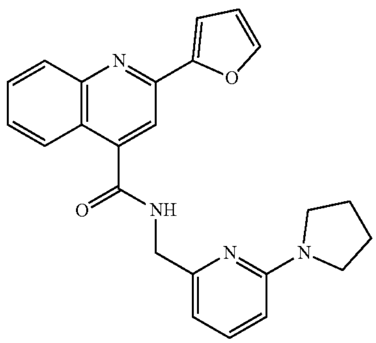 [SMILES: O=C(NCc1cccc(N2CCCC2)n1)c1cc(-c2ccco2)nc2ccccc12] | ACV-09 | ACV-1-195-A |
| 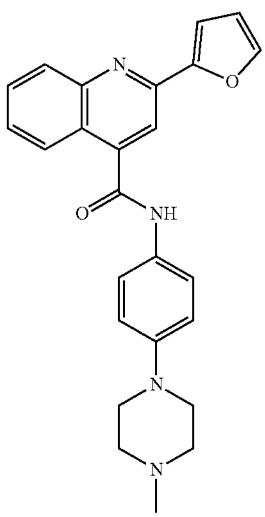 [SMILES: CN1CCN(c2ccc(NC(=O)c3cc(-c4ccco4)nc4ccccc34)cc2)CC1] | ACV-10 | ACV-1-195-D |
| 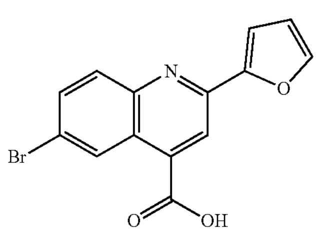 [SMILES: O=C(O)c1cc(-c2ccco2)nc2ccc(Br)cc12] | ACV-11 | ACV-1-202 |

TABLE 1-continued

Exemplary Compounds

| Structure | Compound Name | Alternate name |
|---|---|---|
| 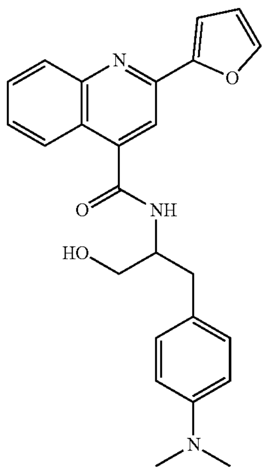 [SMILES: CN(C)c1ccc(CC(CO)NC(=O)c2cc(-c3ccco3)nc3ccccc23)cc1] | ACV-12 | ACV-1-204 |
| 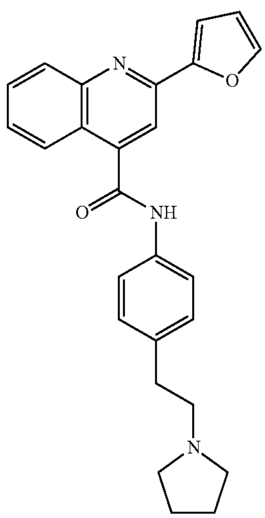 [SMILES: O=C(Nc1ccc(CCN2CCCC2)cc1)c1cc(-c2ccco2)nc2ccccc12] | ACV-13 | ACV-1-205 |
| 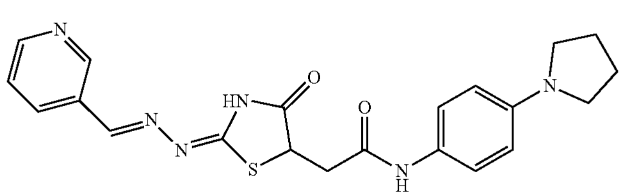 [SMILES: O=C(CC1S/C(=N/N=C/c2cccnc2)NC1=O)Nc1ccc(N2CCCC2)cc1] | ACV-14 (1) | ACV-1-242, F1 |
| | ACV-14 (2) | ACV-2-129 |
| 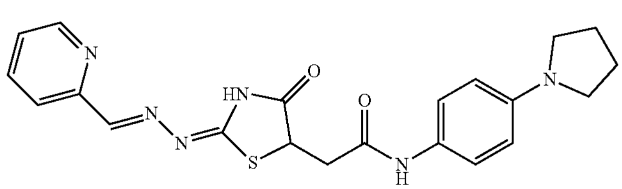 [SMILES: O=C(CC1S/C(=N/N=C/c2ccccn2)NC1=O)Nc1ccc(N2CCCC2)cc1] | ACV-15 | ACV-1-258-A, E12 |

TABLE 1-continued

Exemplary Compounds

| Structure | Compound Name | Alternate name |
|---|---|---|
| 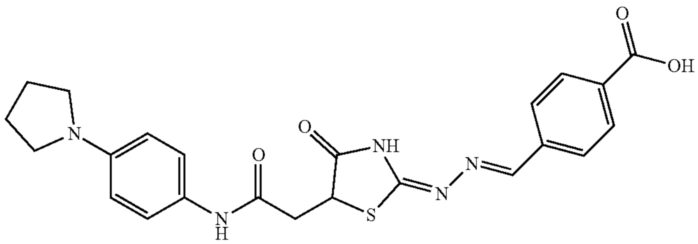 [SMILES: O=C(CC1S/C(=N/N=C/c2ccc(C(=O)O)cc2)NC1=O)Nc1ccc(N2CCCC2)cc1] | ACV-16 | ACV-1-258-B |
| 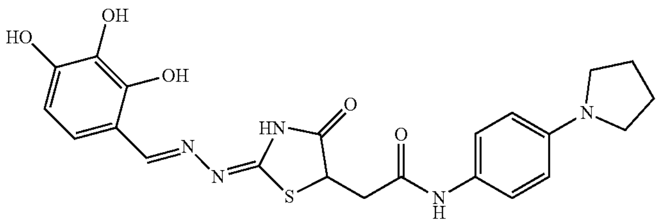 [SMILES: O=C(CC1S/C(=N/N=C/c2ccc(O)c(O)c2O)NC1=O)Nc1ccc(N2CCCC2)cc1] | ACV-17 (1) | ACV-1-258-C, A5 |
| 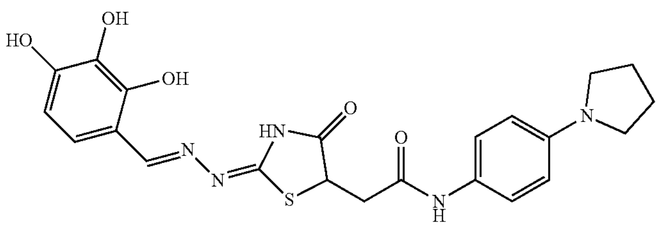 [SMILES: O=C(CC1S/C(=N/N=C/c2ccc(O)c(O)c2O)NC1=O)Nc1ccc(N2CCCC2)cc1] | ACV-17 (2) | ACV-2-165 |
| 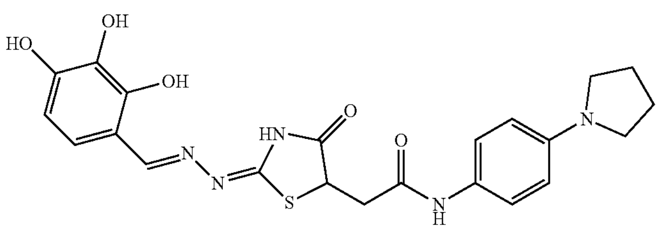 [SMILES: O=C(CC1S/C(=N/N=C/c2ccc(O)c(O)c2O)NC1=O)Nc1ccc(N2CCCC2)cc1] | ACV-17(3) | ACV-2-189 |
| 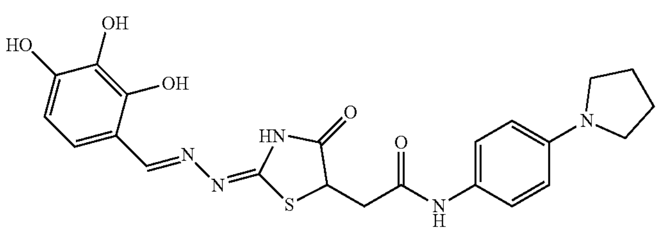 [SMILES: O=C(CC1S/C(=N/N=C/c2ccc(O)c(O)c2O)NC1=O)Nc1ccc(N2CCCC2)cc1] | ACV-17(4) | ACV-2-206-A |
| 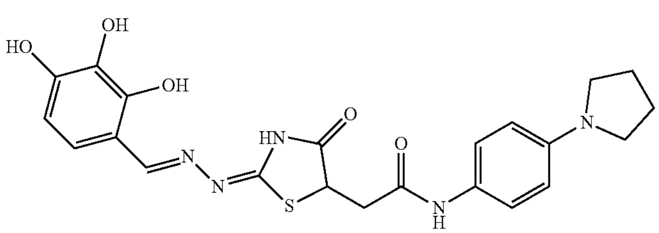 [SMILES: O=C(CC1S/C(=N/N=C/c2ccc(O)c(O)c2O)NC1=O)Nc1ccc(N2CCCC2)cc1] | ACV-17(CP) | ACV-258C (CP) |
| stereoisomer of ACV-17 | ACV-17* (P1) | ACV-258C (P1) |
| The other stereoisomer of ACV-17 | ACV-17* (P2) | ACV-258C (P2) |

TABLE 1-continued
Exemplary Compounds
| Structure | Compound Name | Alternate name |
|---|---|---|
| 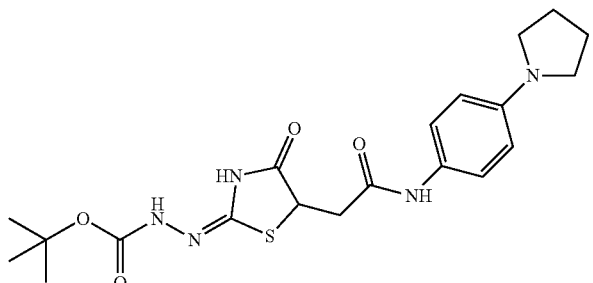 | ACV-18 | ACV-1-259 |
| FALK(me3)SK peptide | ACV-19 | ACV-1-261 |
| 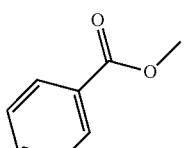 | ACV-20 | ACV-1-273 |
| 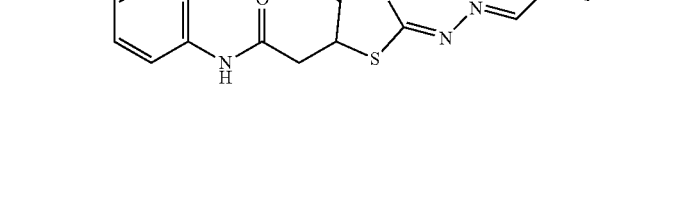 | ACV-21 | ACV-1-283-B |
| 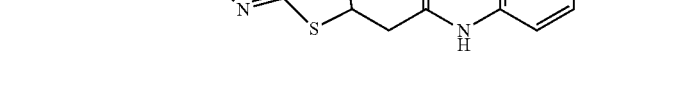 | ACV-22 | ACV-1-285-D1/ACV-1-285-MIX |
| | ACV-22 | ACV-1-285-D1/ACV-1-285-MIX |

TABLE 1-continued

Exemplary Compounds

| Structure | Compound Name | Alternate name |
|---|---|---|
| 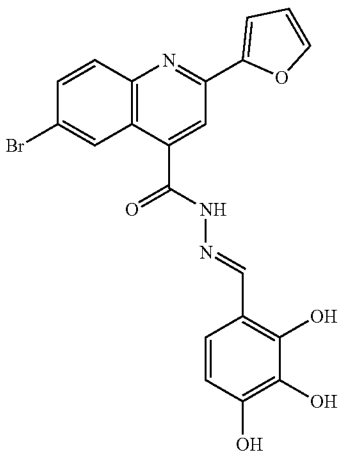 [SMILES: O=C(N/N=C/c1ccc(O)c(O)c1O)c1cc(-c2ccco2)nc2ccc(Br)cc12] | ACV-23 | ACV-1-288 |
| 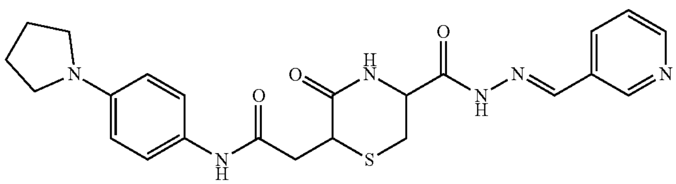 [SMILES: O=C(CC1SCC(C(=O)N/N=C/c2cccnc2)NC1=O)Nc1ccc(N2CCCC2)cc1] | ACV-24 | ACV-2-007-A |
| 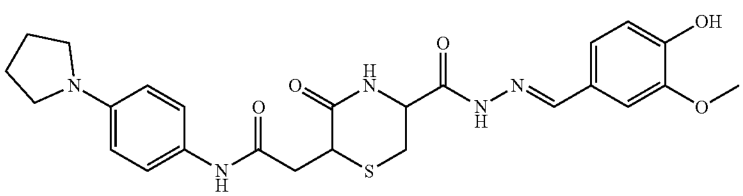 [SMILES: COc1cc(/C=N/NC(=O)C2CSC(CC(=O)Nc3ccc(N4CCCC4)cc3)C(=O)N2)ccc1O] | ACV-25 | ACV-2-007-B |
| 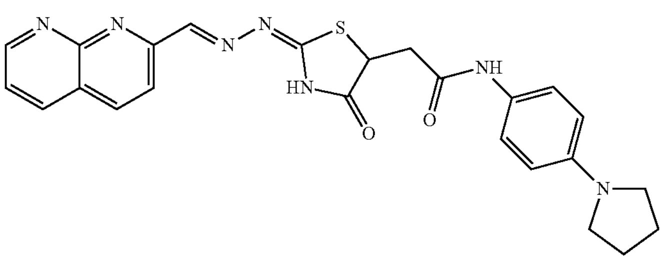 [SMILES: O=C(CC1S/C(=N/N=C/c2ccc3cccnc3n2)NC1=O)Nc1ccc(N2CCCC2)cc1] | ACV-26 | ACV-2-011-A |
| 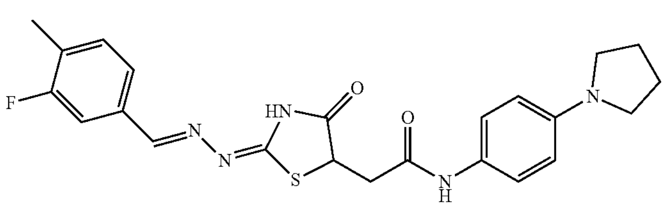 [SMILES: Cc1ccc(/C=N/N=C2\NC(=O)C(CC(=O)Nc3ccc(N4CCCC4)cc3)S2)cc1F] | ACV-27 | ACV-2-011-B |
| 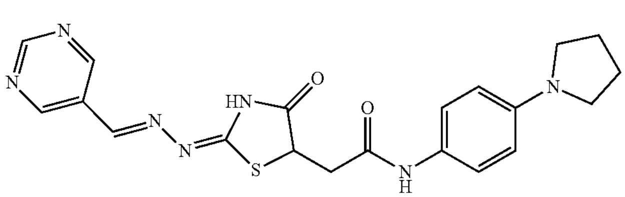 [SMILES: O=C(CC1S/C(=N/N=C/c2cncnc2)NC1=O)Nc1ccc(N2CCCC2)cc1] | ACV-28 | ACV-2-015 |

TABLE 1-continued

Exemplary Compounds

| Structure | Compound Name | Alternate name |
|---|---|---|
|  | ACV-29 | ACV-2-016-A/B |
|  | ACV-29 | ACV-2-016-A/B |
| 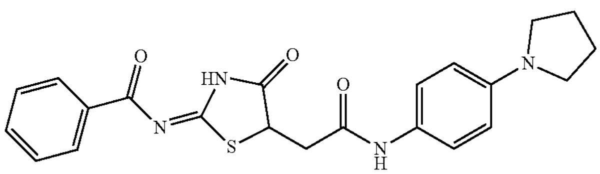 [SMILES: O=C(CC1S/C(=N/C(=O)c2ccccc2)NC1=O)Nc1ccc(N2CCCC2)cc1] | ACV-30 | ACV-2-019 |
| 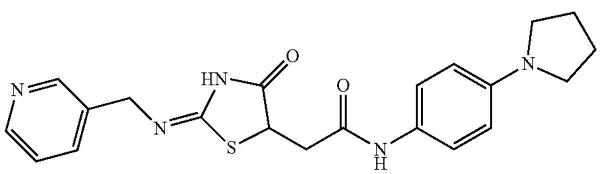 [SMILES: O=C(CC1S/C(=N/Cc2cccnc2)NC1=O)Nc1ccc(N2CCCC2)cc1] | ACV-31 | ACV-2-023 |
| 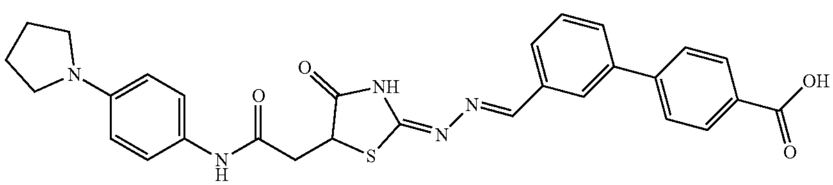 [SMILES: O=C(CC1S/C(=N/N=C/c2cccc(-c3ccc(C(=O)O)cc3)c2)NC1=O)Nc1ccc(N2CCCC2)cc1] | ACV-32 | ACV-2-024 |
| 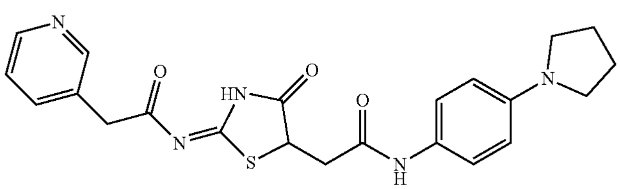 [SMILES: O=C(Cc1cccnc1)/N=C1\NC(=O)C(CC(=O)Nc2ccc(N3CCCC3)cc2)S1] | ACV-33 | ACV-2-026 |
| 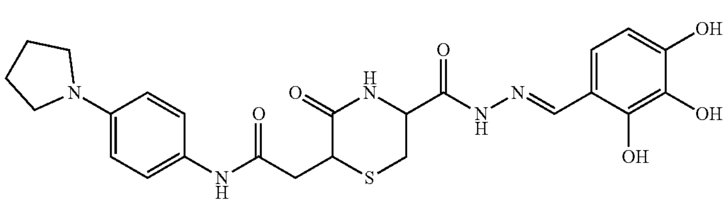 [SMILES: O=C(CC1SCC(C(=O)N/N=C/c2ccc(O)c(O)c2O)NC1=O)Nc1ccc(N2CCCC2)cc1] | ACV-34 | ACV-2-029 |
| 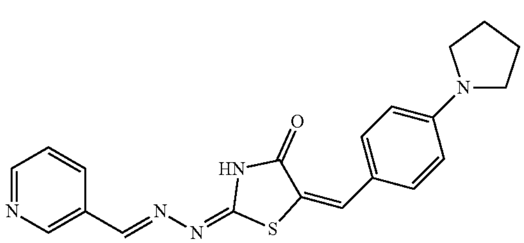 [SMILES: O=C1N/C(=N\N=C\c2cccnc2)S/C1=C/c1ccc(N2CCCC2)cc1] | ACV-35 | ACV-2-049 |

TABLE 1-continued
Exemplary Compounds
| Structure | Compound Name | Alternate name |
|---|---|---|
| 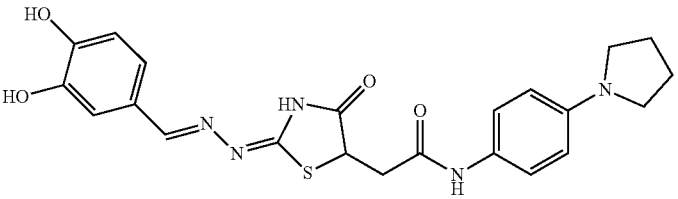 [SMILES: O=C(CC1S/C(=N/N=C/c2ccc(O)c(O)c2)NC1=O)Nc1ccc(N2CCCC2)cc1] | ACV-36 (1) | ACV-2-082 |
|  | ACV-36 (2) | ACV-2-163 |
| 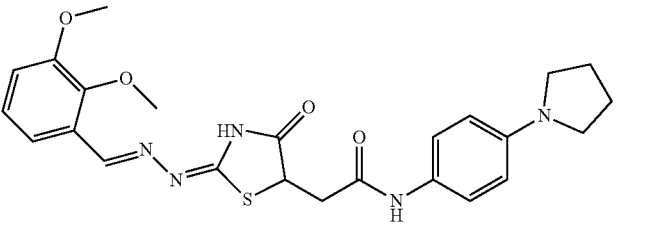 [SMILES: COc1cccc(/C=N/N=C2\NC(=O)C(CC(=O)Nc3ccc(N4CCCC4)cc3)S2)c1OC] | ACV-37 | ACV-2-083 |
| 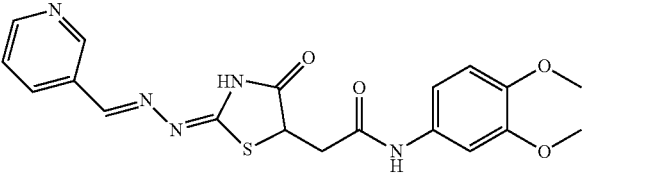 [SMILES: COc1ccc(NC(=O)CC2S/C(=N/N=C/c3cccnc3)NC2=O)cc1OC] | ACV-38 | ACV-2-084 |
| 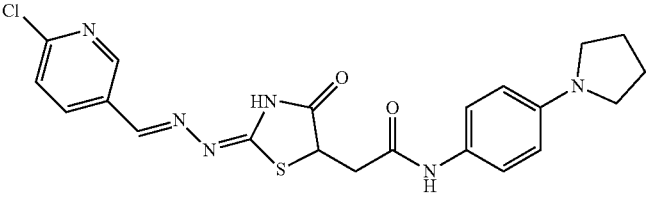 [SMILES: O=C(CC1S/C(=N/N=C/c2ccc(Cl)nc2)NC1=O)Nc1ccc(N2CCCC2)cc1] | ACV-39 | ACV-2-108 |
| 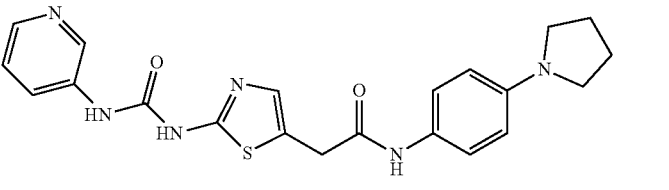 [SMILES: O=C(Cc1cnc(NC(=O)Nc2cccnc2)s1)Nc1ccc(N2CCCC2)cc1] | ACV-40 | ACV-2-112 |
| 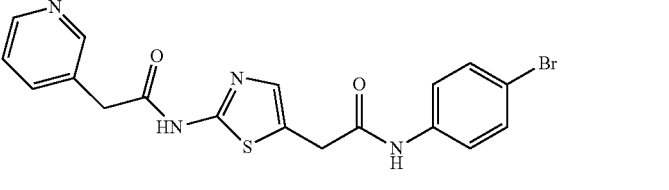 [SMILES: O=C(Cc1cnc(NC(=O)Cc2cccnc2)s1)Nc1ccc(Br)cc1] | ACV-41 | ACV-2-115 |
| 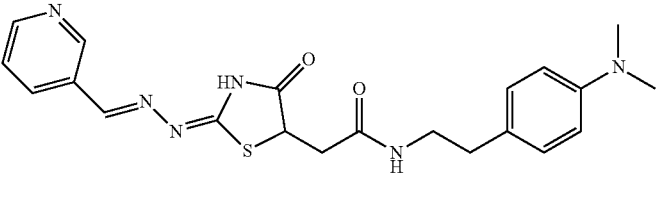 [SMILES: CN(C)c1ccc(CCNC(=O)CC2S/C(=N/N=C/c3cccnc3)NC2=O)cc1] | ACV-42 | ACV-2-121 |

TABLE 1-continued

Exemplary Compounds

| Structure | Compound Name | Alternate name |
|---|---|---|
| 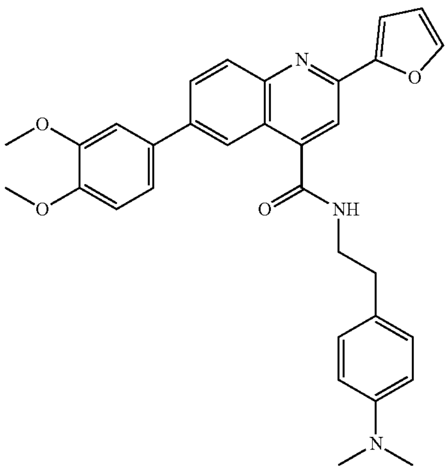 [SMILES: COc1ccc(-c2ccc3nc(-c4ccco4)cc(C(=O)NCCc4ccc(N(C)C)cc4)c3c2)cc1OC] | ACV-43 | ACV-2-123 |
| 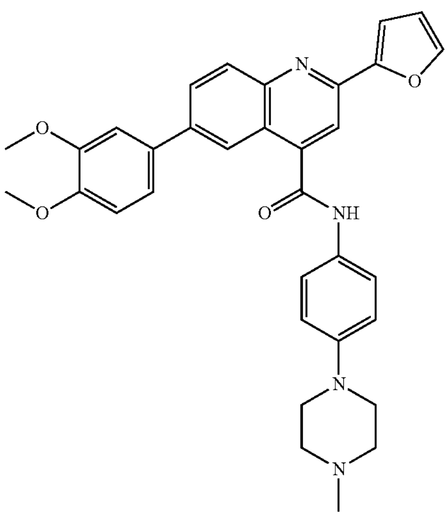 [SMILES: COc1ccc(-c2ccc3nc(-c4ccco4)cc(C(=O)Nc4ccc(N5CCN(C)CC5)cc4)c3c2)cc1OC] | ACV-44 | ACV-2-127 |
| 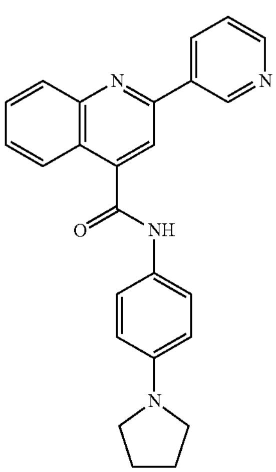 [SMILES: O=C(Nc1ccc(N2CCCC2)cc1)c1cc(-c2cccnc2)nc2ccccc12] | ACV-45 | ACV-2-132 |

TABLE 1-continued
Exemplary Compounds
| Structure | Compound Name | Alternate name |
|---|---|---|
| 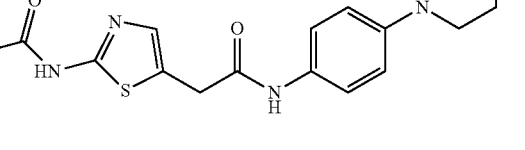 | ACV-46 | ACV-2-138 |
| 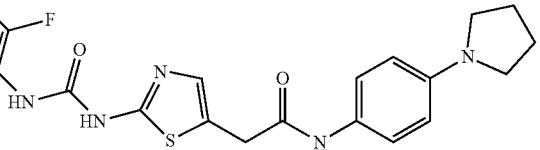 | ACV-47 | ACV-2-142 |
| 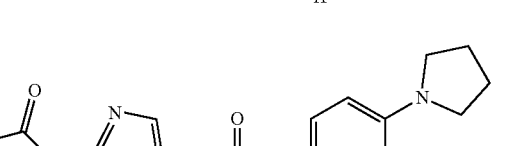 | ACV-48 (1) | ACV-2-147 |
|  | ACV-48 (2) | ACV-2-147 |
| 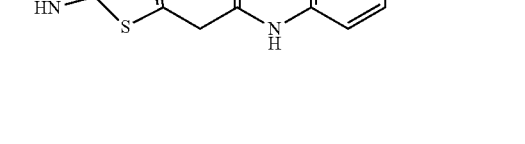 | ACV-49 | ACV-2-150 |
| 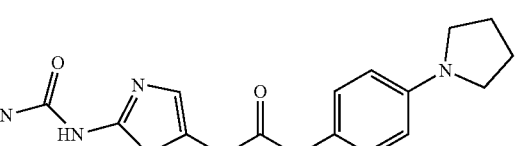 | ACV-50 | ACV-2-151 |
| 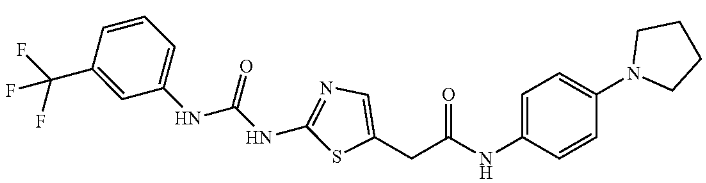 [SMILES: O=C(Cc1cnc(NC(=O)Nc2cccc(C(F)(F)F)c2)s1)Nc1ccc(N2CCCC2)cc1] | ACV-51 | ACV-2-152 |
| 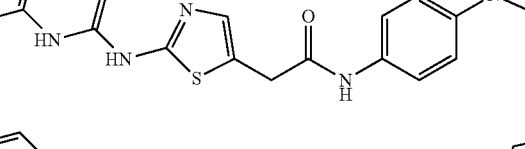 | ACV-52 | ACV-2-154 |

TABLE 1-continued
Exemplary Compounds
| Structure | Compound Name | Alternate name |
|---|---|---|
| 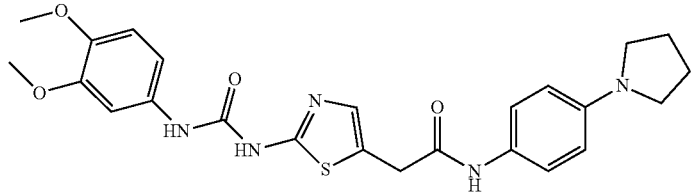 [SMILES: COc1ccc(NC(=O)Nc2ncc(CC(=O)Nc3ccc(N4CCCC4)cc3)s2)cc1OC] | ACV-53 | ACV-2-155 |
| 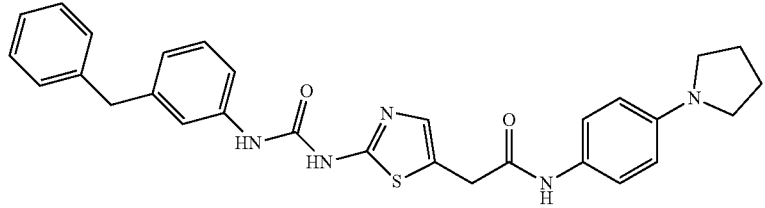 [SMILES: O=C(Cc1cnc(NC(=O)Nc2cccc(Cc3ccccc3)c2)s1)Nc1ccc(N2CCCC2)cc1] | ACV-54 | ACV-2-156 |
| 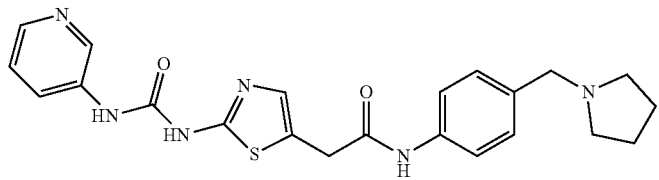 [SMILES: O=C(Cc1cnc(NC(=O)Nc2cccnc2)s1)Nc1ccc(CN2CCCC2)cc1] | ACV-55 | ACV-2-160 |
| 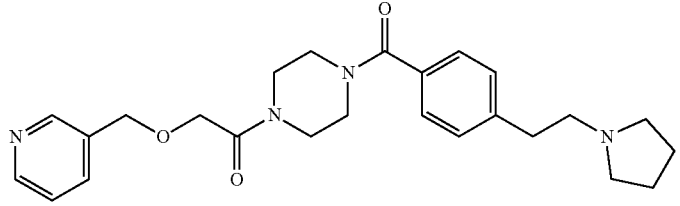 [SMILES: O=C(COCc1cccnc1)N1CCN(C(=O)c2ccc(CCN3CCCC3)cc2)CC1] | ACV-56 | CBX-01 |
| 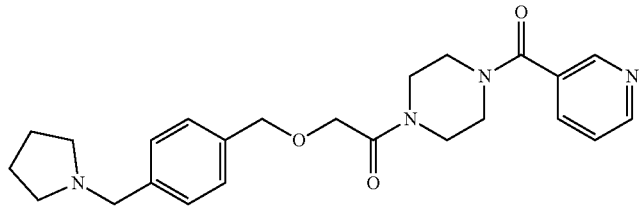 [SMILES: O=C(COCc1ccc(CN2CCCC2)cc1)N1CCN(C(=O)c2cccnc2)CC1] | ACV-57 | CBX-02 |
| a synthetic peptide with the sequence FALK(me3)S capped with a phenyl methyl ester on the N terminus | ACV-58 | ACV-2-130 |
| 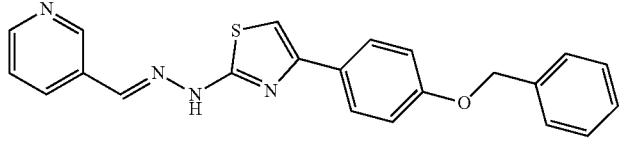 [SMILES: C(=N\Nc1nc(-c2ccc(OCc3ccccc3)cc2)cs1)/c1cccnc1] | ACV-59 | ACV-2-179 |
| 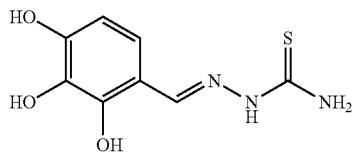 [SMILES: NC(=S)N/N=C/c1ccc(O)c(O)c1O] | ACV-60 | ACV-2-185 |

TABLE 1-continued

Exemplary Compounds

| Structure | Compound Name | Alternate name |
|---|---|---|
| 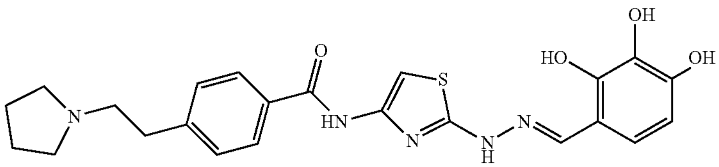 [SMILES: O=C(Nc1csc(N/N=C/c2ccc(O)c(O)c2O)n1)c1ccc(CCN2CCCC2)cc1] | ACV-61 | ACV-2-188 |
| 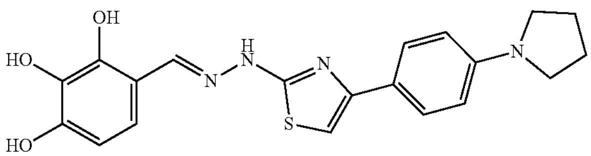 [SMILES: Oc1ccc(/C=N/Nc2nc(-c3ccc(N4CCCC4)cc3)cs2)c(O)c1O] | ACV-62 | ACV-2-191 |
| 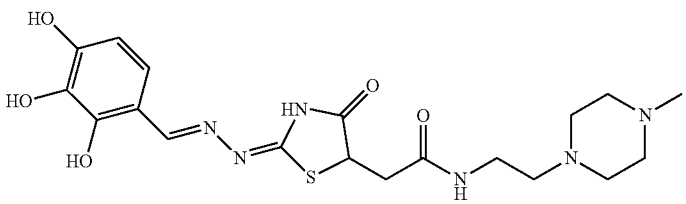 [SMILES: CN1CCN(CCNC(=O)CC2S/C(=N/N=C/c3ccc(O)c(O)c3O)NC2=O)CC1] | ACV-63 | ACV-2-195 |
| 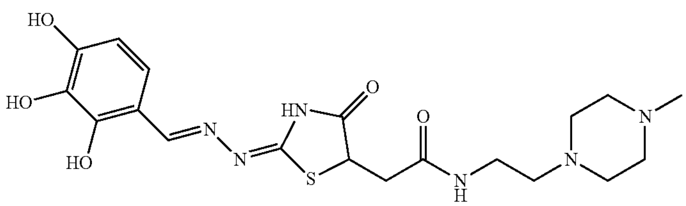 [SMILES: CN1CCN(CCNC(=O)CC2S/C(=N/N=C/c3ccc(O)c(O)c3O)NC2=O)CC1] | ACV-63 (2) | ACV-3-018 |
| 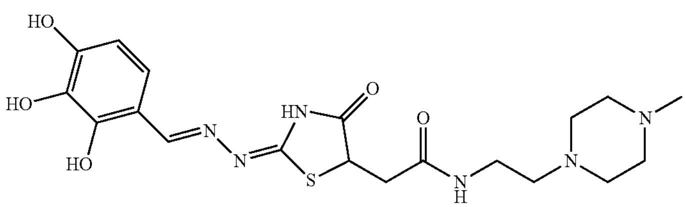 [SMILES: CN1CCN(CCNC(=O)CC2S/C(=N/N=C/c3ccc(O)c(O)c3O)NC2=O)CC1] | ACV 63 (CP) | ACV-2-195 (CP) |
| 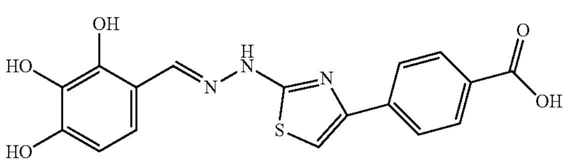 [SMILES: O=C(O)c1ccc(-c2csc(N/N=C/c3ccc(O)c(O)c3O)n2)cc1] | ACV-64 | ACV-2-203 |
| 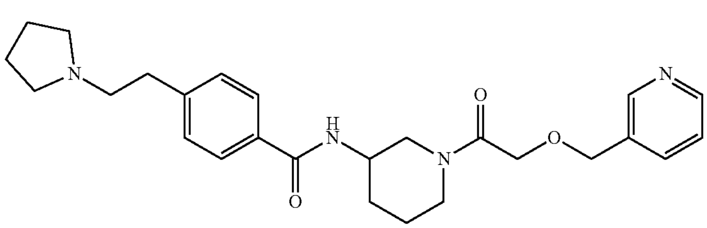 [SMILES: O=C(NC1CCCN(C(=O)COCc2cccnc2)C1)c1ccc(CCN2CCCC2)cc1] | ACV-65 | CBX-03a |

TABLE 1-continued

Exemplary Compounds

| Structure | Compound Name | Alternate name |
|---|---|---|
| 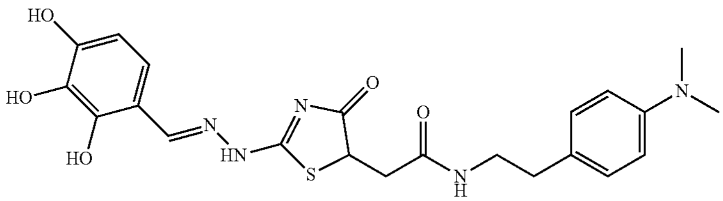 [SMILES: CN(C)c1ccc(CCNC(=O)CC2SC(N/N=C/c3ccc(O)c(O)c3O)=NC2=O)cc1] | ACV-66 | ACV-2-204 |
| 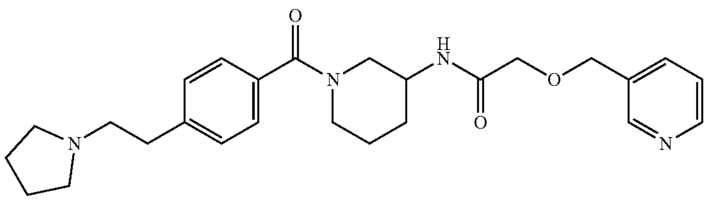 [SMILES: O=C(COCc1cccnc1)NC1CCCN(C(=O)c2ccc(CCN3CCCC3)cc2)C1] | ACV-67 | CBX-03 |
| 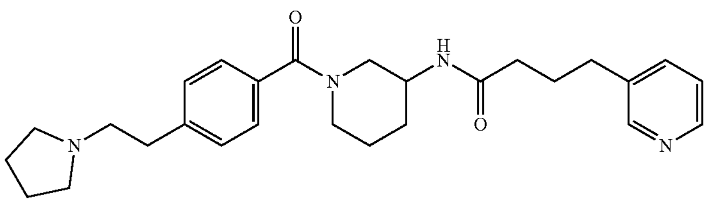 [SMILES: O=C(CCCc1cccnc1)NC1CCCN(C(=O)c2ccc(CCN3CCCC3)cc2)C1] | ACV-68 | CBX-04 |
| 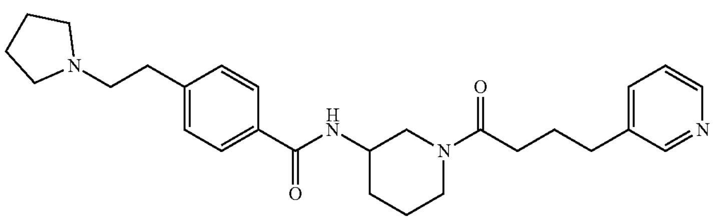 [SMILES: O=C(NC1CCCN(C(=O)CCCc2cccnc2)C1)c1ccc(CCN2CCCC2)cc1] | ACV-69 | CBX-04a |
| 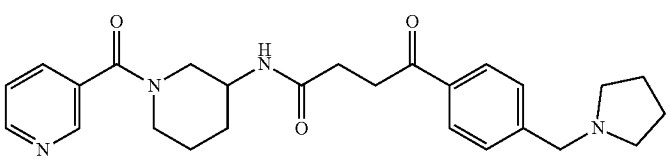 [SMILES: O=C(CCC(=O)c1ccc(CN2CCCC2)cc1)NC1CCCN(C(=O)c2cccnc2)C1] | ACV-70 | CBX-06 |
| 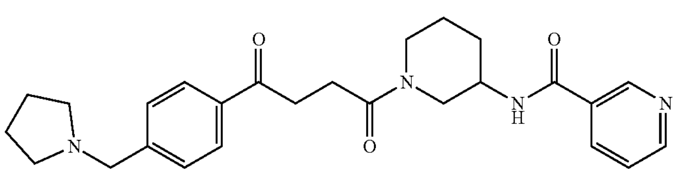 [SMILES: O=C(CCC(=O)N1CCCC(NC(=O)c2cccnc2)C1)c1ccc(CN2CCCC2)cc1] | ACV-71 | CBX-06a |
| 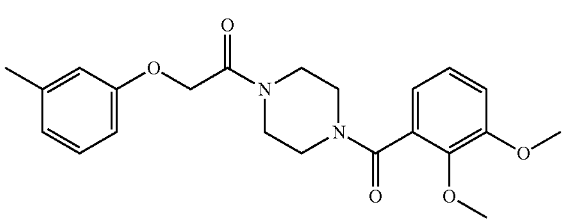 | ACV-72 | CBX-07 |

TABLE 1-continued

Exemplary Compounds

| Structure | Compound Name | Alternate name |
|---|---|---|
| 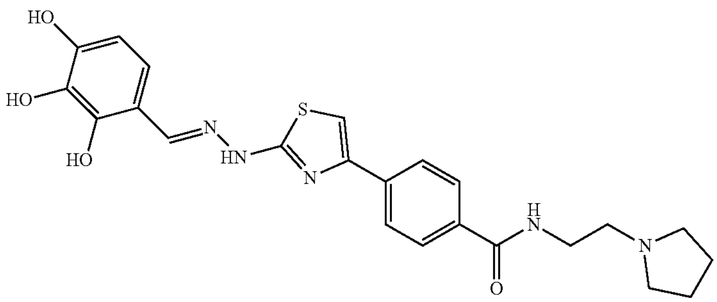 [SMILES: O=C(NCCN1CCCC1)c1ccc(-c2csc(N/N=C/c3ccc(O)c(O)c3O)n2)cc1] | ACV-73 | ACV-2-224 |
| 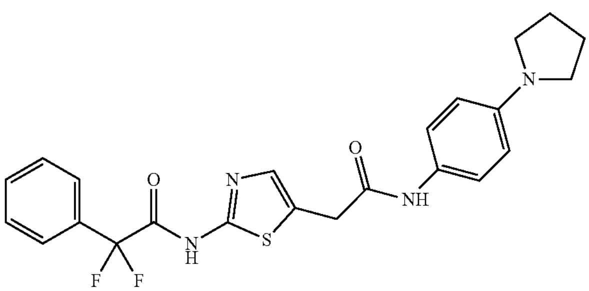 [SMILES: O=C(Cc1cnc(NC(=O)C(F)(F)c2ccccc2)s1)Nc1ccc(N2CCCC2)cc1] | ACV-74 | ACV-2-231 |
| 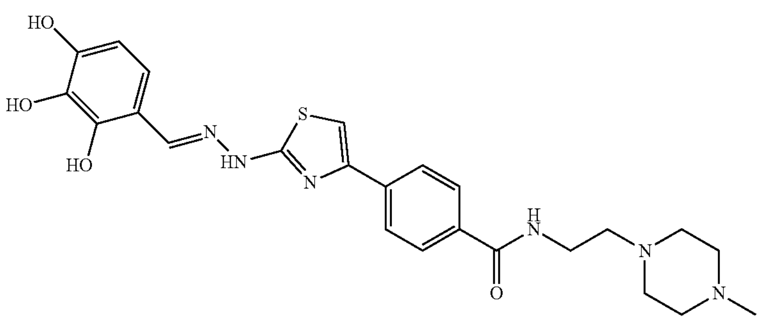 [SMILES: CN1CCN(CCNC(=O)c2ccc(-c3csc(N/N=C/c4ccc(O)c(O)c4O)n3)cc2)CC1] | ACV-75 | ACV-2-233 |
| 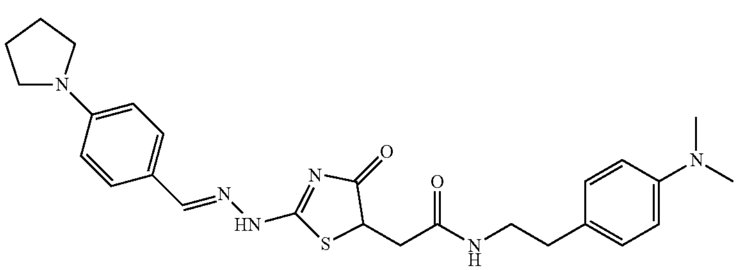 [SMILES: CN(C)c1ccc(CCNC(=O)CC2SC(N/N=C/c3ccc(N4CCCC4)cc3)=NC2=O)cc1] | ACV-76 | ACV-2-247 |
| 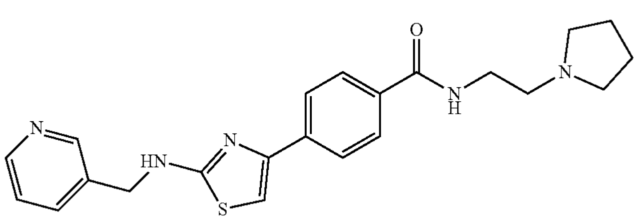 [SMILES: O=C(NCCN1CCCC1)c1ccc(-c2csc(NCc3cccnc3)n2)cc1] | ACV-77 | ACV-2-251 |

TABLE 1-continued

Exemplary Compounds

| Structure | Compound Name | Alternate name |
|---|---|---|
| 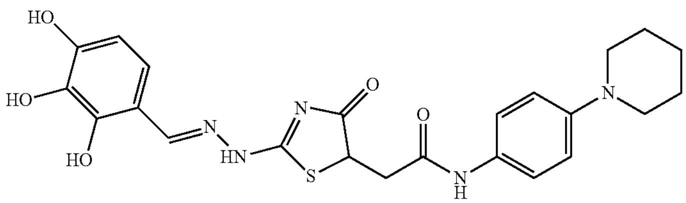 [SMILES: O=C(CC1SC(N/N=C/c2ccc(O)c(O)c2O)=NC1=O)Nc1ccc(N2CCCCC2)cc1] | ACV-78 | ACV-2-254 |
| 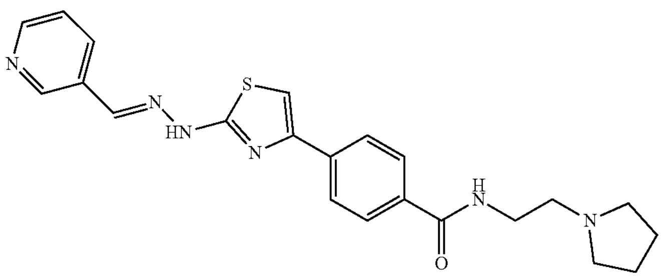 [SMILES: O=C(NCCN1CCCC1)c1ccc(-c2csc(N/N=C/c3cccnc3)n2)cc1] | ACV-79 | ACV-2-270 |
| 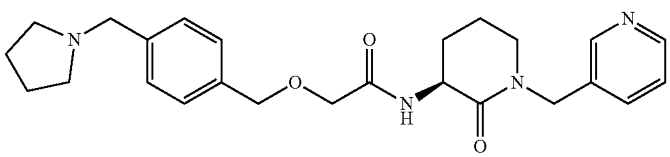 [SMILES: O=C(COCc1ccc(CN2CCCC2)cc1)N[C@H]1CCCN(Cc2cccnc2)C1=O] | ACV-80 | CBX-05 |
| 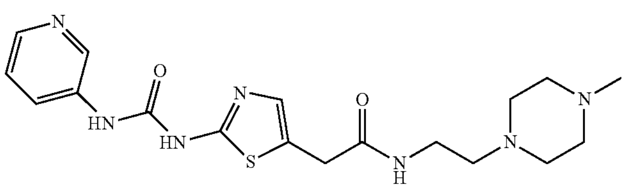 [SMILES: CN1CCN(CCNC(=O)Cc2cnc(NC(=O)Nc3cccnc3)s2)CC1] | ACV-81 | ACV-2-287 |
| 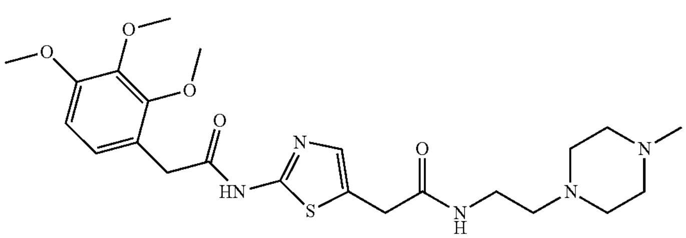 | ACV-82 | ACV-2-288 |
| 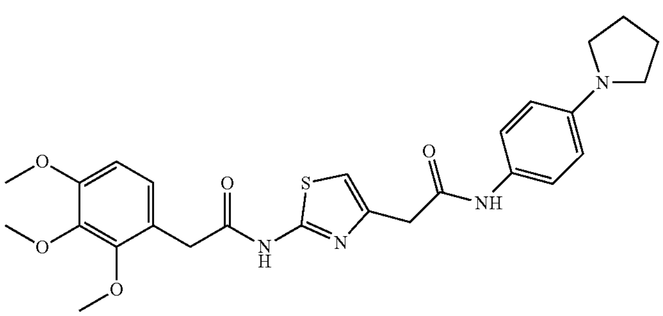 [SMILES: COc1ccc(CC(=O)Nc2nc(CC(=O)Nc3ccc(N4CCCC4)cc3)cs2)c(OC)c1OC] | ACV-83 | ACV-2-293 |

TABLE 1-continued

Exemplary Compounds

| Structure | Compound Name | Alternate name |
|---|---|---|
| 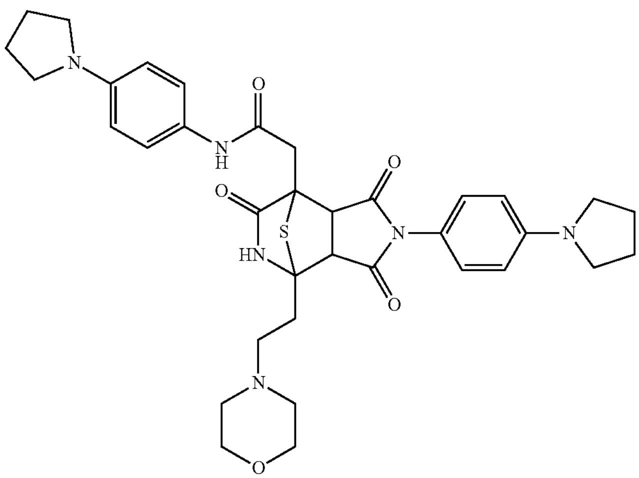 [SMILES: O=C(CC12SC(CCN3CCOCC3)(NC1=O)C1C(=O)N(c3ccc(N4CCCC4)cc3)C(=O)C12)Nc1ccc(N2CCCC2)cc1] | ACV-84 | ACV-2-294 |
| 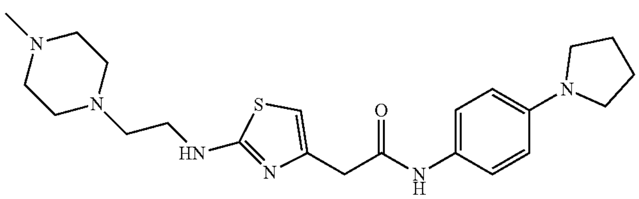 [SMILES: CN1CCN(CCNc2nc(CC(=O)Nc3ccc(N4CCCC4)cc3)cs2)CC1] | ACV-85 | ACV-3-019 |
| 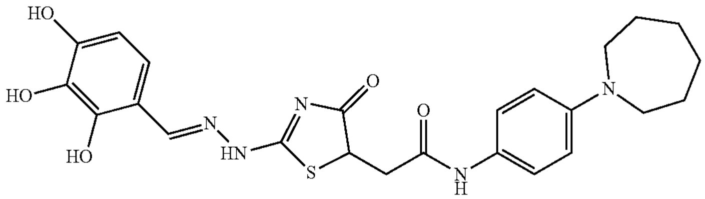 [SMILES: O=C(CC1SC(N/N=C/c2ccc(O)c(O)c2O)=NC1=O)Nc1ccc(N2CCCCCC2)cc1] | ACV-86 | ACV-3-024 |
| 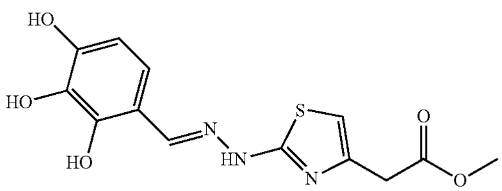 [SMILES: COC(=O)Cc1csc(N/N=C/c2ccc(O)c(O)c2O)n1] | ACV-87 | ACV-3-027 |
| 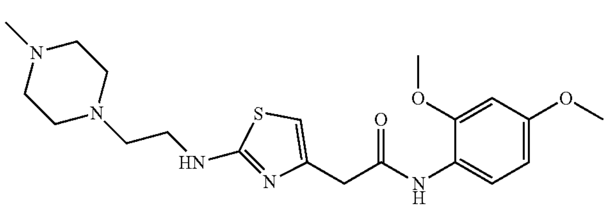 | ACV-88 | ACV-3-042 |

TABLE 1-continued
Exemplary Compounds
| Structure | Compound Name | Alternate name |
|---|---|---|
| 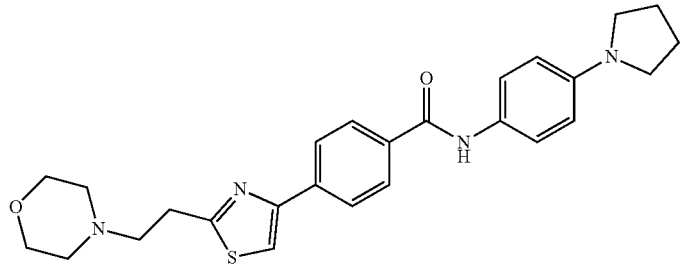 [SMILES: O=C(Nc1ccc(N2CCCC2)cc1)c1ccc(-c2csc(CCN3CCOCC3)n2)cc1] | ACV-89 | ACV-3-048 |
| 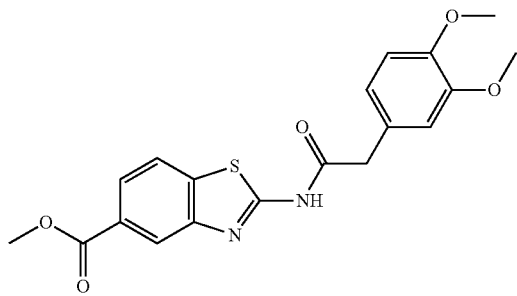 | ACV-90 | ACV-3-060 |
| 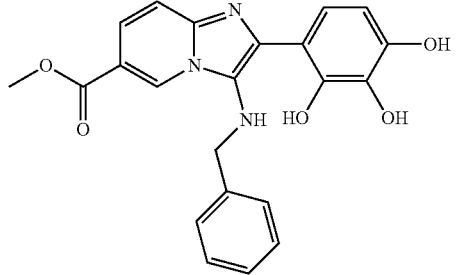 [SMILES: COC(=O)c1ccc2nc(-c3ccc(O)c(O)c3O)c(NCc3ccccc3)n2c1] | ACV-91 | ACV-3-061 |
| 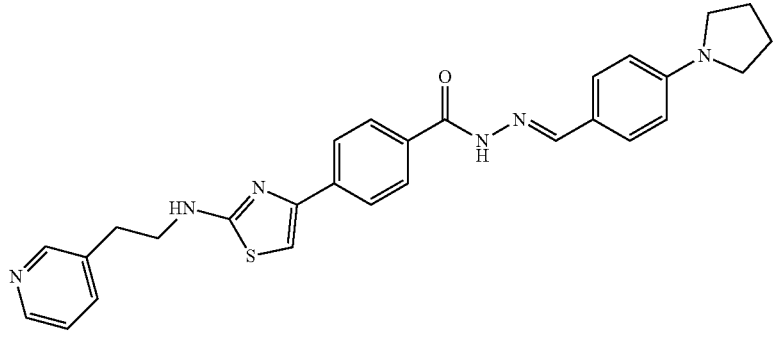 [SMILES: O=C(N/N=C/c1ccc(N2CCCC2)cc1)c1ccc(-c2csc(NCCc3cccnc3)n2)cc1] | ACV-92 | ACV-3-074 |
| 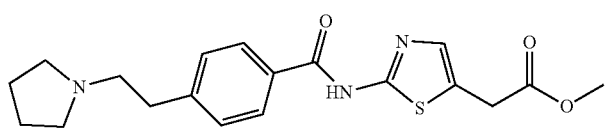 [SMILES: COC(=O)Cc1cnc(NC(=O)c2ccc(CCN3CCCC3)cc2)s1] | ACV-93 | ACV-2-144 |

TABLE 1-continued
Exemplary Compounds
| Structure | Compound Name | Alternate name |
|---|---|---|
| 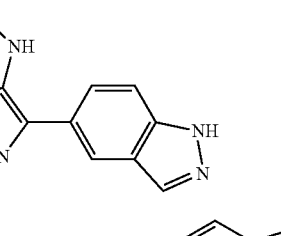 | ACV-94 | ACV-3-073 |
| 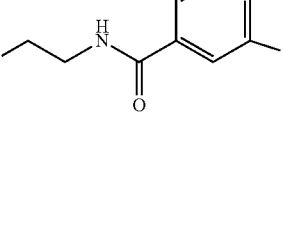 | ACV-95 | ACV-3-090 |
| 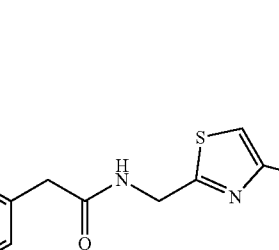 | ACV-96 | ACV-3-096 |
| 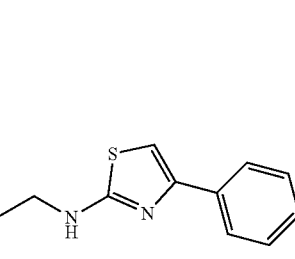 | ACV-97 | ACV-3-104 |
| 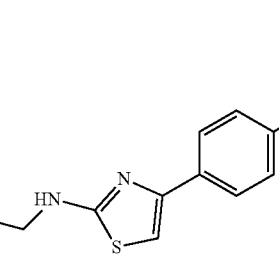 | ACV-98 | ACV-3-106 |
| 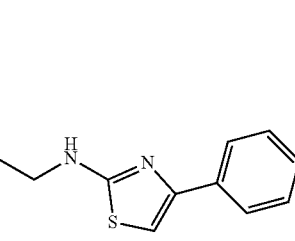 | ACV-99 | ACV-3-107 |

TABLE 1-continued

Exemplary Compounds

| Structure | Compound Name | Alternate name |
|---|---|---|
| 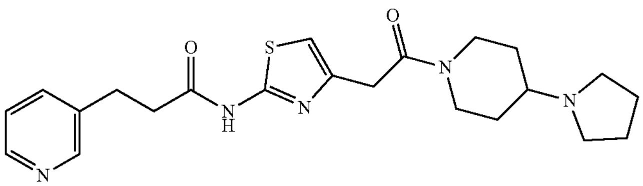 [SMILES: O=C(CCc1cccnc1)Nc1nc(CC(=O)N2CCC(N3CCCC3)CC2)cs1] | ACV-100 | ACV-3-122 |
| 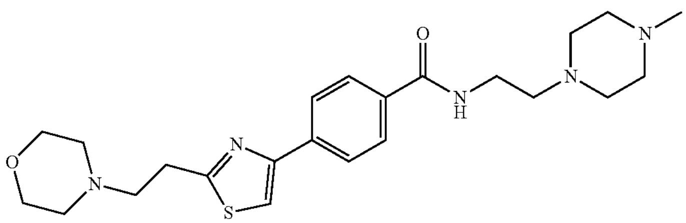 [SMILES: CN1CCN(CCNC(=O)c2ccc(-c3csc(CCN4CCOCC4)n3)cc2)CC1] | ACV-101 | ACV-3-123 |
| 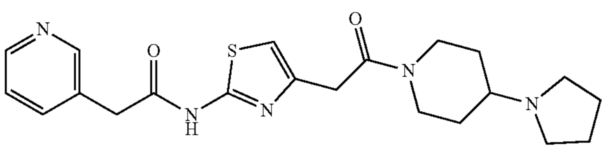 [SMILES: O=C(Cc1cccnc1)Nc1nc(CC(=O)N2CCC(N3CCCC3)CC2)cs1] | ACV-102 | ACV-3-124 |
| 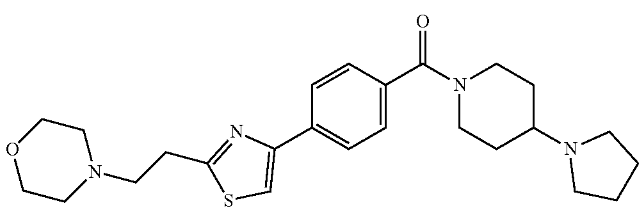 [SMILES: O=C(c1ccc(-c2csc(CCN3CCOCC3)n2)cc1)N1CCC(N2CCCC2)CC1] | ACV-103 | ACV-3-126 |
| 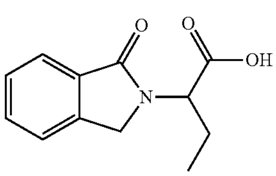 [SMILES: CCC(C(=O)O)N1Cc2ccccc2C1=O] | ACV-104 | 076 |
| 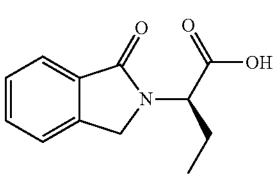 [SMILES: CC[C@H](C(=O)O)N1Cc2ccccc2C1=O] | ACV-105 | ACV-1-037 |
| 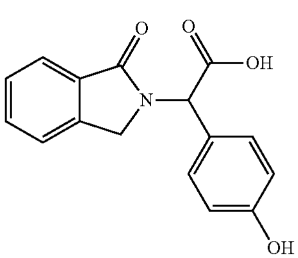 [SMILES: O=C(O)C(c1ccc(O)cc1)N1Cc2ccccc2C1=O] | ACV-106 | |

TABLE 1-continued

Exemplary Compounds

| Structure | Compound Name | Alternate name |
|---|---|---|
| [structure: 2-(1-oxoisoindolin-2-yl)-3-(4-hydroxyphenyl)propanoic acid] | ACV-107 | 295 |
| [structure: (S)-2-(1-oxoisoindolin-2-yl)-2-phenylacetic acid] | ACV-108 | ACV-1-056 |
| [structure: 2-(1-oxoisoindolin-2-yl)-3-phenylpropanoic acid] | ACV-109 | 017 |
| [structure: 2-(1-oxoisoindolin-2-yl)-3-(benzylthio)propanoic acid] | ACV-110 | 821 |

TABLE 2

Other Structures

I [structure: 2-(furan-2-yl)-N'-((4,6-dichloropyrimidin-5-yl)methylene)quinoline-4-carbohydrazide] V56

[structure: thiazolidinone derivative with vanillin hydrazone and 2,3-dichloroanilide] JQ-1

TABLE 2-continued

Other Structures

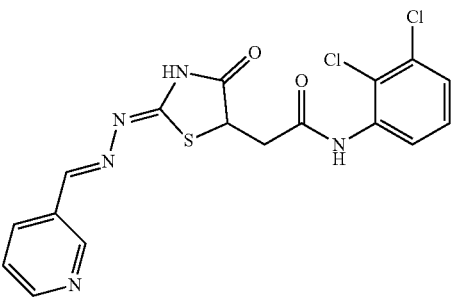 [SMILES: O=C(CC1S/C(=N\N=C\c2cccnc2)NC1=O)Nc1cccc(Cl)c1Cl]

JQIII-263-A

II. Pharmaceutical Compositions

In certain embodiments, the present invention provides pharmaceutical compositions comprising a compound of one of Formulas I-IX and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily.

In preferred embodiments, the active compound will be administered once daily.

The patient receiving this treatment is any animal in need, including primates, in particular humans, and other mammals such as equines, cattle, swine and sheep; and poultry and pets in general.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I or Formula II. As another example, the salt may comprise less than one inorganic or organic acid molecule per molecule of base, such as two molecules of compound of Formula I or Formula II per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

III. Uses of Compounds and Compositions

In certain aspects, the invention provides methods of treating or preventing a disease or condition, comprising administering to a subject a compound of one of Formulas I-IX, e.g., in a therapeutically effective amount or a composition comprising a compound of one of Formulas I-IX.

In some embodiments, the disease is cancer. In some embodiments, the cancer is breast cancer, prostate cancer, oral squamous carcinoma, colorectal cancer, squamous cell carcinomas, neuroblastoma, bladder tumors, leukemia, non-Hodgkin's lymphoma, and solid and hematologic malignancies.

In certain embodiments, the cancer is a solid tumor. The subject is generally one who has been diagnosed as having a cancerous tumor or one who has been previously treated for a cancerous tumor (e.g., where the tumor has been previously removed by surgery). The cancerous tumor may be a primary tumor and/or a secondary (e.g., metastatic) tumor.

In certain embodiments, the subject is a mammal, e.g., a human.

In certain embodiments, the invention provides methods of inhibiting proliferation of a cancerous cell comprising contacting a cancerous cell with an effective amount of a compound of one of Formulas I-IX.

The invention also provides methods of inhibiting proliferation of a cancer cell, comprising contacting a cancer cell with a compound of one of Formulas I-IX or a composition comprising a compound of one of Formulas I-IX.

The invention also provides methods of inhibiting CBX, comprising contacting a cell with a compound of one of Formulas I-IX. Such methods may be performed in vivo or in vitro.

IV. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —$OCF_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

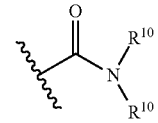

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

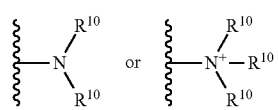

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

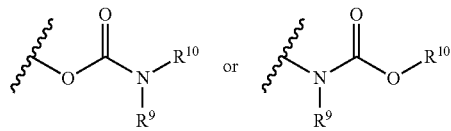

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $-OCO_2-R^{10}$, wherein $R^{10}$ represents a hydrocarbyl group.

The term "carboxy", as used herein, refers to a group represented by the formula $-CO_2H$.

The term "ester", as used herein, refers to a group $-C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, benzimidazole, quinoline, isoquinoline, quinoxaline, quinazoline, indole, isoindole, indazole, benzoxazole, pyrazine, pyridazine, purine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

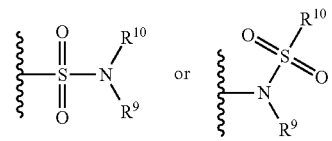

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

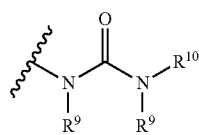

wherein R⁹ and R¹⁰ independently represent hydrogen or a hydrocarbyl, such as alkyl, or either occurrence of R⁹ taken together with R¹⁰ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of one of Formulas I-IX). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of one of Formulas I-IX in a formulation represented above can be replaced with the corresponding suitable prodrug, e.g., wherein a hydroxyl in the parent compound is presented as an ester or a carbonate or carboxylic acid present in the parent compound is presented as an ester.

EXAMPLES

Examples of compounds of Formulas I-IX or pharmaceutically acceptable salts thereof having useful biological activity are listed above in Table 1. The preparation of these compounds can be realized by one of skilled in the art of organic synthesis using known techniques and methodology.

Example 1: Chemical Syntheses

A general procedure used in the methods to prepare various compounds of the invention are described below.

Scheme 1

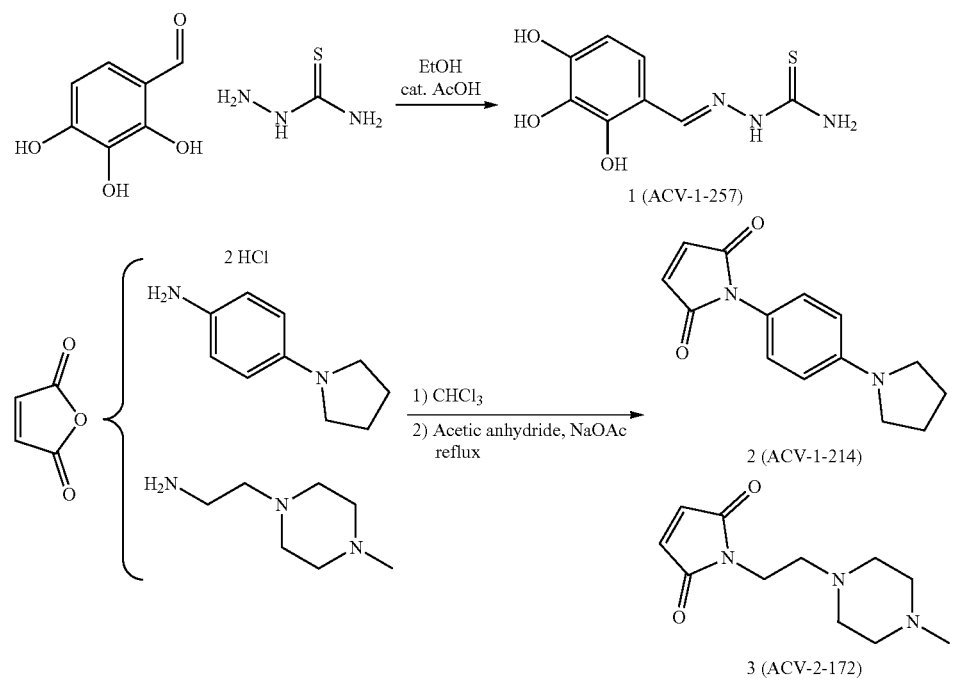

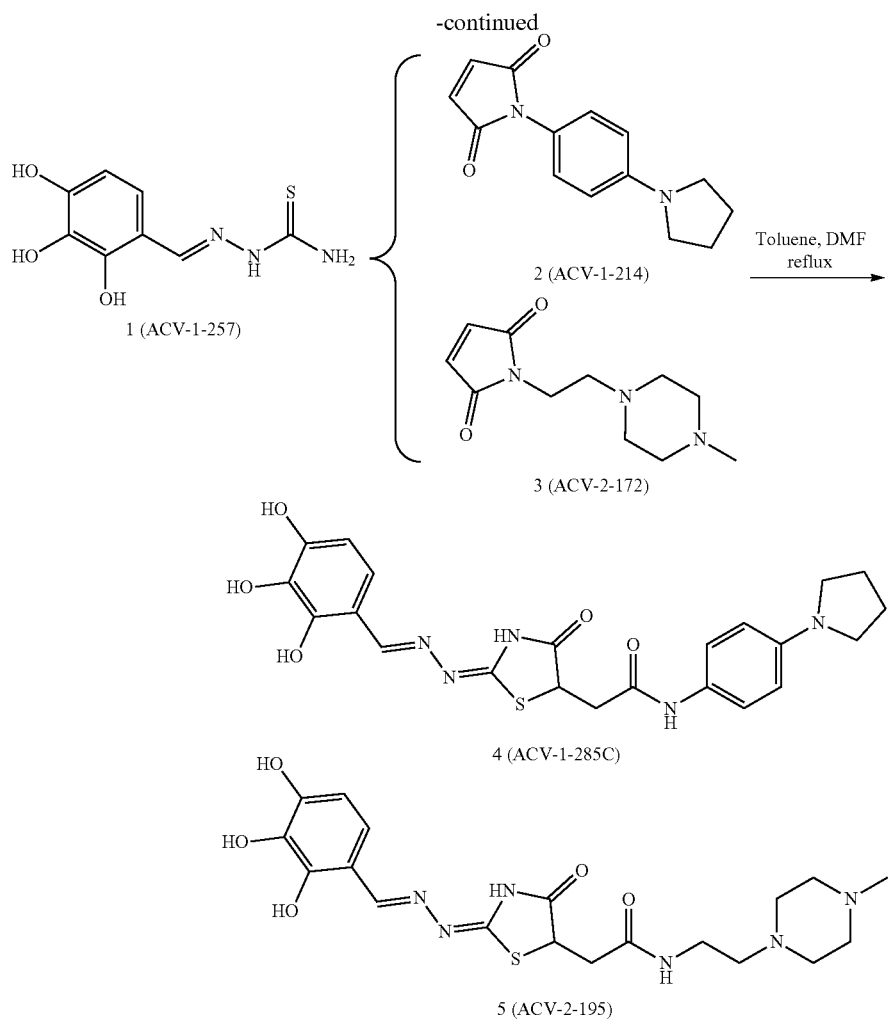

Synthesis of ACV-1-258C/ACV-2-195

(1) 2-(2,3,4-trihydroxybenzylidene)hydrazine-1-carbothioamide 2,3,4-trihydroxybenzaldehyde (338.3 mg, 2.20 mmol) and thiosemicarbazide (200.3 mg, 2.20 mmol) were combined and suspended in EtOH (4.4 mL) and a few drops of acetic acid were then added. The reaction was stirred at room temperature for 45 minutes. The reaction was then filtered and the precipitate was washed with hexanes to afford 1 as a white powder. MS: m/z (M+1)$^+$: 228.24. $^1$H NMR (400 MHz, METHANOL-d$_4$) δ ppm 6.42 (d, J=8.61 Hz, 1H) 6.88 (d, J=8.61 Hz, 1H) 8.13 (s, 1H).

(2) 1-(4-(pyrrolidin-1-yl)phenyl)-1H-pyrrole-2,5-dione

Maleic anhydride (121.0 mg, 1.23 mmol) was dissolved in CHCl3 (6.5 mL) and 4-(pyrrolidin-1-yl)aniline dihydrochloride (199.3 mg, 1.23 mmol) was then added. The reaction was stirred at room temperature for 3 hours. The reaction was filtered and the solid was resuspended in acetic anhydride (6 mL). To the reaction was then added sodium acetate (103 mg). The reaction was heated to reflux under N2 for 2 hours. After reflux, H2O (20 mL) was added to the reaction. A black precipitate was formed and the reaction was filtered to afford 2 as a dark brown/black solid. MS: m/z (M+1)$^+$: 243.59. $^1$H NMR (400 MHz, METHANOL-d$_4$) δ ppm 2.04 (dt, J=6.65, 3.33 Hz, 4H) 6.59-6.64 (m, 2H) 6.90 (s, 2H) 7.02-7.07 (m, 2H).

(3) 1-(2-(4-methylpiperazin-1-yl)ethyl)-1H-pyrrole-2,5-dione

Maleic anhydride (501.9 mg, 5.11 mmol) was dissolved in CHCl3 (25 mL) and 2-(4-methylpiperazin-1-yl)ethan-1-amine (767 μL, 5.11 mmol) was then added. The reaction was stirred at room temperature for 2 hours. The solvent was removed in vacuo and the crude solid was resuspended in acetic anhydride (25 mL). To the reaction was then added sodium acetate (250 mg). The reaction was heated to reflux under N2 for 3 hours. After reflux, the reaction was cooled to room temperature and washed with hexanes to obtain 3 (crude) as a dark brown/black oil. MS: m/z (M+1)$^+$: 224.28

(4) 2-(4-oxo-2-((2,3,4-trihydroxybenzylidene)hydrazono)thiazolidin-5-yl)-N-(4-(pyrrolidin-1-yl)phenyl)acetamide 2 (50.0 mg, 0.21 mmol) and 1 (47.0 mg, 0.21 mmol) were combined and dissolved in DMSO (1 mL). The reaction was heated at 80° C. overnight. The reaction was then purified via HPLC to afford the pure product 4 (8.8 mg). MS: m/z (M+1)⁺: 470.37. ¹H NMR (500 MHz, DMSO-$d_6$) δ ppm 2.28 (s, 3H) 2.37 (br t, J=6.71 Hz, 2H) 2.62-2.72 (m, 1H) 2.98 (dd, J=16.17, 3.66 Hz, 1H) 3.18 (q, J=6.51 Hz, 2H) 4.38 (dd, J=10.07, 3.66 Hz, 1H) 6.40 (d, J=8.24 Hz, 1H) 6.83 (d, J=8.54 Hz, 1H) 8.03 (br t, J=5.49 Hz, 1H) 8.15 (s, 1H) 8.41-8.47 (m, 1H) 11.18 (br s, 1H).

(5) N-(2-(4-methylpiperazin-1-yl)ethyl)-2-(4-oxo-2-((2,3,4-trihydroxybenzylidene)hydrazono)thiazolidin-5-yl)acetamide 3 (22.5 mg, 0.1 mmol) and 1 (22.8 mg, 0.1 mmol) were combined and dissolved in Toluene (0.5 mL) and DMF (0.5 mL). The reaction was heated to reflux for 10 minutes in the microwave. The crude was purified via HPLC to afford the pure product 5 (6.0 mg). MS: m/z (M+1)⁺: 451.35. ¹H NMR (500 MHz, DMSO-$d_6$) δ ppm 1.15 (s, 1H) 1.23 (s, 1H) 1.93 (dt, J=6.48, 3.32 Hz, 4H) 2.73 (d, J=0.61 Hz, 1H) 2.84-2.91 (m, 1H) 3.14-3.23 (m, 5H) 3.29 (s, 3H) 4.48 (br dd, J=10.22, 3.20 Hz, 1H) 6.39 (d, J=8.54 Hz, 1H) 6.48 (d, J=8.85 Hz, 2H) 6.83 (d, J=8.54 Hz, 1H) 7.32-7.39 (m, 2H) 8.46 (s, 1H) 8.58 (s, 1H) 9.53 (s, 1H) 9.81 (s, 1H) 11.23 (s, 1H) 12.00 (s, 1H).

Synthesis of ACV-1-204

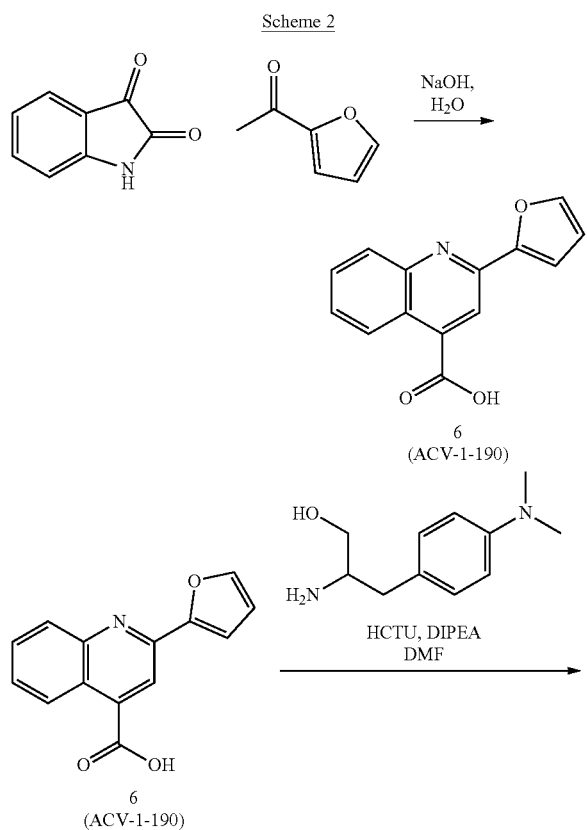

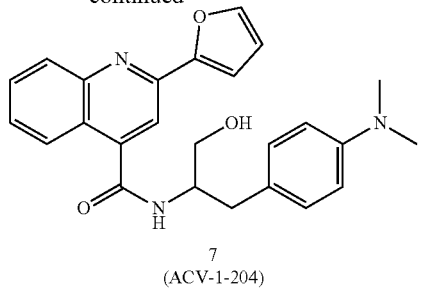

7
(ACV-1-204)

(6) 2-(furan-2-yl)quinoline-4-carboxylic acid

Isatin (249.8 mg, 1.70 mmol) and NaOH (341.6 mg, 8.50 mmol) were combined and suspended in H2O (3.5 mL) and heated to 50° C. When the solution became a clear, 2-acetylfuran (170.4 µL, 1.70 mmol) was added and the reaction was stirred at 50° C. overnight. The reaction was then filtered to afford 6. MS: m/z (M+1)⁺: 240.55. ¹H NMR (600 MHz, METHANOL-$d_4$) δ ppm 6.67 (dd, J=3.23, 1.47 Hz, 1H) 7.33 (d, J=3.52 Hz, 1H) 7.55 (t, J=7.63 Hz, 1H) 7.72 (t, J=7.63 Hz, 1H) 7.76 (d, J=1.76 Hz, 1H) 7.97 (s, 1H) 8.05 (d, J=8.22 Hz, 1H) 8.36 (d, J=8.22 Hz, 1H).

(7) N-(1-(4-(dimethylamino)phenyl)-3-hydroxypropan-2-yl)-2-(furan-2-yl)quinoline-4-carboxamide 6 (61.7 mg, 0.26 mmol) and HCTU (213.3 mg, 0.52 mmol) were combined and dissolved in DMF (1 mL). DIPEA (224.3 µL, 1.29 mmol) was then added and the reaction was stirred at room temperature for a few minutes at which point a solution of 2-amino-3-(4-(dimethylamino)phenyl)propan-1-ol (50.0 mg, 0.26 mmol) in DMF (0.3 mL) was added. The reaction was stirred at room temperature for 2 hours. The reaction was diluted with EtOAc (40 mL) and then washed with H2O (5 mL) and brine (5 mL). The organic layer was collected, dried over Na2SO4, filtered and concentrated to dryness. The crude material was then purified via silica gel column chromatography (0-15% MeOH:DCM) to afford the pure product 7 (2.3 mg). MS: m/z (M+1)⁺: 416.69. ¹H NMR (400 MHz, METHANOL-$d_4$) δ ppm 2.66 (dd, J=13.69, 10.17 Hz, 1H) 2.81 (s, 1H) 2.89 (s, 1H) 2.94 (s, 6H) 2.98-3.04 (m, 1H) 3.74 (dd, J=14.28, 5.67 Hz, 2H) 4.47-4.57 (m, 1H) 6.69 (dd, J=3.52, 1.96 Hz, 1H) 6.78-6.81 (m, 2H) 7.15-7.20 (m, 2H) 7.31-7.35 (m, 1H) 7.40-7.45 (m, 1H) 7.56 (d, J=7.43 Hz, 1H) 7.73 (ddd, J=8.51, 6.95, 1.37 Hz, 1H) 7.79 (dd, J=1.96, 0.78 Hz, 1H) 7.80 (s, 1H) 7.90 (s, 1H) 8.04 (d, J=8.22 Hz, 1H).

Synthesis of ACV-2-112

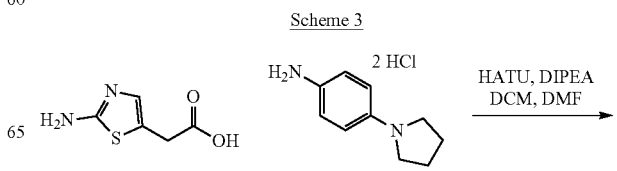

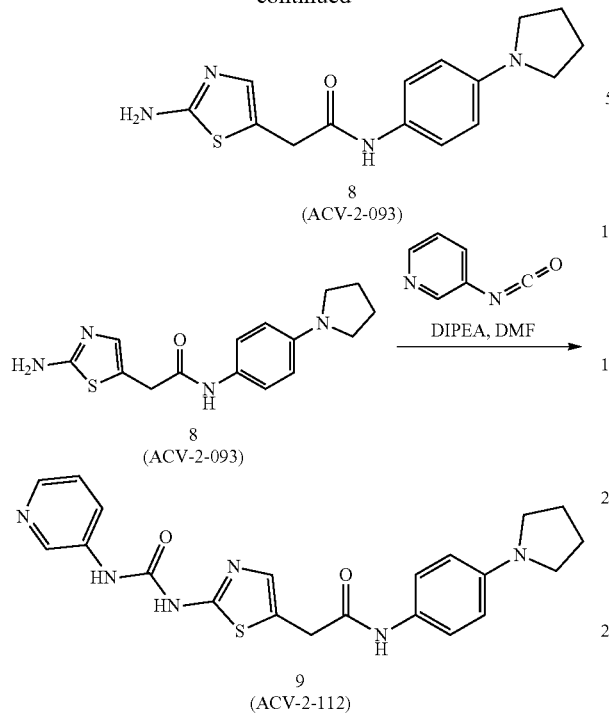

(8) 2-(2-aminothiazol-5-yl)-N-(4-(pyrrolidin-1-yl)phenyl)acetamide 2-aminothiazole-5-acetic acid (50.5 mg, 0.32 mmol) was added to a solution of the 4-(pyrrolidin-1-yl)aniline dihydrochloride (151.0 mg, 0.64 mmol) and DIPEA (334.0 μL, 1.92 mmol) in DCM (1 mL). DMF (1 mL) was added to the reaction followed by HATU (146.7 mg, 0.38 mmol) and the reaction was stirred at room temperature for 2 hours. The reaction was diluted with DCM (10 mL) and washed with H2O and brine (10 mL each). The organic layer was dried over Na2SO4, filtered and concentrated to dryness. The crude material was purified via silica gel column chromatography (0-15% MeOH:DCM) to afford 8. MS: m/z $(M+1)^+$: 303.24

(9) 2-(2-(3-(pyridin-3-yl)ureido)thiazol-5-yl)-N-(4-(pyrrolidin-1-yl)phenyl)acetamide 8 (10.0 mg, 0.033 mmol) was dissolved in DMF (0.66 mL). To the reaction was then added DIPEA (28.8 μL, 0.165 mmol) followed by the pyridine-3-isocyanate (12.5 mg, 0.104 mmol). The reaction was stirred at room temperature for 3 hours. The crude reaction was purified via HPLC to afford pure 9 (8.5 mg). MS: m/z $(M+1)^+$: 423.25

Synthesis of ACV-3-142

Scheme 4

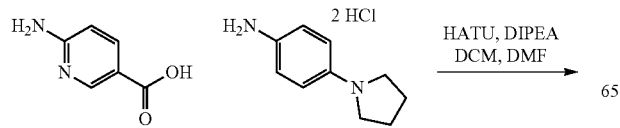

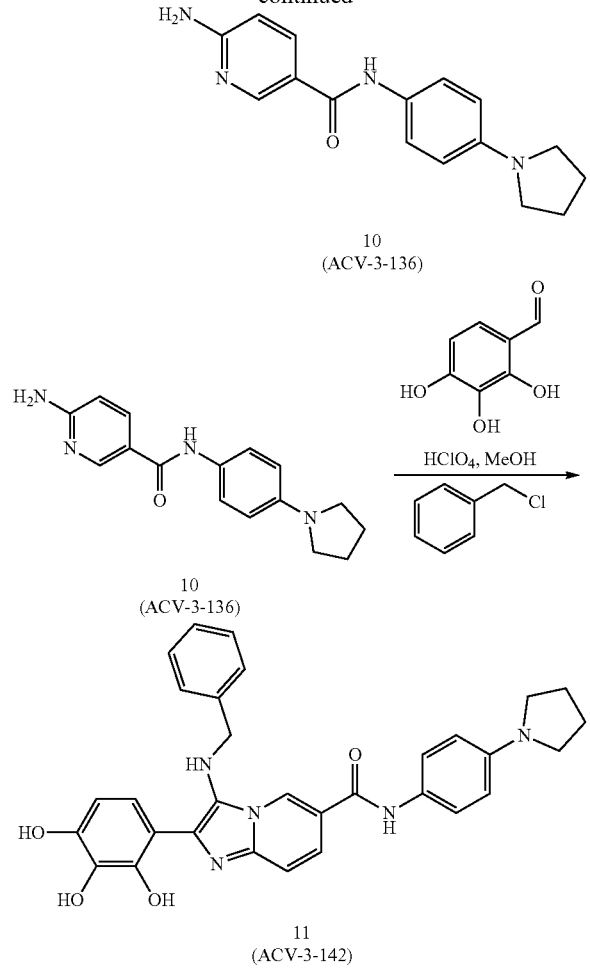

(10) 6-amino-N-(4-(pyrrolidin-1-yl)phenyl)nicotinamide 4-(pyrrolidin-1-yl)aniline dihydrochloride (263.0 mg, 1.12 mmol) was suspended in DCM (1.5 mL). DIPEA (650.7 μL, 3.74 mmol) was added to neutralize the HCl salts giving a clear brown solution. The solution was then transferred to a vessel containing 6-aminonicotinic acid (51.6 mg, 0.37 mmol). DMF (0.5 mL) was added followed by HATU (172.4 mg, 0.45 mmol) and the reaction was stirred at room temperature for 4 hours. The reaction was transferred to a separatory funnel and diluted with DCM then washed with H2O, saturated NaHCO3, and brine. The organic layer was collected, dried over Na2SO4, filtered, and concentrated to dryness. The crude material was purified via silica gel column chromatography (0-10% MeOH:DCM) to afford 10. MS: m/z $(M+1)^+$: 283.31. $^1$H NMR (500 MHz, METHANOL-$d_4$) δ ppm 1.31-1.38 (m, 3H) 2.00-2.07 (m, 4H) 3.24-3.30 (m, 4H) 6.48-6.72 (m, 3H) 7.39 (d, J=8.85 Hz, 2H) 7.97 (dd, J=8.85, 2.44 Hz, 1H) 8.52 (d, J=2.14 Hz, 1H).

(11) 3-(benzylamino)-N-(4-(pyrrolidin-1-yl)phenyl)-2-(2,3,4-trihydroxyphenyl)imidazo[1,2-a]pyridine-6-carboxamide 10 (20.9 mg, 0.07 mmol) and the 2,3,4-trihydroxybenzaldehyde (21.2 mg, 0.14 mmol) were combined and suspended in MeOH (1 mL). To the reaction was then added the benzyl isocyanide (12.7 μL, 0.10 mmol) followed by HClO4 (9.1 μL of a 1M solution in MeOH, 0.01 mmol). The reaction was stirred at room temperature overnight. The reaction was transferred to a separatory funnel and diluted with DCM then washed with H2O, saturated NaHCO3, and brine. The organic layer was collected, dried over Na2SO4, filtered, and concentrated to dryness. The crude material was purified via silica gel column chromatography (0-100% EtOAc:Hexanes) to afford 11 (2.2 mg). MS: m/z (M+1) 536.36. $^1$H NMR (500 MHz, METHANOL-$d_4$) δ ppm 2.00-2.06 (m, 4H) 3.28 (t, J=6.41 Hz, 4H) 4.11-4.17 (m, 2H) 6.47 (d, J=8.54 Hz, 1H) 6.59 (d, J=8.54 Hz, 2H) 7.13-7.20 (m, 3H) 7.21-7.26 (m, 2H) 7.42 (dd, J=8.54, 5.80 Hz, 3H) 7.48 (d, J=9.16 Hz, 1H) 7.69 (dd, J=9.31, 1.68 Hz, 1H) 8.65 (s, 1H).

Synthesis of CBX-08/CBX-09

(13) 3-(2,3,4-trihydroxyphenyl)-4,5-dihydro-1H-pyrazole-1-carbothioamide 12 (200 mg, 0.92 mmol) was suspended in EtOH and thiosemicarbazide (85.2 mg, 0.92 mmol) was added. The reaction was heated to 60° C. overnight. The crude reaction was purified via prep-HPLC to afford 13.

(14) 2-(4-oxo-2-(3-(2,3,4-trihydroxyphenyl)-4,5-dihydro-1H-pyrazol-1-yl)-4,5-dihydrothiazol-5-yl)-N-(4-(pyrrolidin-1-yl)phenyl)acetamide (CBX-08)

13 (50 mg, 0.20 mmol) and 2 (47.8 mg, 0.20 mmol) were combined and suspended in acetic acid. The reaction was heated to 125° C. for 4 hours. The crude material was purified via prep-HPLC to afford 14 as a brown solid (1 mg).

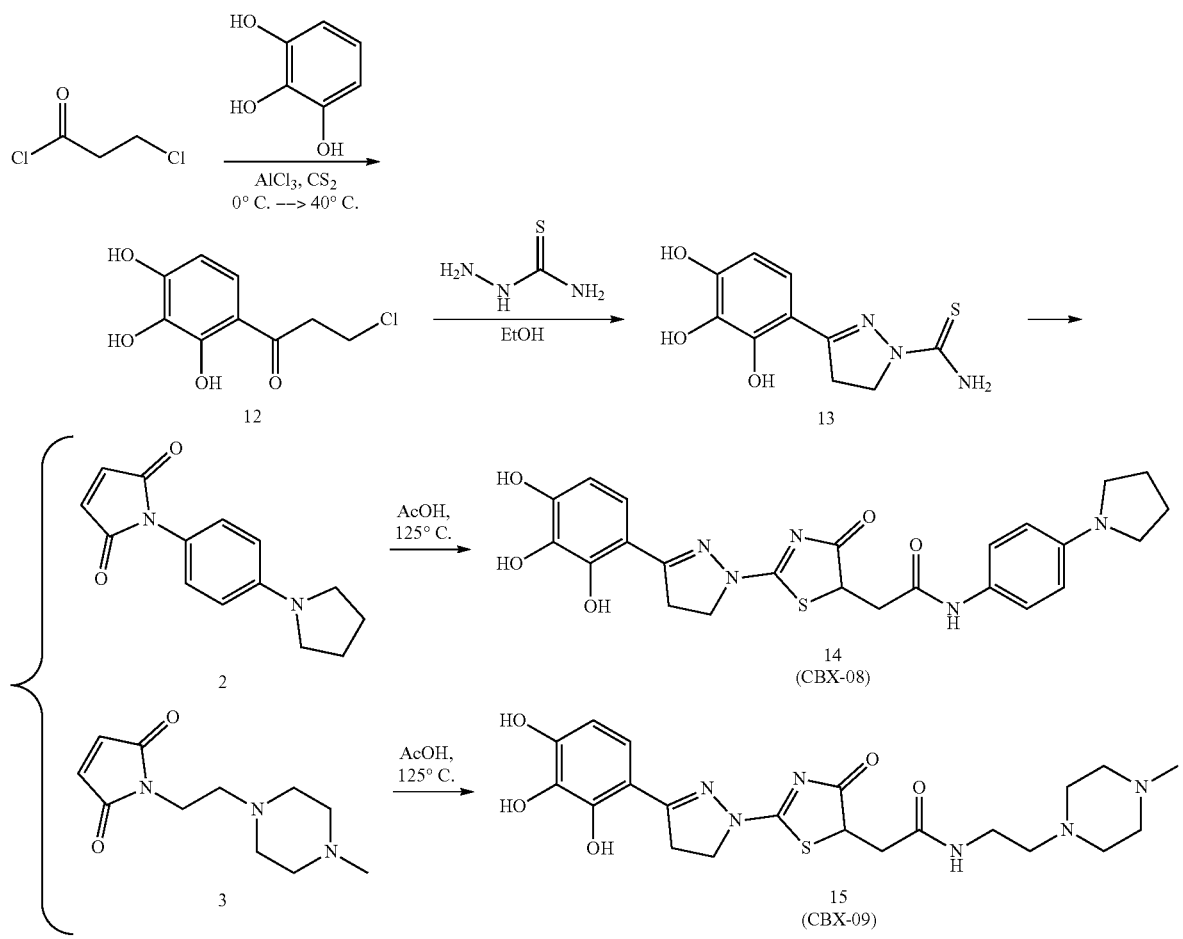

(12) 3-chloro-1-(2,3,4-trihydroxyphenyl)propan-1-one

Benzene-1,2,3-triol (1.94 g, 15.4 mmol) and 3-chloropropanoyl chloride (2 g, 15.4 mmol) were combined in CS$_2$. The reaction was placed in an ice bath and AlCl$_3$ (6.16 g, 46.2 mmol) was added. The reaction was stirred at 0° C. for 10 minutes and then heated to 40° C. overnight. The crude material was purified via Prep-TLC to afford 12 as a yellow solid.

(15) N-(2-(4-methylpiperazin-1-yl)ethyl)-2-(4-oxo-2-(3-(2,3,4-trihydroxyphenyl)-4,5-dihydro-1H-pyrazol-1-yl)-4,5-dihydrothiazol-5-yl)acetamide (CBX-09)

13 (50 mg, 0.20 mmol) and 3 (44.0 mg, 0.20 mmol) were combined and suspended in acetic acid. The reaction was heated to 125° C. for 4 hours. The crude material was purified via prep-HPLC to afford 15 as an off-white solid (4.8 mg).

Synthesis of exemplary compounds of Formula II
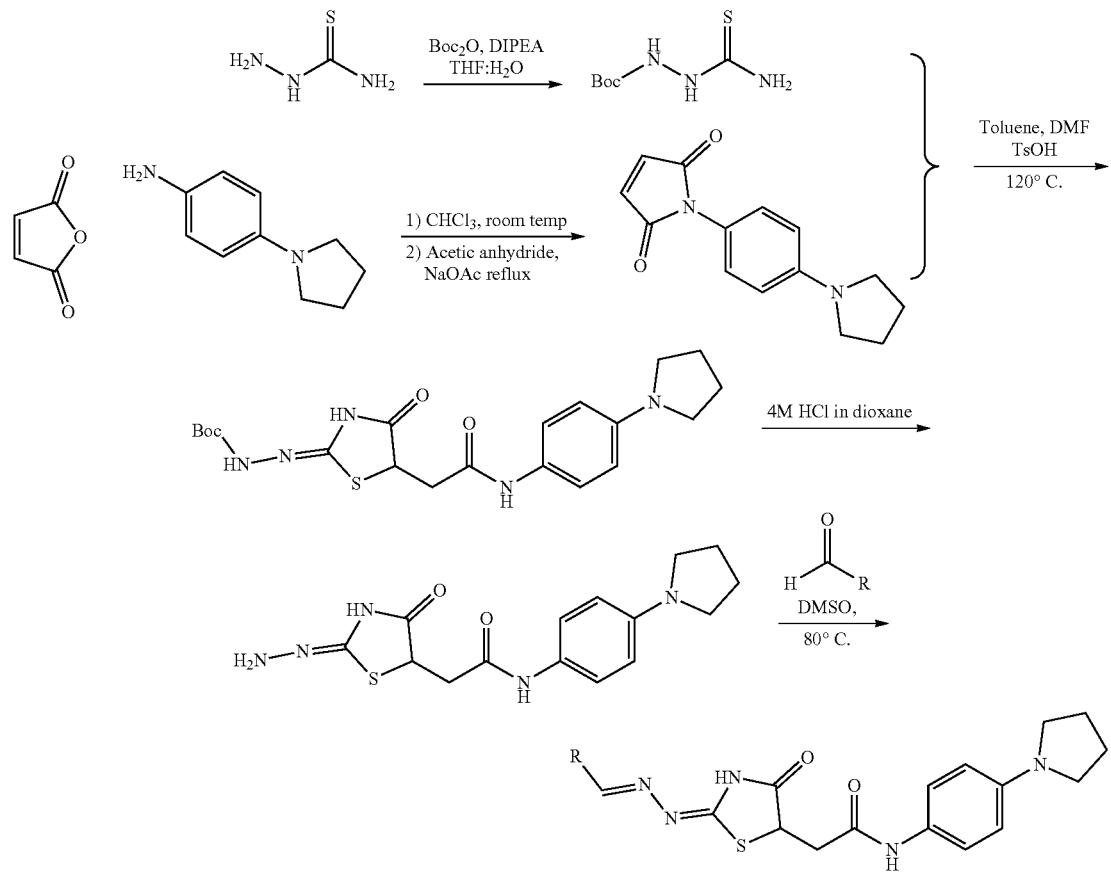
Alternate Synthesis of Exemplary Compounds of Formula II
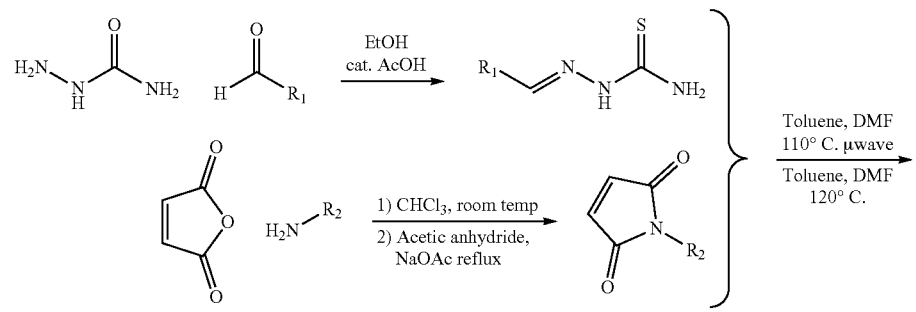
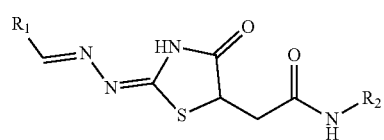

Synthesis of ACV-1-258A and ACV-1-258C
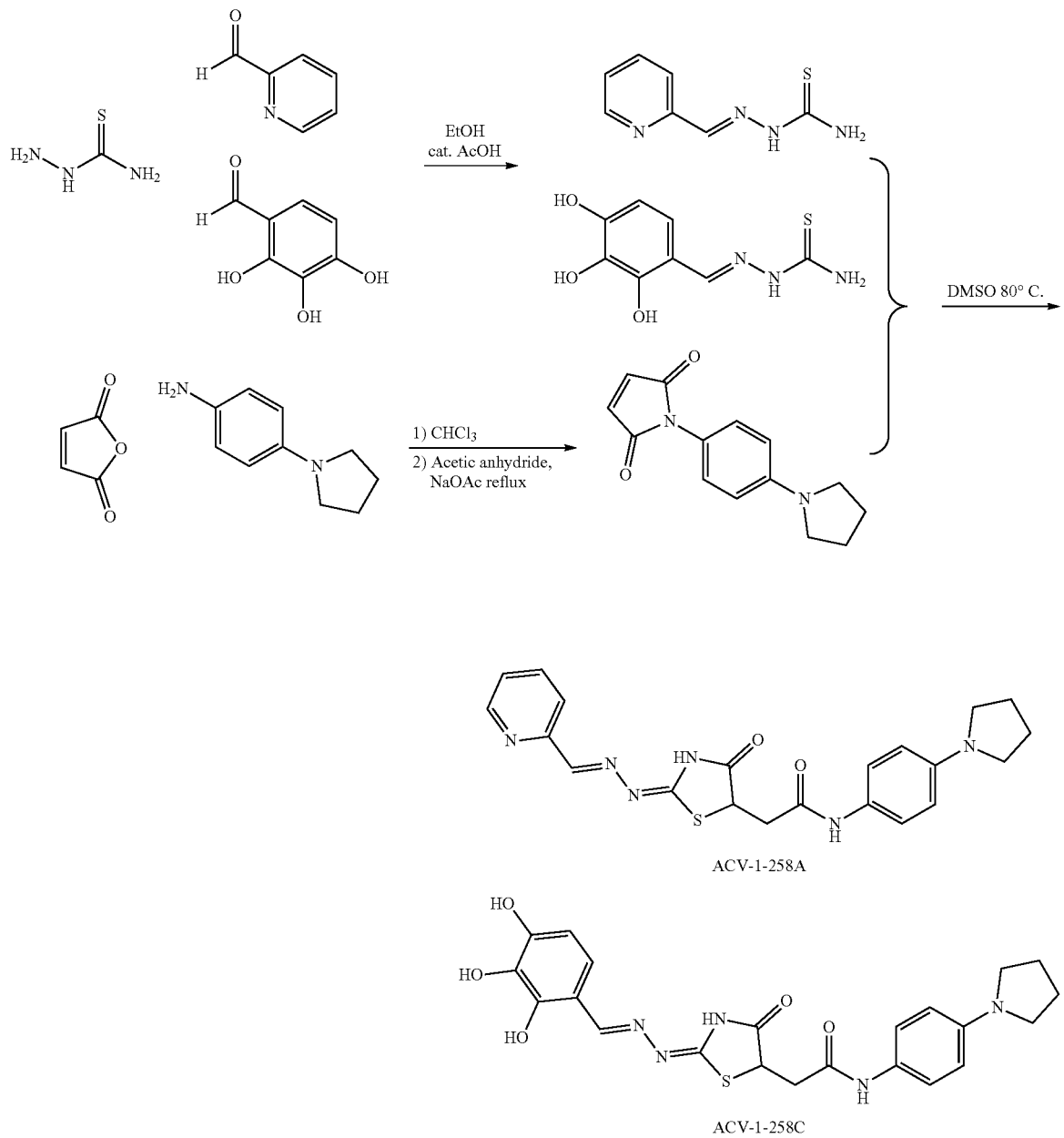
Synthesis of ACV-1-258A and ACV-1-242
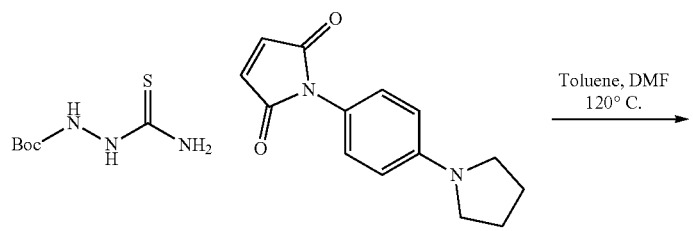

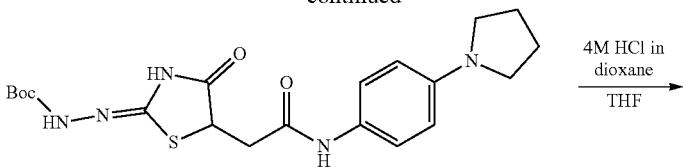
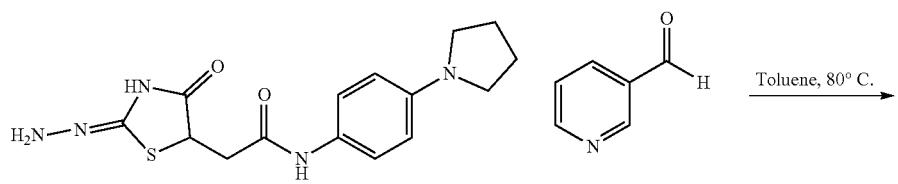
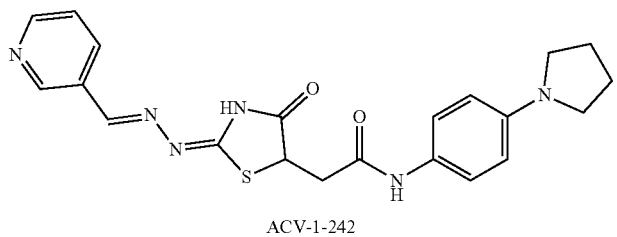
ACV-1-242
Synthesis of ACV-2-195 and ACV-2-204
Scheme 10
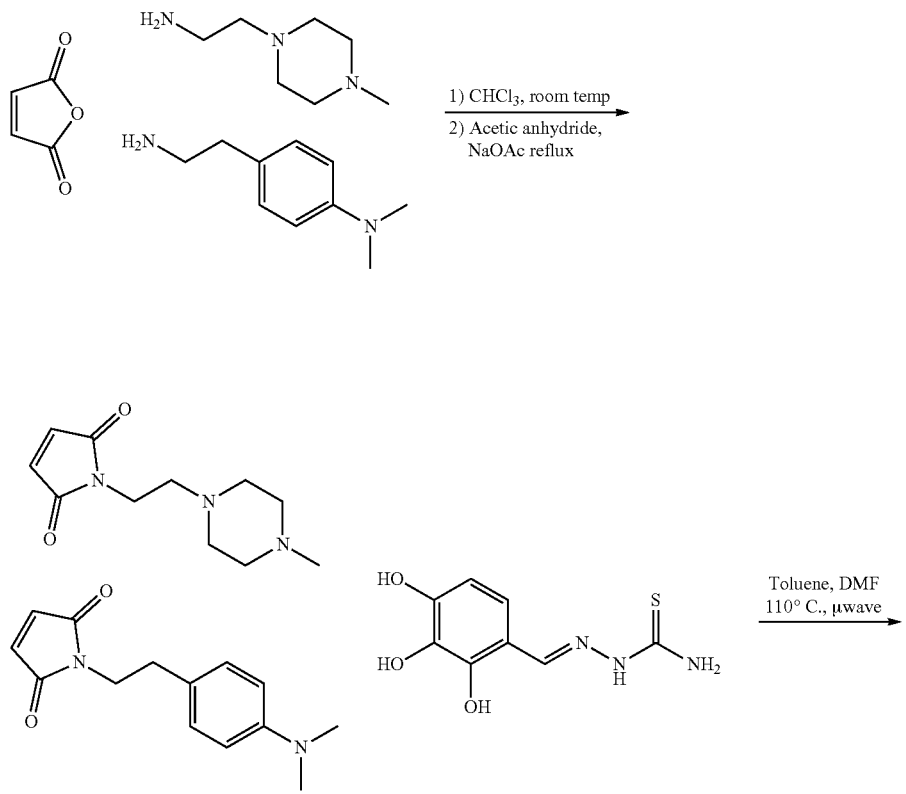

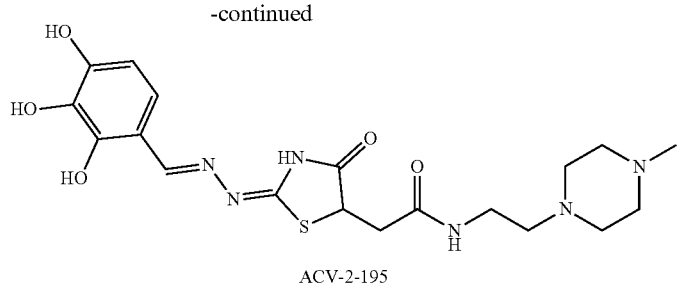
ACV-2-195
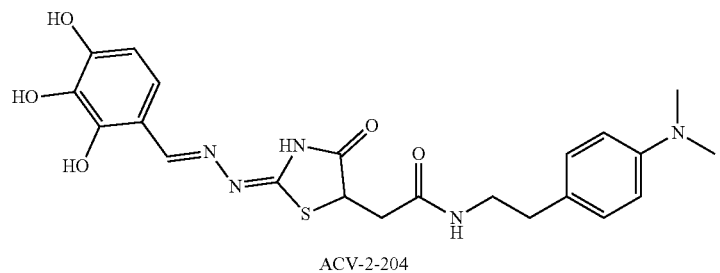
ACV-2-204
Synthesis of ACV-2-108, ACV-2-112, ACV-2-142, ACV-2-150, ACV-2-151, ACV-2-152, ACV-2-154, ACV-2-155, and ACV-2-156
Scheme 11
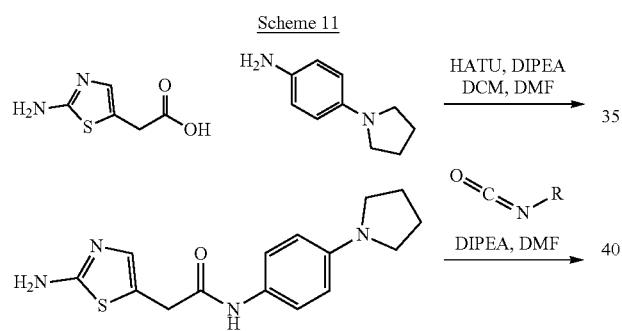
R =
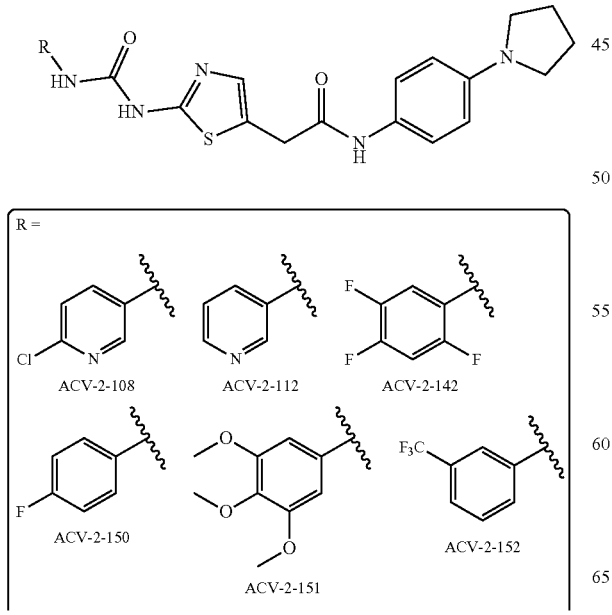
-continued
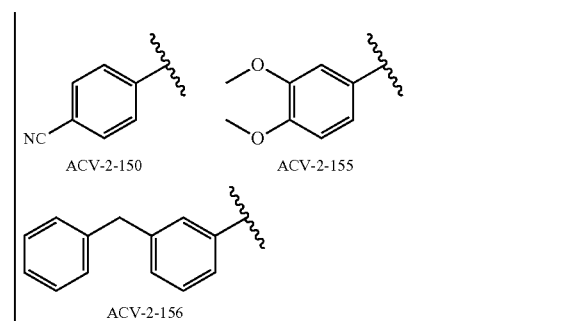
Synthesis of ACV-2-160
Scheme 12
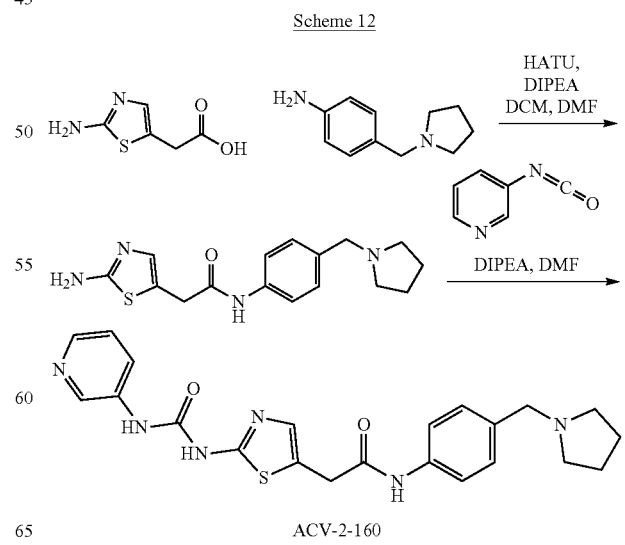

Synthesis of ACV-2-138 and ACV-2-147

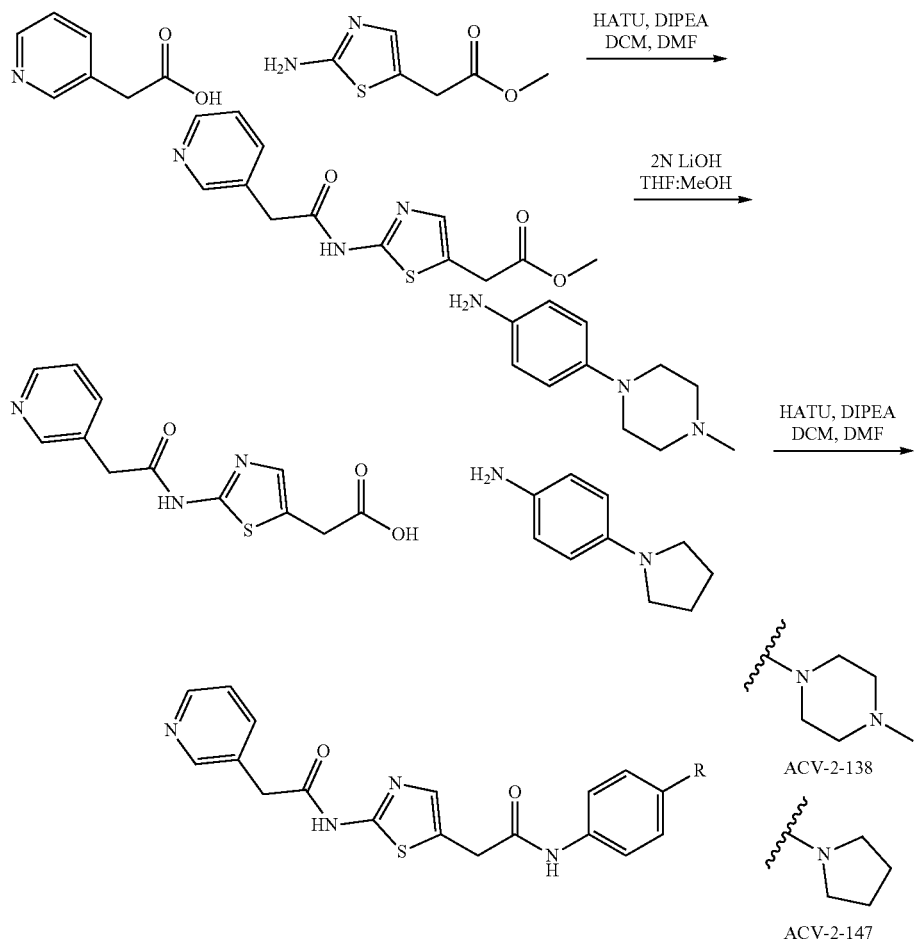

Example 2

A biochemical assay was developed based on nanoparticle AlphaScreen assay to monitor the binding of recombinant CBX chromodomain (CBX7) to a methylated peptide (H3K27me3).

The primary assay uses recombinant CBX chromodomain and synthetic, trimethylated H3 histone tail peptide. When CBX/histone tail-binding occurs, AlphaScreen beads are brought in close proximity, resulting in singlet molecular oxygen transfer and production of a luminescent signal. Assay positives inhibiting the binding interaction are therefore expected to prevent complex formation, diminishing signal intensity. The AlphaScreen technology features an anti-Stokes shift in detection: due to energy transfer between beads by singlet oxygen and internal chemical reactions within the acceptor bead, the emission wavelength is blue-shifted relative to the excitation wavelength, which is impossible in traditional fluorescent assays. The relatively long path length of 200 nm that singlet molecular oxygen can travel enables reporting on full protein complexes and not just single target binding. The assay proves highly amenable to miniaturization. Neither the small molecules being tested nor the target protein, CBX7, need to be chemically, conformationally, or behaviorally altered by tethering them to a surface or reporter that may decrease physiological relevance and beget screening artifacts. The primary assay monitors binding of the chromodomain of CBX7 to a histone tail containing a trimethylated lysine at K27, the biologically relevant interaction through which PRC binds to chromatin to repress transcription. This is a robust proximity-based assay that utilizes AlphaScreen technology (PerkinElmer). The assay consists of His6-CBX7 bound to a Ni$^{++}$ acceptor bead and the biotinylated histone tail bound to a streptavadin donor bead. Upon CBX7/H3K27me3 binding, the steptavidin bead comes into proximity with the Ni$^{++}$ bead to luminesce upon light excitation (680 nM; see below).

This assay was tested for Z' and reproducibility over time in smaller libraries before moving on to larger libraries. In total, the number of distinct compounds screened is greater than 250,000 across the libraries.

The protocol for the CBX7 AlphaScreen was as follows: a standard alpha buffer (50 mM HEPES, 150 mM NaCl, 0.1% w/v BSA, 0.01% w/v Tween20) at pH 8.0 and make up two stock solutions at 2× final concentration in the alpha buffer. Solution A contains Human His6-CBX7 used with biotinylated-H3K27me3 (residues 20-34), at 100 nM and 50 nM respectively. Solution B contains 20 nM streptavidin donor beads and 20 nM nickel acceptor beads. For 384 well assay formats, 10 uL of solution A is added to each well of the assay plate and the plate is spun at 1000 rpm for 30 seconds. 100 nL of experimental compounds from stock plates are delivered by robotic pin transfer using a Janus Workstation (PerkinElmer), allowing the compounds to interact with CBX7 binding prior to assay measurement, followed by another spin and an incubation room temperature. Finally, 10 uL of solution B is added to each well, the plate is spun again and then incubated at room temperature. AlphaScreen measurements are performed on an Envision 2104 (PerkinElmer) utilizing the manufacturer's protocol that has the correct excitation and emission wavelengths, cutoff filters, delay time, etc. A crosstalk calculation is also done through the Envision software to correct for luminescence for adjacent wells while reading the plate. The signal is then normalized to DMSO control wells on the compound plate prior to creation of the IC50 curves.

The assay reports on inhibition of binding with high fidelity (Z' of 0.88) in a dose-responsive manner. Assay positives from the primary screen were retested at 10-point dose response in the primary assay, to determine relative potencies and to screen for artifacts resulting from certain forms of assay interference. Additionally, all assay positives were studied for assay-specific activity (so-called "Alpha inhibition"), using a familiar, commercially available assay involving a biotinylated poly-histidine peptide which cross-links donor and acceptor beads. All compounds which scored in this assay were eliminated for non-selective activity (e.g. metal chelators, oxygen quenchers, biotin mimetics). From the libraries screened, we found a few different scaffolds that looked promising and brought them forward for further medicinal chemistry and structure activity relationship studies.

The assay performed well in the under high throughput conditions. Assay signal is stable for over 24 hours, although all measurements were made within 6 hours of the final addition of assay reagents. The assay proved robust over time. The Z' value, which is a measurement of the assay signal-to-noise taking into account variability in the positive and negative control values, was consistently above 0.8 for the duration of the screening. A value of 0.5 is generally considered acceptable to identify assay positives. Compound data between the two assay replicates were highly reproducible and correlative.

Figure 2:
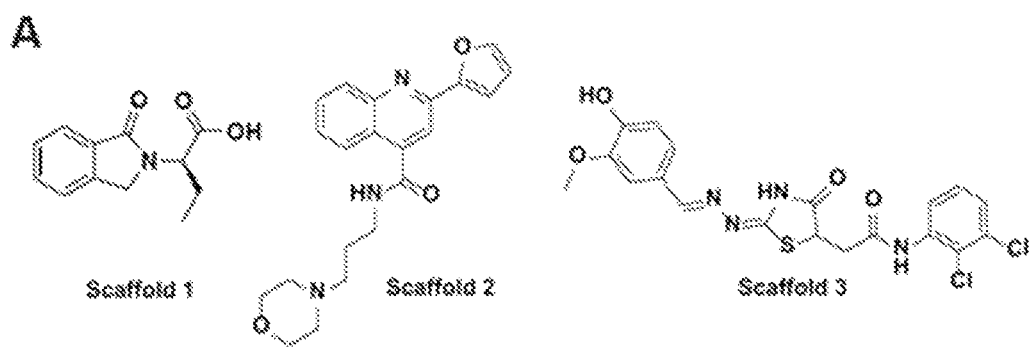
FIG. 2 includes three compounds identifying scaffolds selected for optimization.
Figure 3:
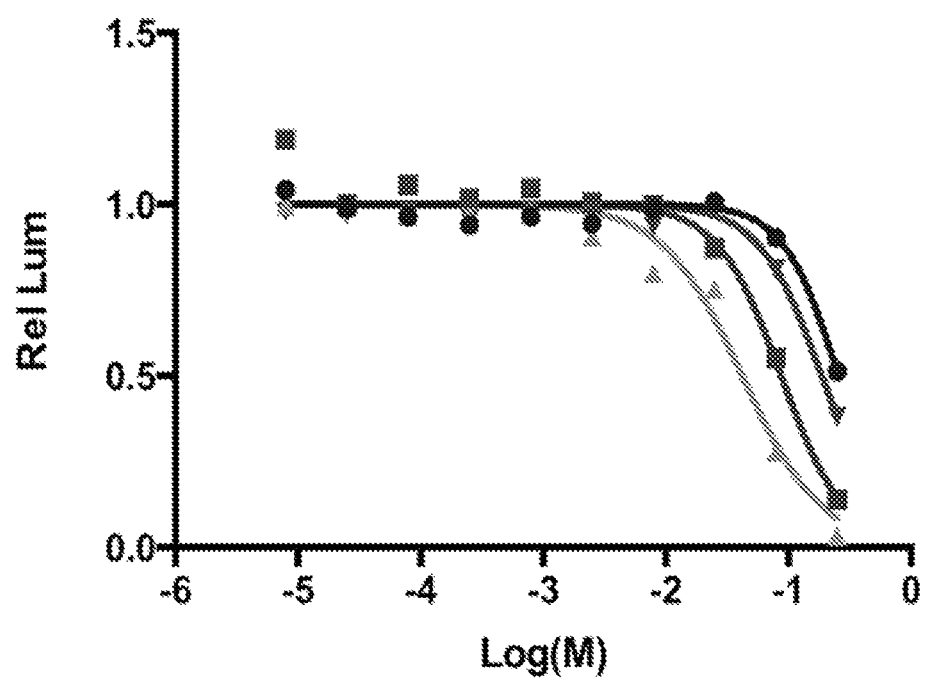
FIG. 3 is a plot of the results for the AlphaScreen assay for compounds ACV-106 (circle), ACV-105 (triangle), ACV-108 (square), ACV-110 (triangle).
Figure 4A:
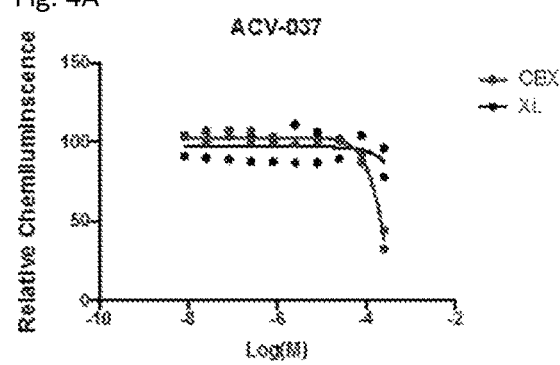
FIGS. 4A-4D are plots of the results for the AlphaScreen assay for ACV-037 (FIG. 4A), ACV-036 (FIG. 4B), ACV-038 (FIG. 4C), and ACV-044 (FIG. 4D).
Figure 4C:
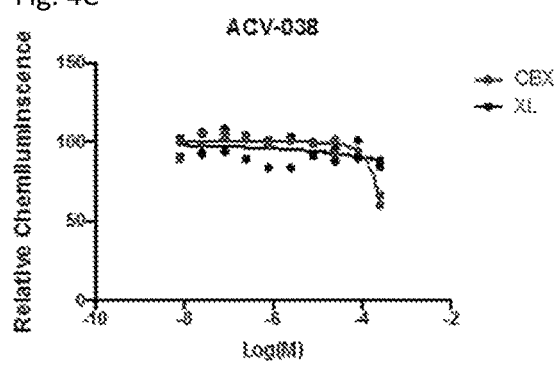
Figure 4B:
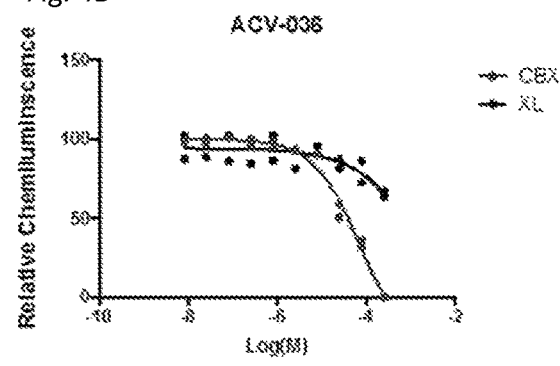
Figure 4D:
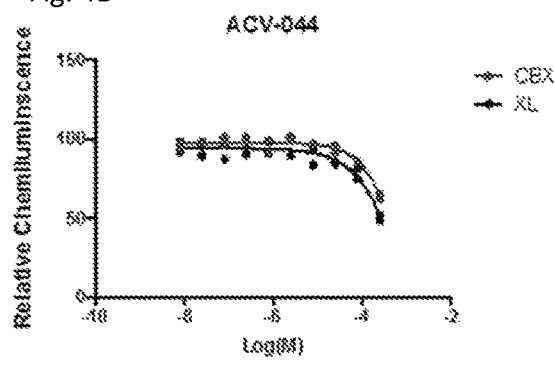
Figure 5A:
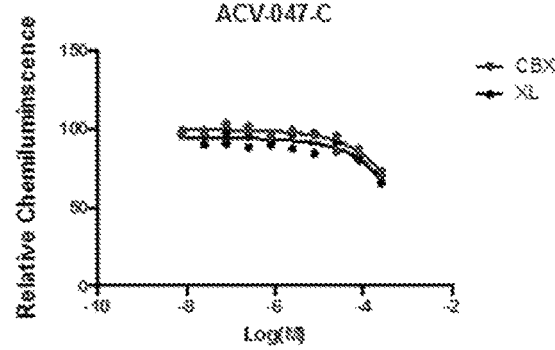
FIGS. 5A-5D are plots of the results for the AlphaScreen assay for ACV-47-C (FIG. 5A), ACV-047-E1 (FIG. 5B), ACV-047-D (FIG. 5C), and ACV-047-E2 (FIG. 5D).
Figure 5B:
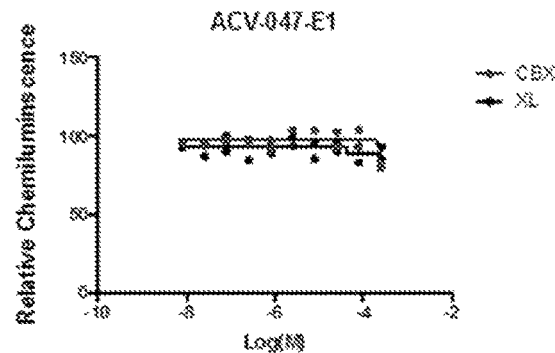
Figure 5C:
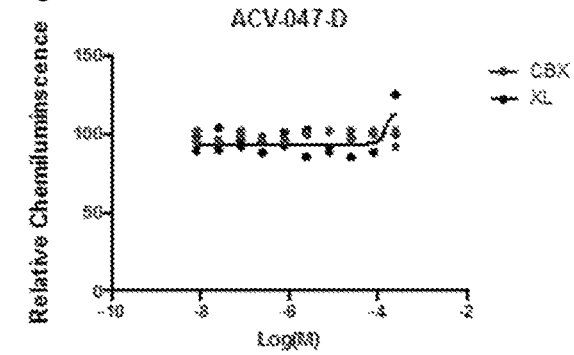
Figure 5D:
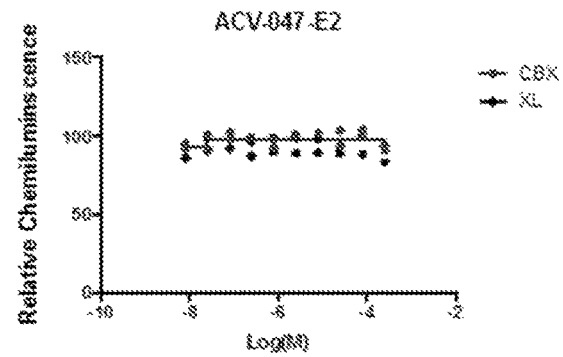
Figure 6:
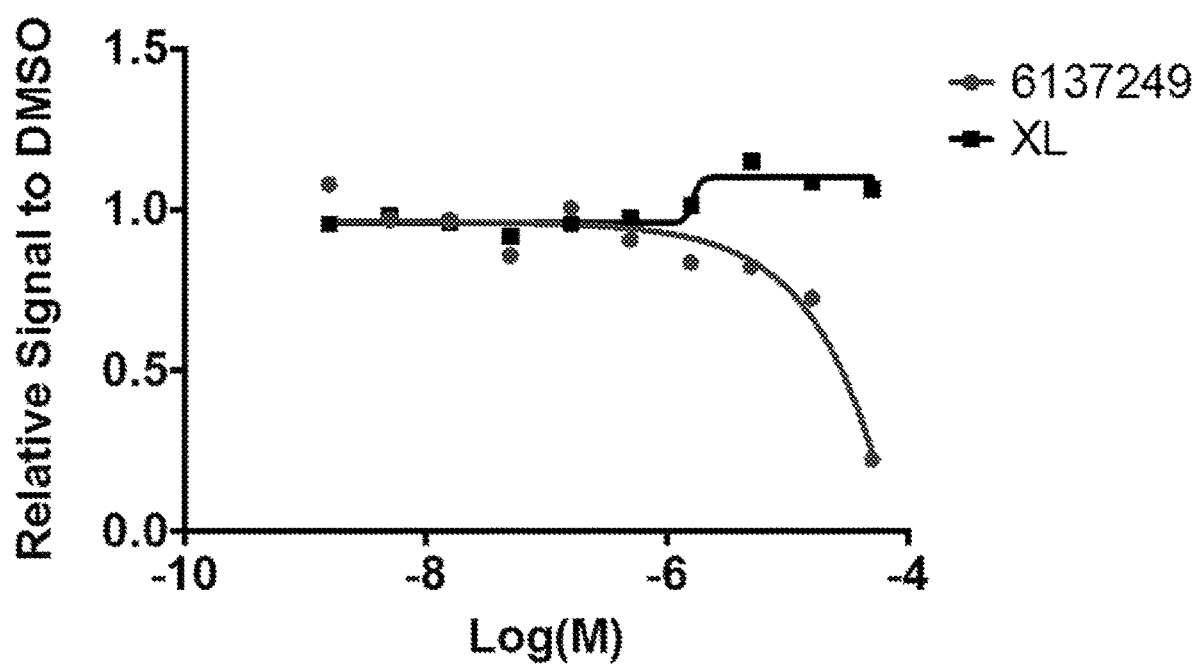
FIG. 6 is a plot the results for the AlphaScreen assay for certain compounds of Formula II.

The overall hit rate in was 0.9%, higher than most biochemical screens, but was expected due to the rate of compounds interfering with AlphaScreen detection. All the assays that were run have also been screened against other proteins using AlphaScreen technology (bromodomains and methyltransfersases). Compounds that are active in all three screens were removed from consideration and annotated as 'AlphaScreen inhibitors'. This filter decreased the hit rate to 0.4%, and a set of 3 scaffolds (FIG. 2) was assessed for potency and selectivity in biochemical and cellular assays.

Example 3

In order to further test and confirm the binding potency of the three 'hit' scaffolds to CBX, a collection of compounds was designed and synthesized for each scaffold to explore the structure-activity relationship (SAR). For Scaffold 1, a synthetic route was established to produce a variety of amides (Scheme 14). However, modification at the R position (highlighted) did not improve activity over the original compound. Further modification of the acid motif of Scaffold 1 also completely destroyed the compound's activity as assayed by the CBX AlphaScreen (FIG. 1). The narrow SAR around Scaffold 1 prompted the exploration of other scaffolds.

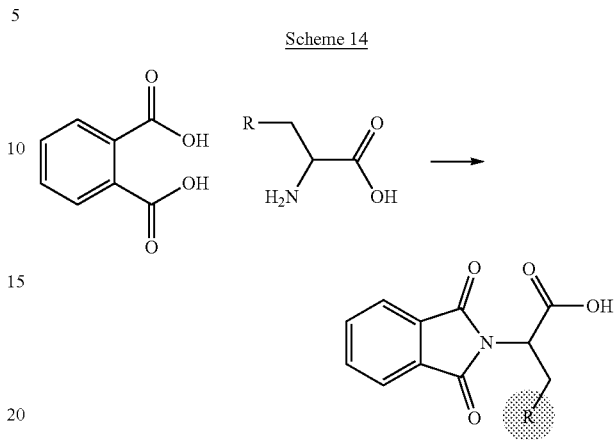

Example 4

Figure 7:
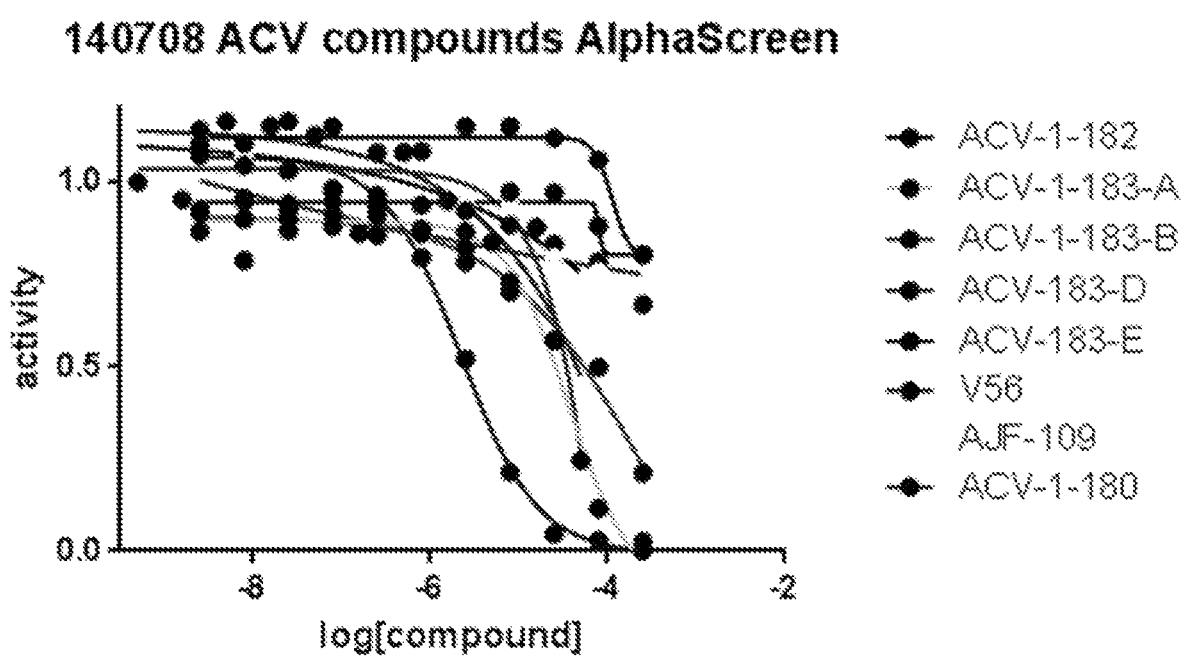
FIG. 7 is a plot the results for the AlphaScreen assay for certain compounds of Formula I.
Figure 8:
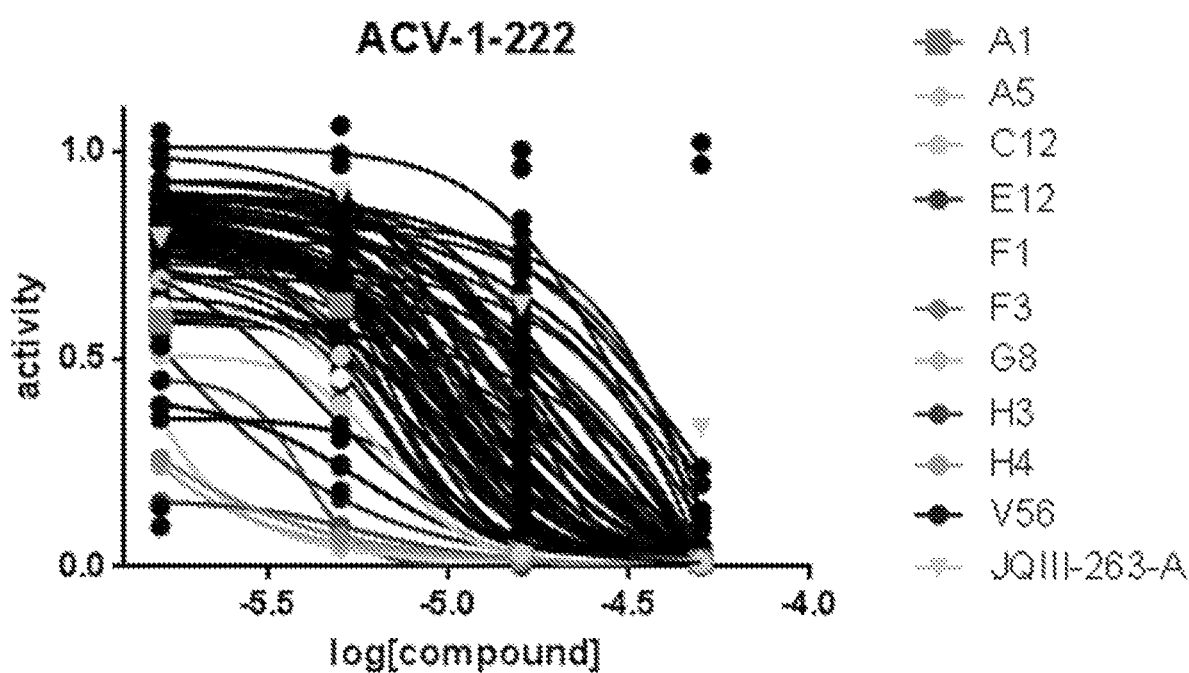
FIG. 8 is a plot if the initial Cap Scan Results for certain compounds of Formula II.

Next, the SAR around Scaffold 2 was explored by utilizing a hydrazone library synthesis strategy or 'cap scanning' method to produce more than 400 analogues of Scaffold 2 in a high-throughput manner. Among these compounds, several molecules were identified with improved binding affinity for CBX. Among these compounds, ACV-1-183A and ACV-1-183D provided more than 5-fold improvement in binding affinity compared to the original scaffold (FIG. 7). The same 'cap scanning' synthesis strategy was utilized to explore the optimization of Scaffold 3. The resulting library of compounds was screened via the CBX AlphaScreen assay and a series of promising molecules were identified, such as JQI-III-263-A, with improved activity (FIG. 8).

Figure 9:
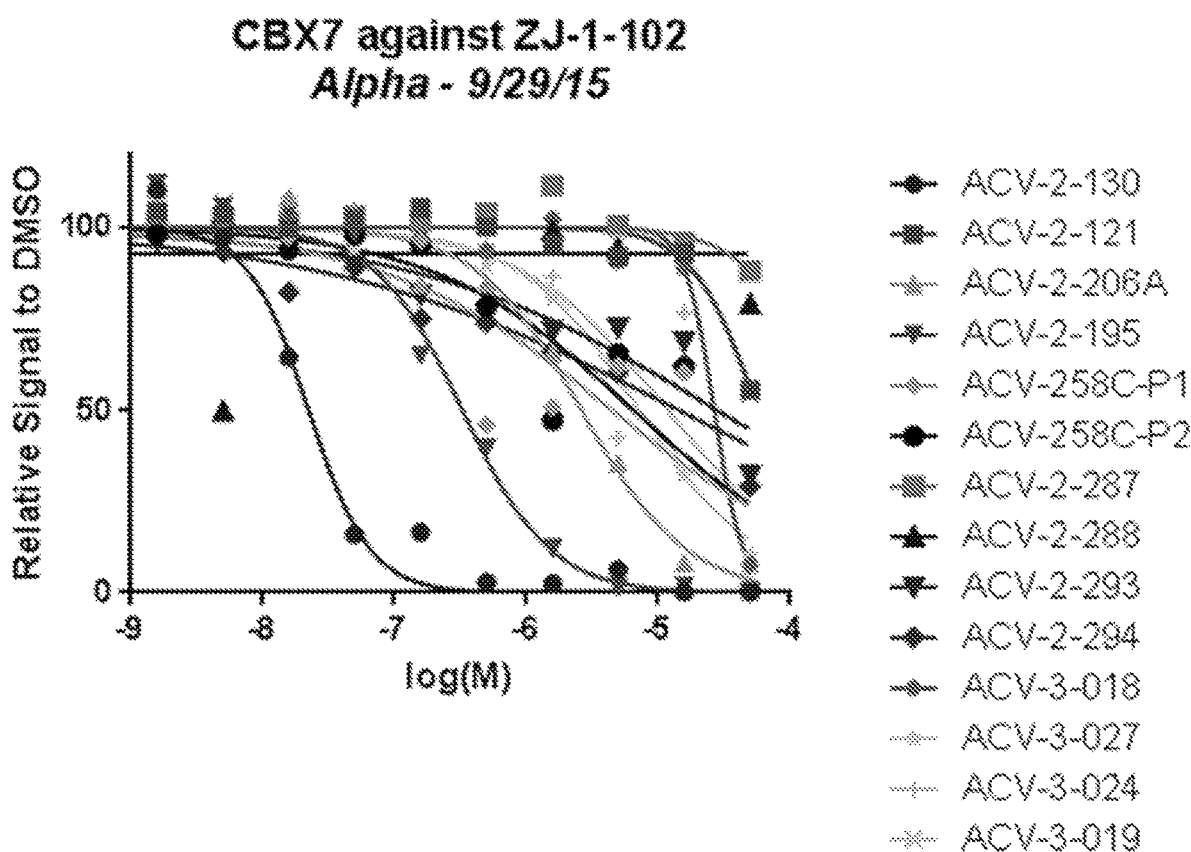
FIG. 9 is a plot the results for the AlphaScreen assay for certain compounds of Formula II.
Figure 10:
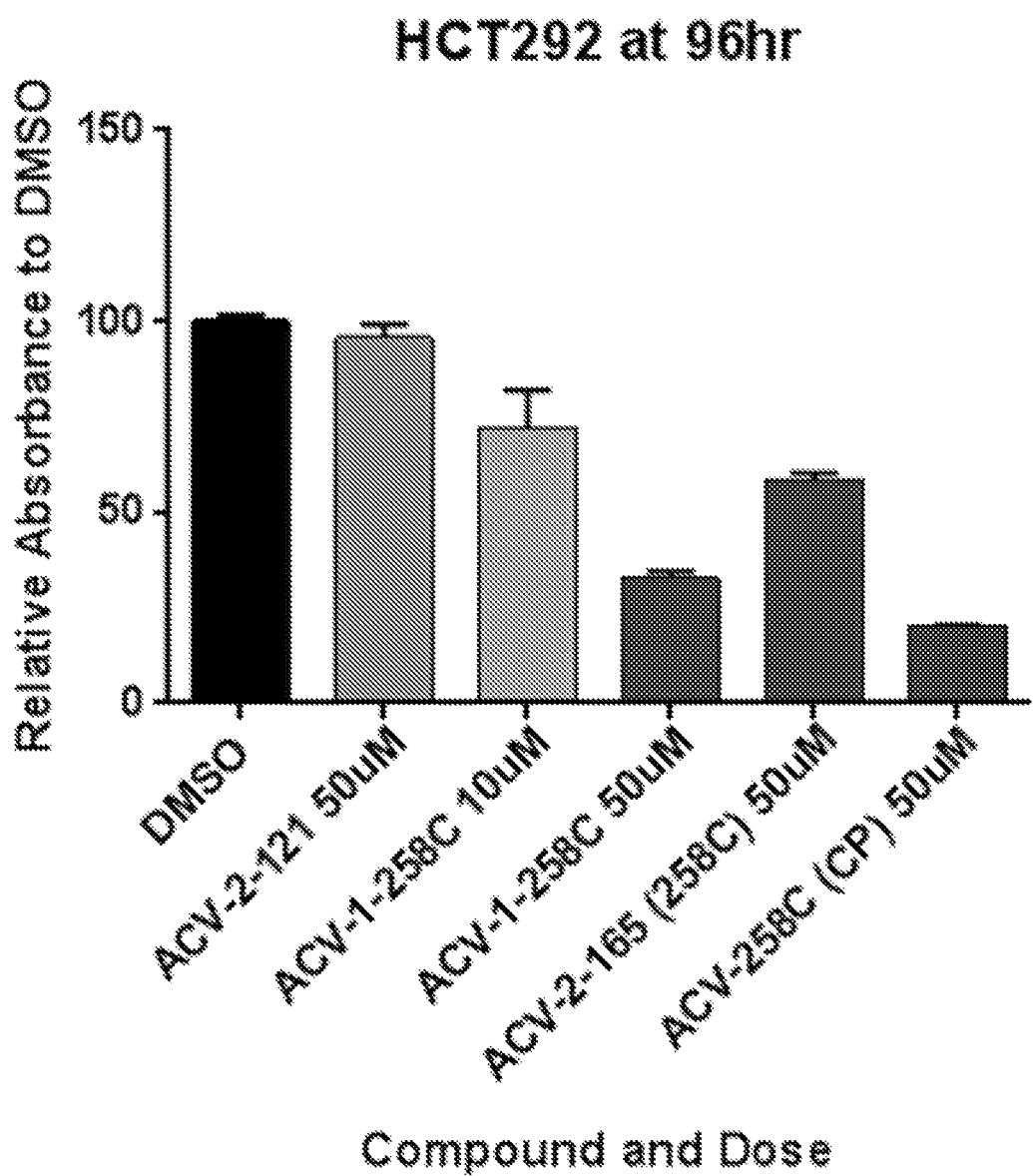
FIG. 10 is a bar graph depicting data representing decreased viability of HCT292 human lung cancer cells after 96 hours in the presence of certain compounds of the invention at various doses.
Figure 11:
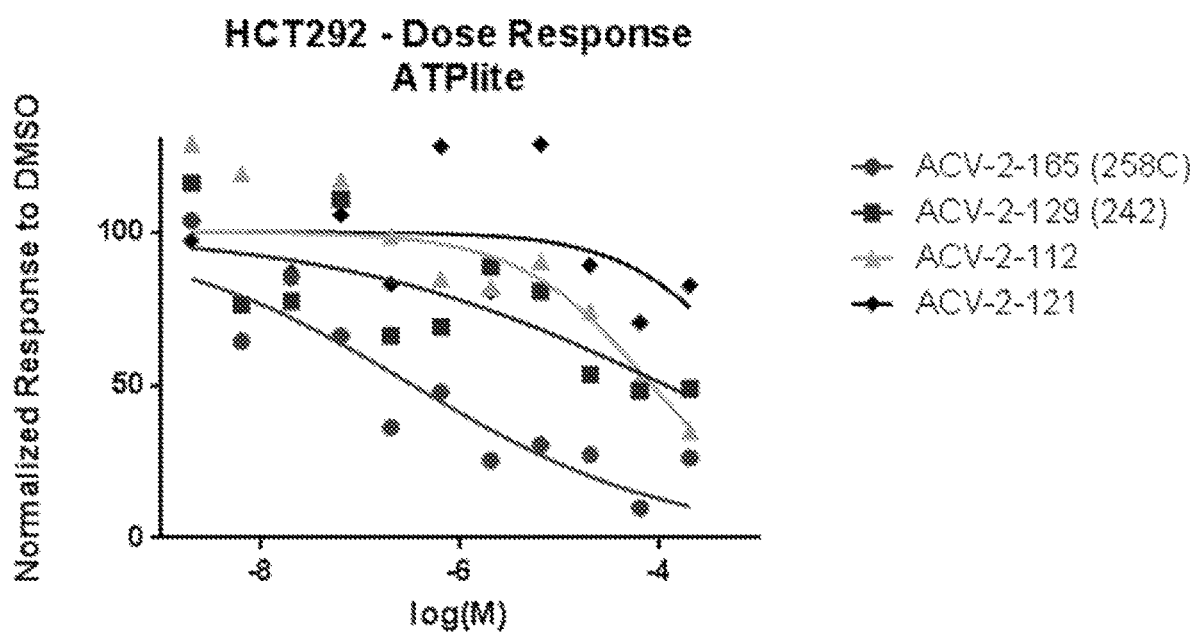
FIG. 11 is a plot depicting data representing decreased viability of HCT292 human lung cancer cells in the presence of certain compounds of the invention.
Figure 12:
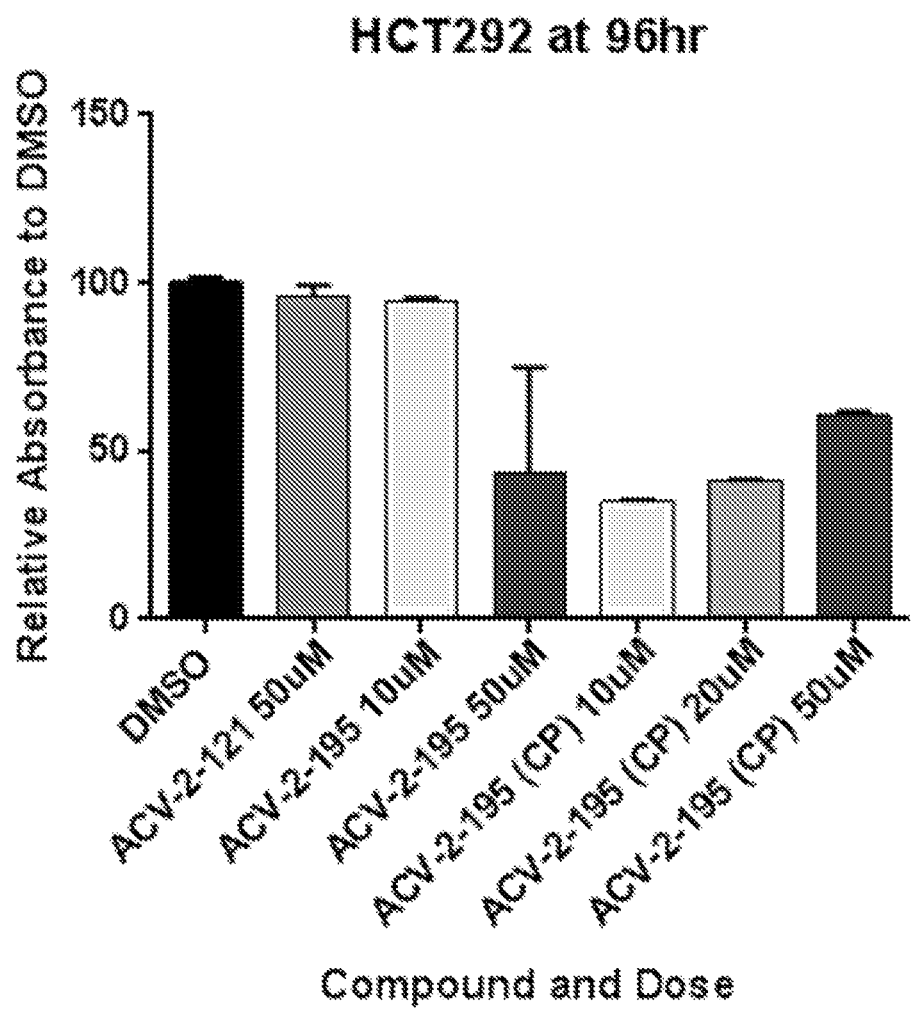
FIG. 12 is a bar graph depicting data representing decreased viability of HCT292 human lung cancer cells after 96 hours in the presence of certain compounds of the invention at various doses.
Figure 13:
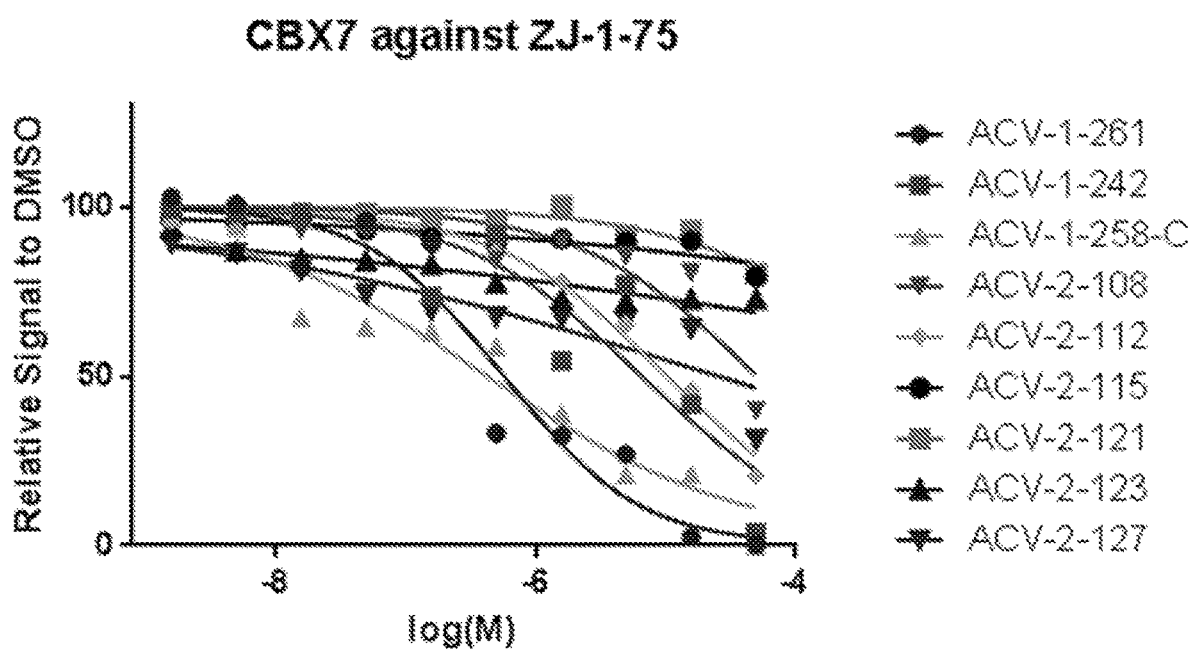
FIG. 13 is a plot of the results for the AlphaScreen assay for certain compounds of Formulas I, II, IV and V.
Figure 14:
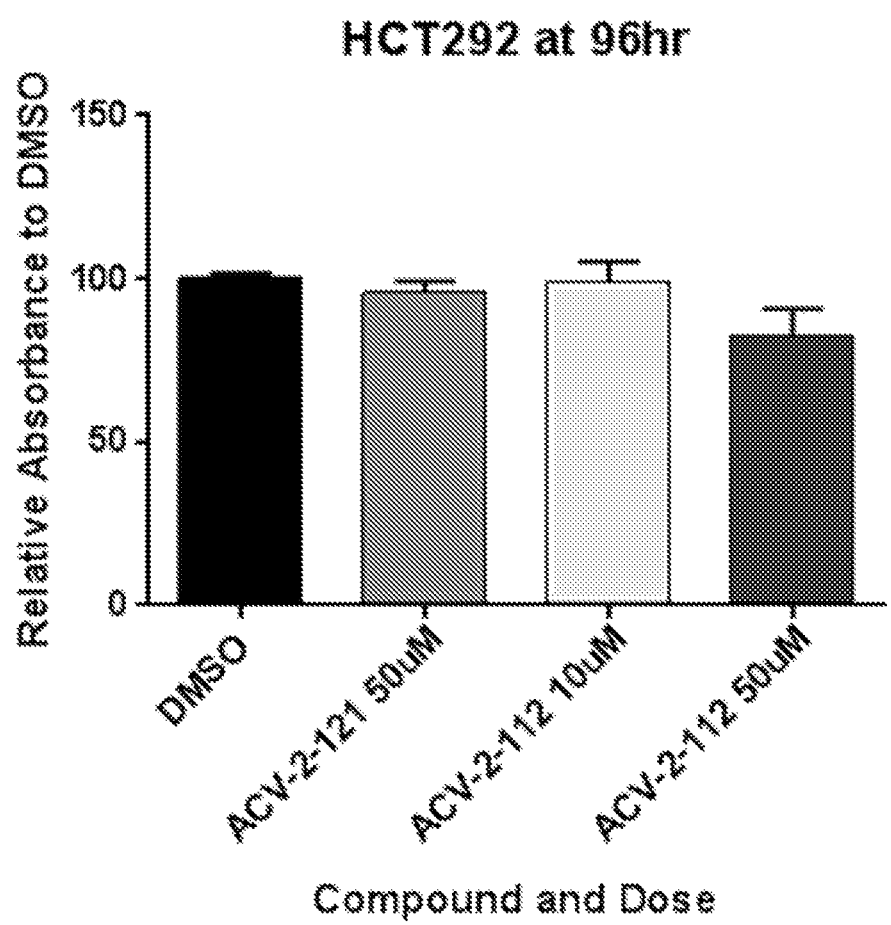
FIG. 14 is a bar graph depicting data representing decreased viability of HCT292 human lung cancer cells after 96 hours in the presence of certain compounds of the invention at various doses.
Figure 20:
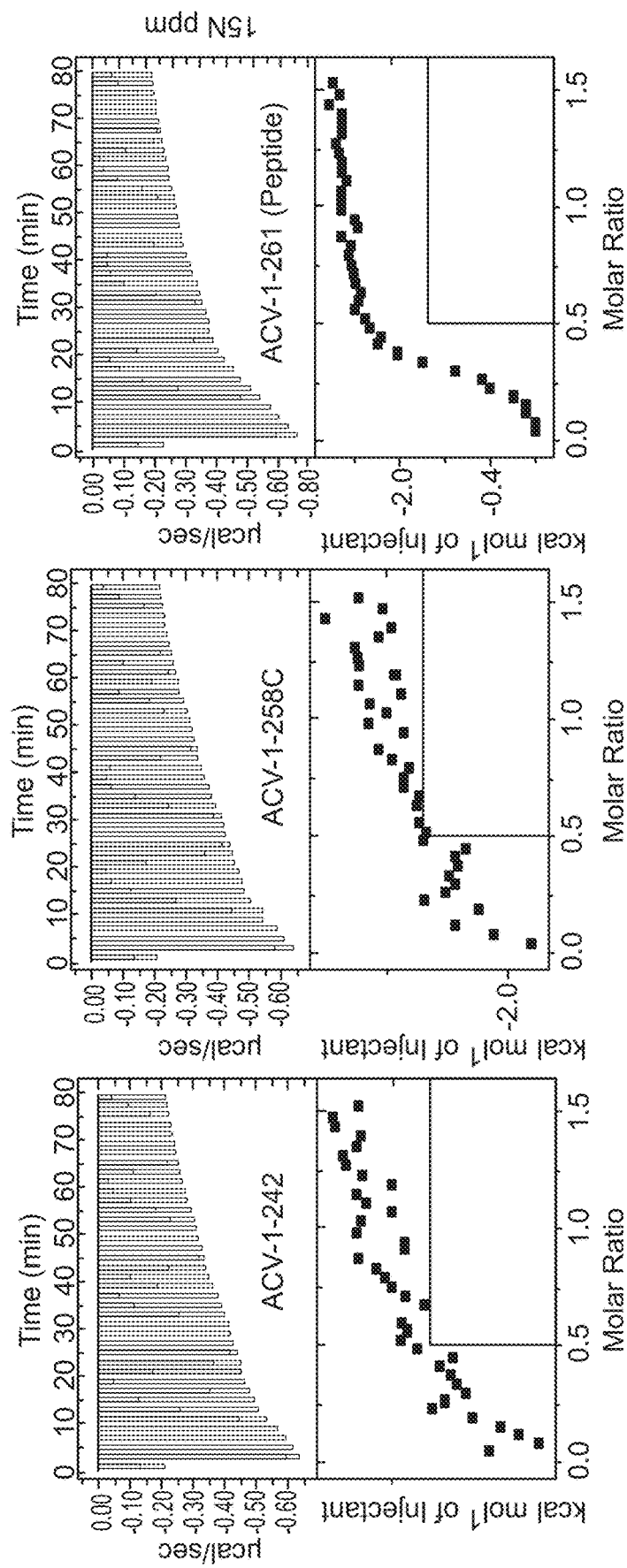
FIG. 20 shows the ITC data for CBX7 with certain small molecule inhibitors disclosed herein.
Figure 21A:
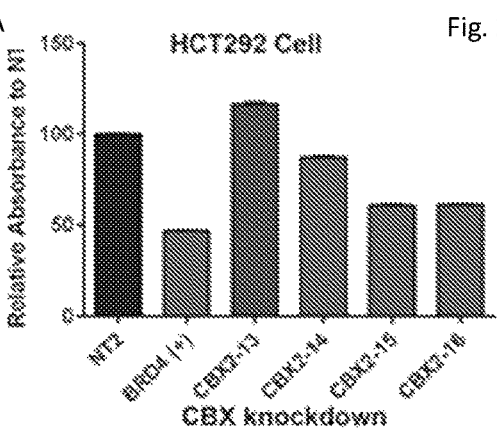
FIGS. 21A-21D show the biological activity of certain compounds of the invention in cancer cell lines sensitive to CBX inhibition and insensitive to CBX inhibition.
Figure 21B:
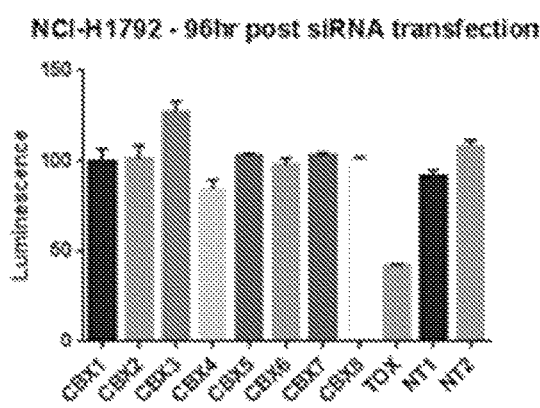
Figure 21C:
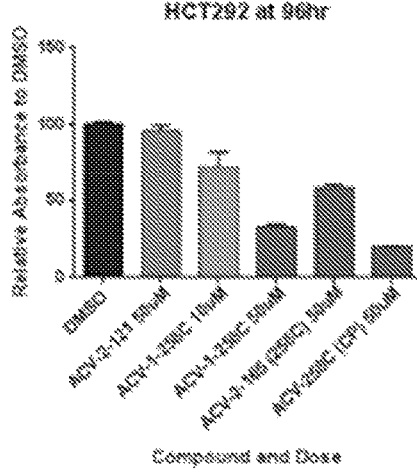
Figure 21D:
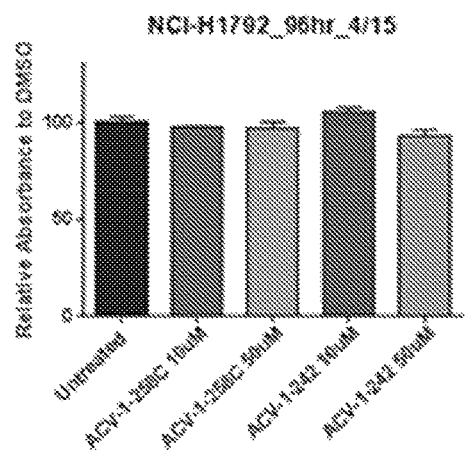

Encouraged by the SAR established through library optimization of the three hit scaffolds, novel compounds were generated by combining the motifs that improved activity into the backbone of Scaffold 3. A new series of compounds were designed and synthesized based on computational modeling of inhibitor compounds with the literature reported crystal structure of CBX. This novel set of molecules has largely improved binding affinity for CBX (FIG. 9). Notably, ACV-1-285 possesses low micromolar binding affinity with CBX. The binding affinity of the small molecule was further confirmed by isothermal titration calorimetry (FIG. 20).

Example 5

To predict the interaction between compounds and CBX protein, a 15N labeled CBX was generated for use in NMR studies. The labeled protein was used to map the interaction between the small molecule inhibitor and CBX protein. Compound ACV-2-112, a potentially more stable produced significant peak relocation on CBX protein NMR, which further confirmed the binding of small molecule toward the CBX.

Figure 15:
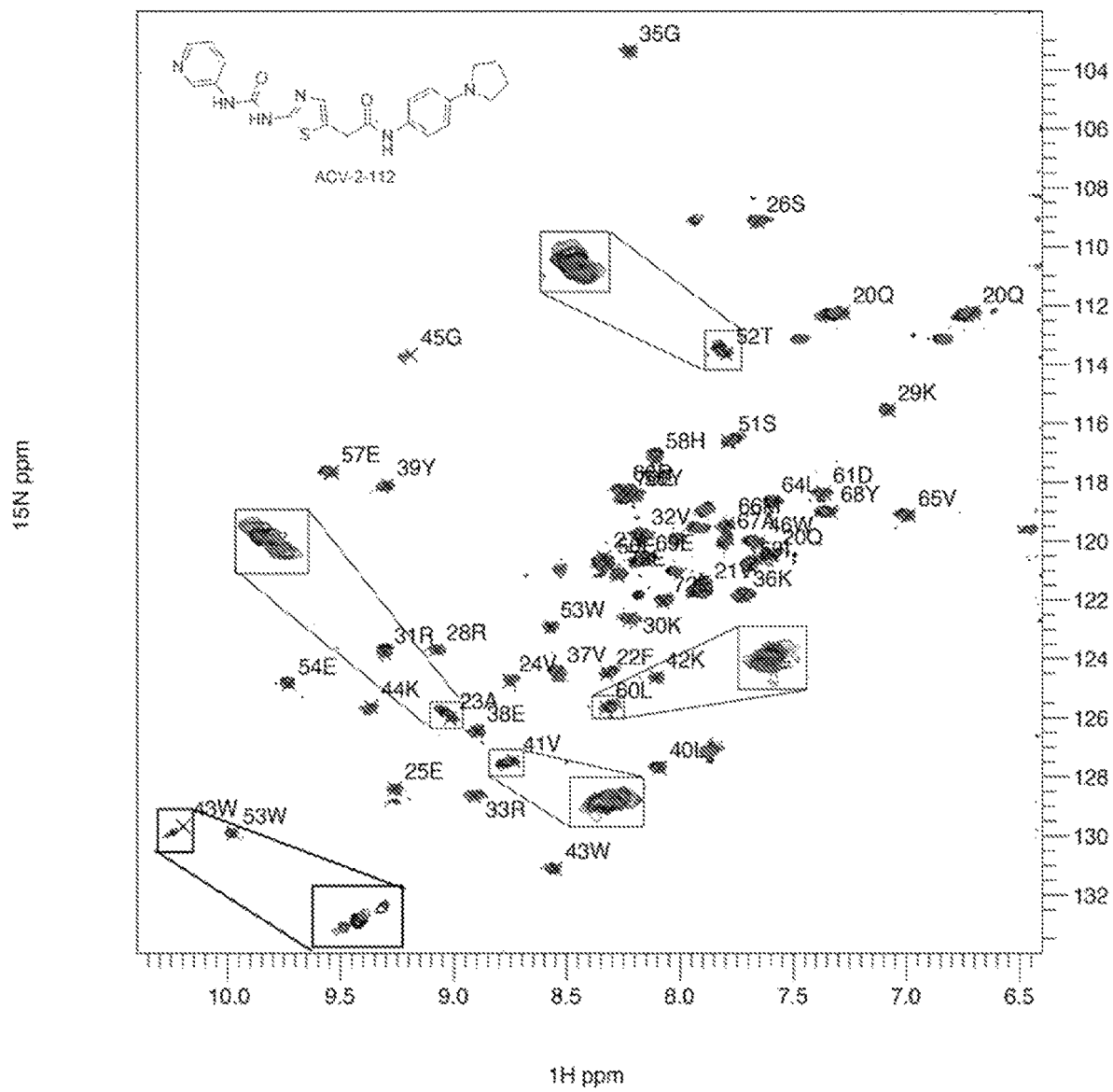
FIG. 15 is a plot of the ¹⁵N NMR spectrum vs. the ¹H NMR spectrum, which shows binding between ACV-2-112 with CBX7.
Figure 16:
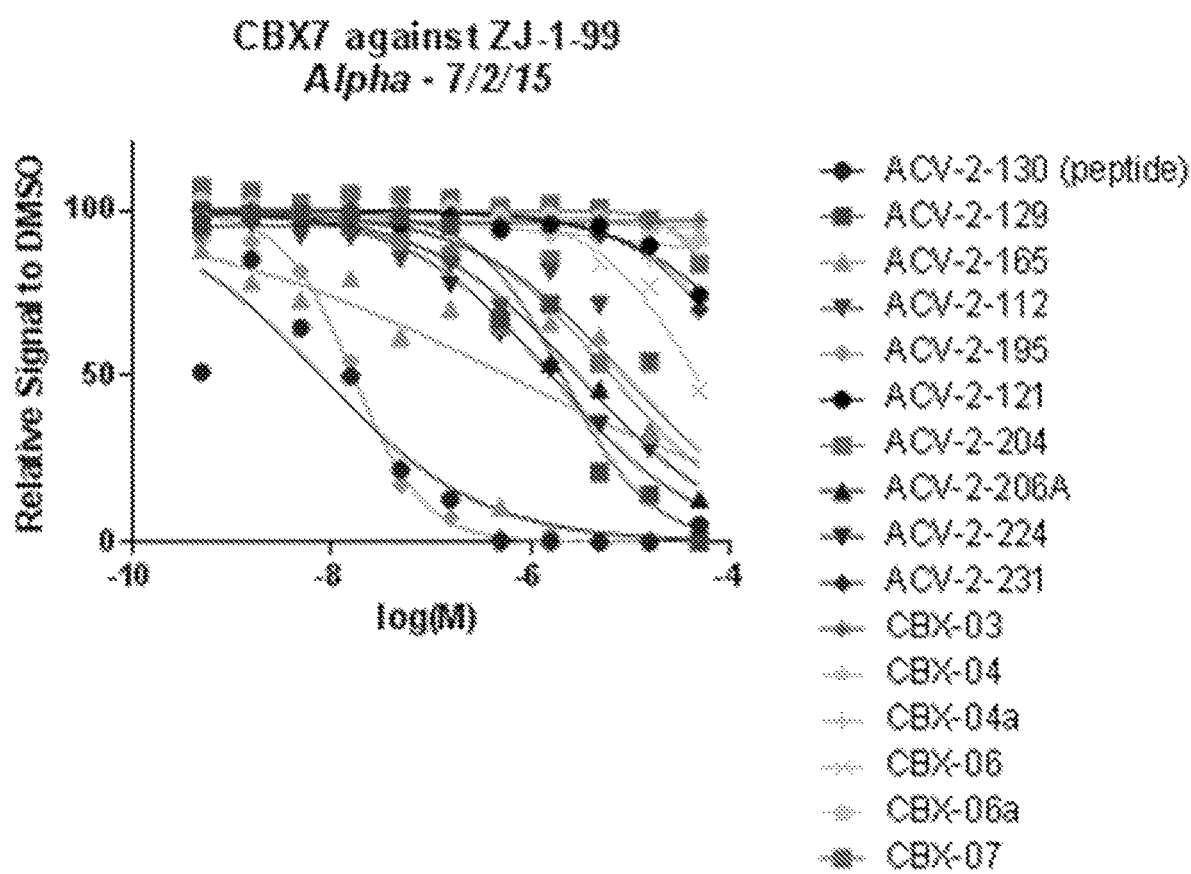
FIG. 16 is a plot of the results for the AlphaScreen assay for certain compounds disclosed herein in comparison to a known compound.
Figure 17:
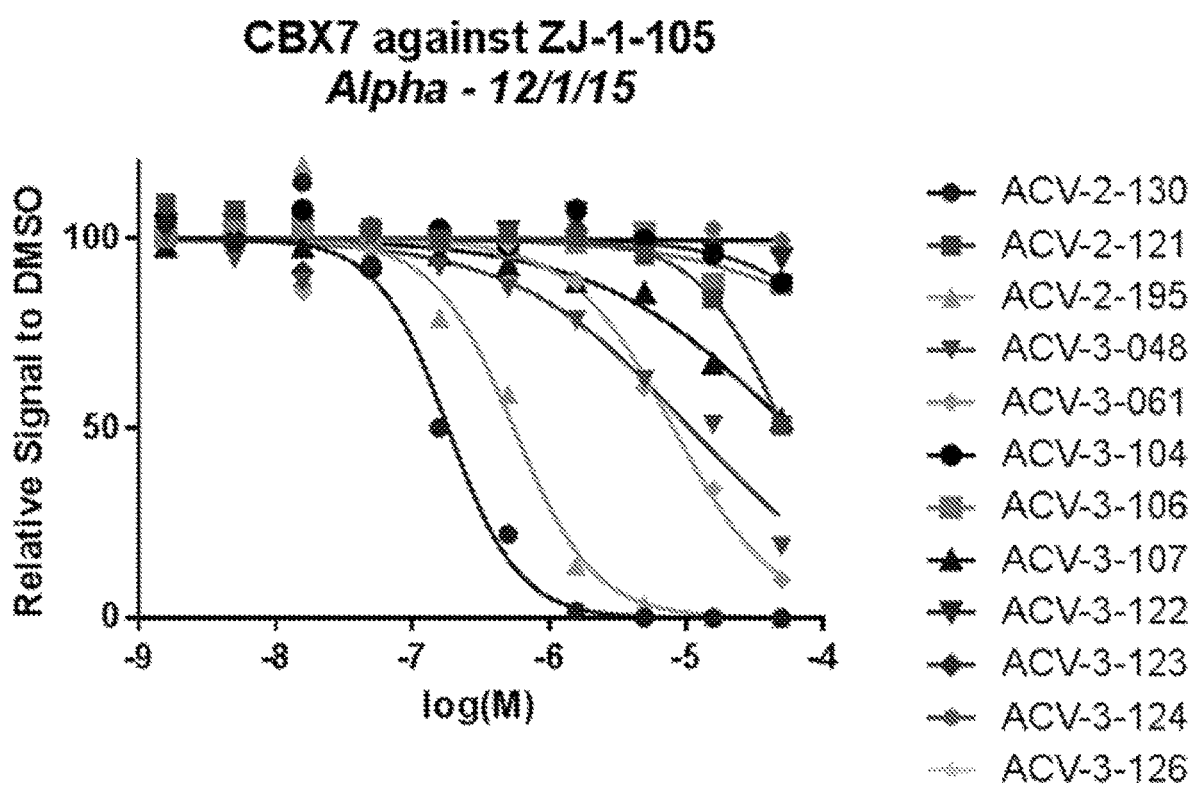
FIG. 17 is a plot of the results for the AlphaScreen assay for certain compounds disclosed herein.
Figure 18:
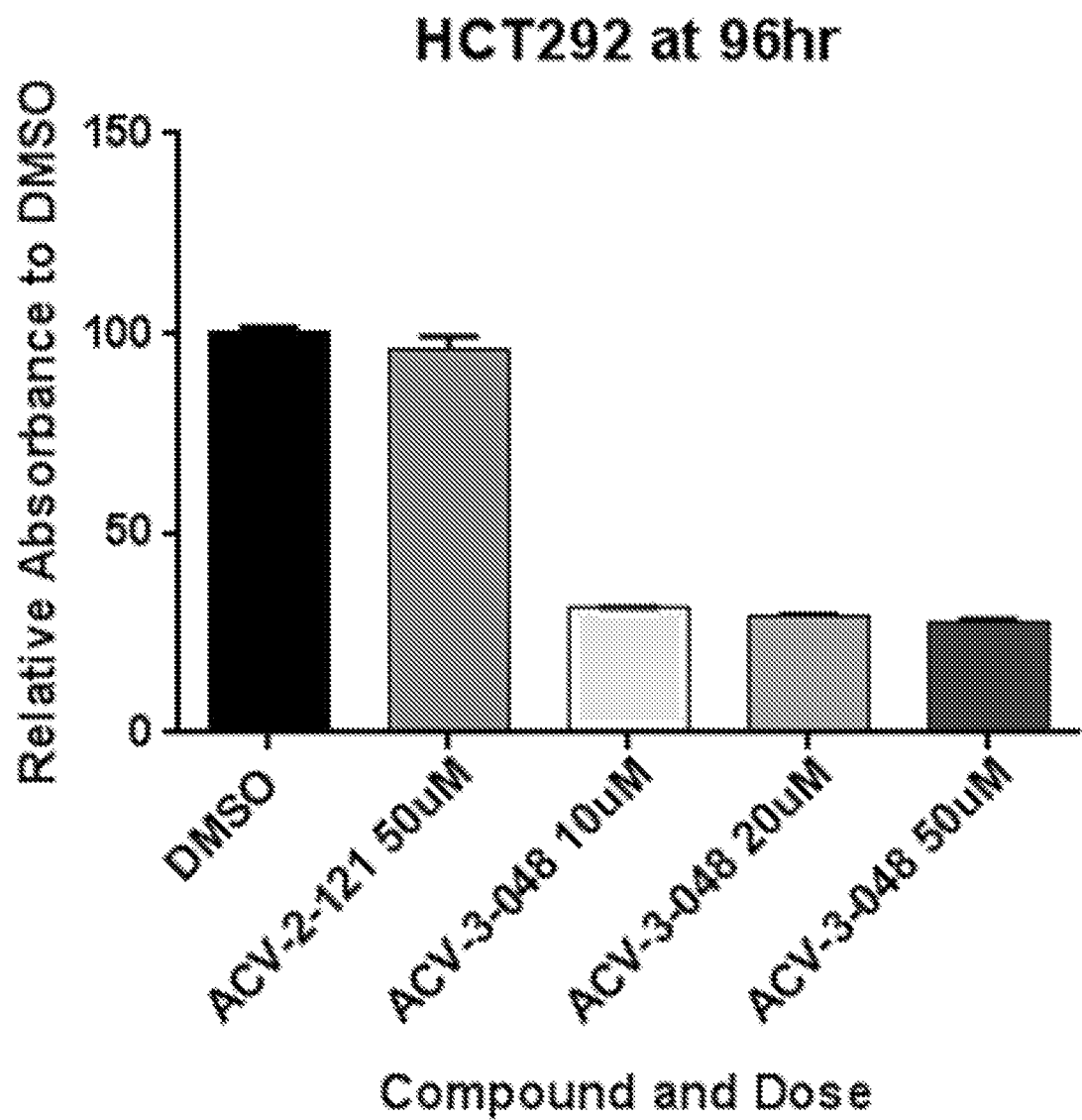
FIG. 18 is a bar graph depicting data representing decreased viability of HCT292 human lung cancer cells after 96 hours in the presence of certain compounds of the invention at various doses.
Figure 19:
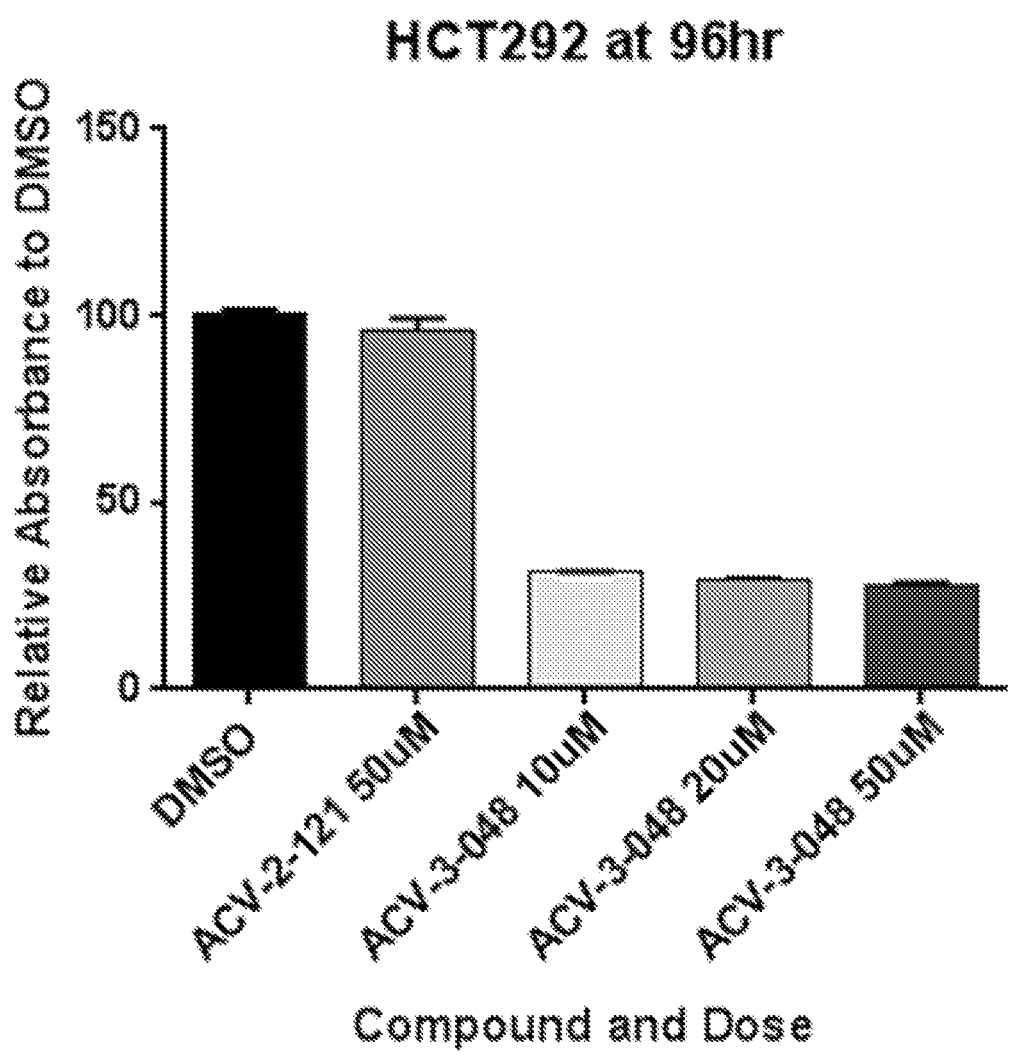
FIG. 19 is a bar graph depicting data representing decreased viability of HCT292 human lung cancer cells after 96 hours in the presence of certain compounds of the invention at various doses.

Briefly, an overnight culture of His6CBX7 was grown in 5 ml of LB with antibiotic. The inoculated 1 liter of the 15N base media (2 mM MgSO4, 100 uM CaCl2, 1 g 15NH4Cl, 25 ml 20% w/v Glucose in PBS) plus antibiotic with the overnight culture and incubated at 37 C. The temperature of the media was reduced to 23° C. at OD=4.0 and induced at OD=7 with 1 mM isopropyl-thio-β-D-galactopyranoside and incubated for an additional 12 hours. The culture was then pelleted and protein purification was started. Each pellet was resuspended in 40 ml lysis buffer (250 mM NaCl in PBS plus Halt protease inhibitor) and homogenized for 1 hour at 4 C. Cell lysis was accomplished by sonication on ice, the sonication protocol was a 5 second pulse at amplitude=40, 30 second rest, for 10 minutes total sonication time. Unclarified lysate was mixed with 3-4 ml Ni-NTA superflow Resin (Qiagen). The mixture was incubated overnight on ice. The next day it was loaded onto an empty column and washed with 20 ml wash buffer A (250 mM NaCl, 10 mM imidizole in PBS) and 5 ml wash buffer B (250 mM NaCl, 50 mM imidazole in PBS). Samples were eluted from the resin by exposure to 2-3 column volumes of elution buffer (250 mM NaCl, 500 mM imidazole in PBS) and collected in fractions. Elution fractions containing protein were confirmed by a protein gel and the protein was dialyzed overnight in dialysis buffer (300 mM NaCl, 500 mM tris(2-carboxyethyl)phosphine in PBS). The N15 labeled protein was titrated with the ligand ACV-2-112 and HSQC spectra were recorded for each point using the 500 Hz NMR located in the HMS East Quad NMR facility. FIG. 15 shows preliminary data from the experiment that seems to indicate the compound ACV-2-112 is binding into the aromatic cage of the CBX protein which is the same area that coordinates the trimethylated lysine residue of the peptide.

The amino acids interacted with small molecule were assigned based literature reported NMR structure of CBX, and identified the binding site of small molecule on CBX.

Example 6

Lastly, the biological activity of lead compounds was assessed in cancer cells lines determined to be sensitive to CBX inhibition. First, a cell line screening for CBX2 and CBX3 dependence/sensitivity was conducted using shRNAs. It was found that the HCT292 human lung cancer cell line was sensitive to CBX2 and CBX3 knockdown, while the NCI-H1792 human lung cancer cell line was not. These cell lines were utilized to evaluate the potential cellular activity of a panel of CBX inhibitors (Tables 3-9).

Briefly, HCT292 cells were treated 24 hours after passage; the compounds in DMSO were added directly to their media. Initially, which cells caused cell death was checked by fixing and staining the cells with crystal violet 96-hours post treatment and then reading the absorbance using the Envision and comparing the signal to a DMSO control. This was done as a preliminary viability screen prior to the ATPlite assay to determine which compounds HCT292 cells were and H661 cells were not sensitive to. Then, cell viability assays were performed using the ATPlite kit to determine which compounds decreased cell viability. The small molecule CBX inhibitors that are disclosed herein effectively inhibit the growth of HCT292 cells in the similar manner as the shRNA. On the other hand, these molecules did not show any activity against the insensitive cell line, NCI-H17912 (FIG. 21). Thus, a cellular system to evaluate the activity of small molecule CBX inhibitors was established.

Example 7

The protocol for the CBX7 Fluorescence Polarization assay is as follows: A standard FP buffer (20 mM Tris, 250 mM NaCl, 0.01% w/v Tween20) at pH 8.0 is created and make up one stock solution at 1× final concentration in the FP buffer. The solution contains Human His6-CBX7 used with FITC-VARKme3SA, at 250 nM and 10 nM respectively. For 384 well assay formats, 10 uL of solution is added to each well of the assay plate and the plate is spun at 1000 rpm for 30 seconds. 100 nL of experimental compounds from stock plates are delivered by robotic pin transfer using a Janus Workstation (PerkinElmer), allowing the compounds to interact with CBX7 binding prior to assay measurement, followed by another spin and an incubation room temperature. Fluorescence Polarization measurements are performed on an Envision 2104 (PerkinElmer) utilizing the manufacturer's protocol that has the correct excitation and emission wavelengths, cutoff filters, delay time, etc. A crosstalk calculation is also done through the Envision software to correct for luminescence for adjacent wells while reading the plate. The signal is then normalized to DMSO control wells on the compound plate prior to creation of the $IC_{50}$ curves.

TABLE 3

| Compound, dose | % Viability |
|---|---|
| DMSO | 100 |
| 2-121, 50 uM | 95.8 |
| 1-258C, 10 uM | 72.2 |
| 1-258C, 50 uM | 33.0 |
| 2-165, 50 uM | 58.8 |
| 258C (CP), 50 uM | 20.3 |

TABLE 4

| Compound | IC50 (uM) |
|---|---|
| ACV-2-165 (258C) | 0.3337 |
| ACV-2-129 (242) | 115.3 |
| ACV-2-112 | 83.93 |
| ACV-2-121 | 1001 |

TABLE 5

| Compound, dose | % Viability |
|---|---|
| DMSO | 100 |
| 2-121, 50 uM | 95.8 |
| 2-195, 10 uM | 94.2 |
| 2-195, 50 uM | 43.5 |
| 2-195 (CP), 10 uM | 34.9 |
| 2-195 (CP), 20 uM | 41.0 |
| 2-195 (CP), 50 uM | 60.6 |

TABLE 6

| Compound, dose | % Viability |
|---|---|
| DMSO | 100 |
| 2-121, 50 uM | 95.8 |
| 2-112, 10 uM | 99.0 |
| 2-112, 50 uM | 82.9 |

TABLE 7

| Compound, dose | % Viability |
|---|---|
| DMSO | 100 |
| 2-121, 50 uM | 95.8 |
| 3-048, 10 uM | 31.3 |

TABLE 7-continued

| Compound, dose | % Viability |
|---|---|
| 3-048, 20 uM | 29.0 |
| 3-048, 50 uM | 28.0 |

TABLE 8

| Compound, dose | % Viability |
|---|---|
| DMSO | 100 |
| 2-121, 50 uM | 95.8 |
| 3-061, 10 uM | 33.5 |
| 3-061, 20 uM | 30.5 |
| 3-061, 50 uM | 18.0 |

TABLE 9

| Compound Name | Alternate Name | AVG CBX7 Alpha IC50 (M) | AVG CBX2 Alpha IC50 | CBX7 FP |
|---|---|---|---|---|
| ACV-01 | ACV-1-180 | 2.83E+01 | 1.03E-04 | |
| ACV-02 | ACV-1-182 | 1.44E-01 | 5.54E-05 | |
| ACV-03 | ACV-1-183-A | 4.45E-07 | 2.15E-05 | |
| ACV-04 | ACV-1-183-B | 3.52E-07 | 2.55E-06 | |
| ACV-05 | ACV-1-183-D | 1.88E-06 | 0.00E+00 | |
| ACV-06 | ACV-1-183-E | 1.36E-05 | 1.44E-03 | |
| ACV-07 (1) | ACV-1-190 | | | |
| ACV-07 (2) | ACV-2-192 | 1.94E-04 | 8.55E-02 | |
| ACV-08 | ACV-1-191 | 1.03E-05 | 4.77E-05 | |
| ACV-09 | ACV-1-195-A | 7.39E-06 | 2.82E-05 | |
| ACV-10 | ACV-1-195-D | 2.02E-05 | 9.88E-05 | |
| ACV-11 | ACV-1-202 | 8.51E-06 | | |
| ACV-12 | ACV-1-204 | 6.10E-06 | 0.00E+00 | |
| ACV-13 | ACV-1-205 | 6.95E-05 | 3.18E-01 | |
| ACV-14 (1) | ACV-1-242 | 4.41E-06 | 1.52E-05 | 3.04E-04 |
| ACV-14 (2) | ACV-2-129 | 1.02E-05 | 1.97E-06 | |
| ACV-15 | ACV-1-258-A | 3.73E-05 | 5.52E-06 | |
| ACV-16 | ACV-1-258-B | 6.79E-06 | 2.04E-05 | |
| ACV-17 (1) | ACV-1-258-C | 6.97E-05 | 7.87E-07 | 1.20E-04 |
| ACV-17 (2) | ACV-2-165 | 9.30E-07 | 5.72E-07 | |
| ACV-17(3) | ACV-2-189 | 1.01E-06 | 3.79E-07 | |
| ACV-17(4) | ACV-2-206-A | 1.56E-06 | 2.60E-07 | |
| ACV-17(CP) | ACV-258C (CP) | 1.74E-06 | | |
| ACV-17* (P1) | ACV-258C (P1) | 2.36E-06 | | |
| ACV-17* (P2) | ACV-258C (P2) | 3.37E-06 | | |
| ACV-18 | ACV-1-259 | 6.91E+01 | 3.67E-05 | |
| ACV-19 | ACV-1-261 | 3.35E-03 | 9.42E-07 | 1.52E-04 |
| ACV-20 | ACV-1-273 | 2.86E-05 | 5.56E-06 | |
| ACV-21 | ACV-1-283-B | 3.69E-06 | 2.40E-04 | |
| ACV-22 | ACV-1-285-D1/ACV-1-285-MIX | 1.29E-02 | 1.17E-04 | |
| ACV-22 | ACV-1-285-D1/ACV-1-285-MIX | 5.85E-06 | 2.89E-04 | |
| ACV-23 | ACV-1-288 | 0.00E+00 | 2.00E-06 | |
| ACV-24 | ACV-2-007-A | 6.53E-05 | 4.37E-05 | 0.00E+00 |
| ACV-25 | ACV-2-007-B | 6.09E-05 | 2.51E-05 | 0.00E+00 |
| ACV-26 | ACV-2-011-A | 1.66E-05 | 2.28E-05 | 2.26E+02 |
| ACV-27 | ACV-2-011-B | 3.39E-05 | 3.51E-05 | 2.89E+02 |
| ACV-28 | ACV-2-015 | 4.46E-05 | 5.60E-05 | 6.67E-03 |
| ACV-29 | ACV-2-016-A/B | 3.90E-05 | 3.84E-05 | 1.39E+03 |
| ACV-29 | ACV-2-016-A/B | 1.55E-05 | 1.65E-05 | 8.00E+00 |
| ACV-30 | ACV-2-019 | 3.90E-05 | 2.09E-05 | |
| ACV-31 | ACV-2-023 | 4.04E-04 | 2.05E-05 | |
| ACV-32 | ACV-2-024 | 2.35E-05 | 2.29E-05 | |
| ACV-33 | ACV-2-026 | 5.62E-05 | 6.25E-05 | |
| ACV-34 | ACV-2-029 | 7.90E-06 | 1.03E-07 | |
| ACV-35 | ACV-2-049 | 3.05E-06 | 2.21E-02 | |
| ACV-36 (1) | ACV-2-082 | 1.00E-05 | 1.70E-05 | |
| ACV-36 (2) | ACV-2-163 | 2.45E-05 | 2.88E-05 | |
| ACV-37 | ACV-2-083 | 1.14E-04 | 6.66E-05 | |
| ACV-38 | ACV-2-084 | 1.65E-04 | | |
| ACV-39 | ACV-2-108 | 2.63E-05 | 1.25E-05 | |
| ACV-40 | ACV-2-112 | 1.28E-05 | 1.85E-05 | |
| ACV-41 | ACV-2-115 | 1.45E-03 | 2.56E-04 | |
| ACV-42 | ACV-2-121 | 1.55E-04 | 7.22E-05 | |
| ACV-43 | ACV-2-123 | 9.10E-03 | 6.73E-03 | |
| ACV-44 | ACV-2-127 | 1.01E-04 | 7.82E-05 | |
| ACV-45 | ACV-2-132 | 1.15E-01 | 3.13E-03 | |
| ACV-46 | ACV-2-138 | 8.84E-05 | 1.39E+13 | |
| ACV-47 | ACV-2-142 | 1.44E-02 | 1.04E-01 | |
| ACV-48 (1) | ACV-2-147 | 4.03E-04 | 1.89E-04 | |
| ACV-48 (2) | ACV-2-147 | 6.07E-04 | 2.59E-04 | |
| ACV-49 | ACV-2-150 | 1.72E-05 | 1.28E-05 | |
| ACV-50 | ACV-2-151 | 7.20E-06 | 1.31E-05 | |
| ACV-51 | ACV-2-152 | 2.41E-05 | 3.57E-05 | |
| ACV-52 | ACV-2-154 | 6.58E-06 | 9.34E-06 | |
| ACV-53 | ACV-2-155 | 1.25E-05 | 4.79E-05 | |
| ACV-54 | ACV-2-156 | 9.31E-06 | 7.99E-06 | |
| ACV-55 | ACV-2-160 | 2.30E-05 | 4.81E-05 | |
| ACV-56 | CBX-01 | 6.41E-05 | 0.00E+00 | |
| ACV-57 | CBX-02 | 3.36E-04 | 0.00E+00 | |
| ACV-58 | ACV-2-130 | 1.75E-08 | 1.93E-08 | |
| ACV-59 | ACV-2-179 | 7.59E-04 | 5.51E-05 | |
| ACV-60 | ACV-2-185 | 3.64E-07 | 1.67E-07 | |
| ACV-61 | ACV-2-188 | 3.94E-06 | 1.93E-06 | |
| ACV-62 | ACV-2-191 | 8.61E-07 | 6.09E-07 | |
| ACV-63 | ACV-2-195 | 1.83E-07 | 6.86E-08 | |
| ACV-63 (2) | ACV-3-018 | 2.25E-05 | | |
| ACV-63 (CP) | ACV-2-195 (CP) | 5.31E-06 | | |
| ACV-64 | ACV-2-203 | 5.22E-06 | 2.93E-05 | |
| ACV-65 | CBX-03a | | 2.99E-10 | |
| ACV-66 | ACV-2-204 | 1.19E-05 | 3.44E-07 | |
| ACV-67 | CBX-03 | 0.00E+00 | 1.89E-02 | |
| ACV-68 | CBX-04 | 3.96E+12 | | |
| ACV-69 | CBX-04a | 1.37E+00 | 0.00E+00 | |
| ACV-70 | CBX-06 | 4.67E-05 | 1.46E-05 | |
| ACV-71 | CBX-06a | 4.92E-03 | 0.00E+00 | |
| ACV-72 | CBX-07 | 1.24E-04 | | |
| ACV-73 | ACV-2-224 | 1.65E-06 | 1.96E-07 | |
| ACV-74 | ACV-2-231 | 1.67E-04 | 7.21E-05 | |
| ACV-75 | ACV-2-233 | 6.86E-08 | | |
| ACV-76 | ACV-2-247 | 3.76E-06 | | |
| ACV-77 | ACV-2-251 | | | |
| ACV-78 | ACV-2-254 | 2.25E-07 | | |
| ACV-79 | ACV-2-270 | 3.01E-06 | | |
| ACV-80 | CBX-05 | 2.86E-11 | | |
| ACV-81 | ACV-2-287 | 1.04E-04 | | |
| ACV-82 | ACV-2-288 | 5.08E-05 | | |
| ACV-83 | ACV-2-293 | 2.39E-05 | | |
| ACV-84 | ACV-2-294 | 7.26E-06 | | |
| ACV-85 | ACV-3-019 | 5.48E-06 | | |
| ACV-86 | ACV-3-024 | 1.18E-05 | | |
| ACV-87 | ACV-3-027 | 7.26E-06 | | |
| ACV-88 | ACV-3-042 | 2.46E-04 | | |
| ACV-89 | ACV-3-048 | 1.29E-05 | | |
| ACV-90 | ACV-3-060 | 6.71E-01 | | |
| ACV-91 | ACV-3-061 | 1.20E-05 | | |
| ACV-92 | ACV-3-074 | 1.70E-04 | | |
| ACV-93 | ACV-3-144 | 4.40E-04 | | |
| ACV-94 | ACV-3-073 | 1.23E-04 | | |
| ACV-95 | ACV-3-090 | 8.79E-04 | | |
| ACV-96 | ACV-3-096 | 7.93E-05 | | |
| ACV-97 | ACV-3-104 | 8.17E-05 | | |
| ACV-98 | ACV-3-106 | 1.21E-04 | | |
| ACV-99 | ACV-3-107 | 1.64E-05 | | |
| ACV-100 | ACV-3-122 | | | |
| ACV-101 | ACV-3-123 | | | |
| ACV-102 | ACV-3-124 | | | |
| ACV-103 | ACV-3-126 | | | |
| | ACV-3-140 | | | |
| | ACV-3-142 | 6.60E-07 | | |
| | CBX-08 | 8.35E-07 | | |

TABLE 9-continued

| Compound Name | Alternate Name | AVG CBX7 Alpha IC50 (M) | AVG CBX2 Alpha IC50 | CBX7 FP |
|---|---|---|---|---|
| | CBX-09 | 5.34E−05 | | |
| | ACV-3-141 | 4.44E−05 | | |
| | ACV-3-145 | 2.73E−04 | | |
| | ACV-3-147 | 6.65E−06 | | |
| | ACV-3-191 | 1.06E−05 | | |
| | ACV-3-194 | 1.69E+01 | | |
| | ACV-3-195 | 3.56E+14 | | |
| | ACV-3-200 | 9.55E+03 | | |
| | ACV-3-205 | 6.83E−05 | | |
| | ACV-3-215 | 9.92E−05 | | |
| | ACV-3-217 | 5.23E−05 | | |

CBX-07 is

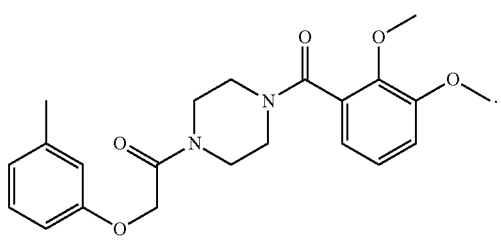 [SMILES: COc1cccc(C(=O)N2CCN(C(=O)COc3cccc(C)c3)CC2)c1OC]

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having a structure of Formula I or a pharmaceutically acceptable salt thereof:

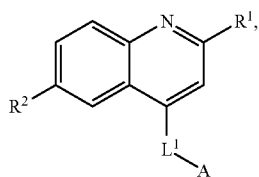

I wherein
$R^1$ is

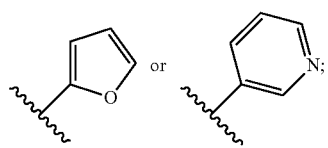 [SMILES: *c1ccco1 ; *c1cccnc1]

$R^2$ is H, halo, optionally substituted aryl, or optionally substituted heteroaryl;
$L^1$ is optionally substituted —C(O)NH-alkylene- or —C(O)NHNCH—; and
A is

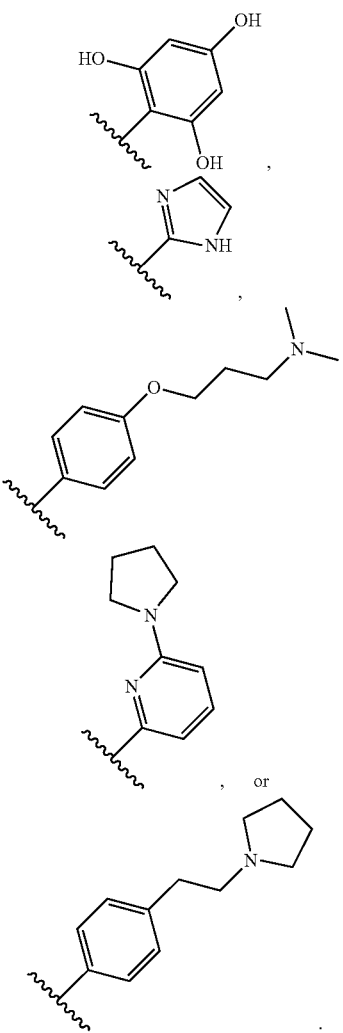

2. The compound of claim 1, wherein $R^1$ is

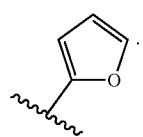 [SMILES: *c1ccco1]

3. The compound of claim 1, wherein $R^2$ is Br.
4. The compound of claim 1, wherein $R^2$ is
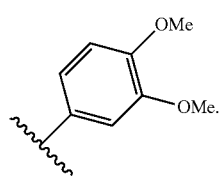 [SMILES: *c1ccc(OC)c(OC)c1]
5. The compound of claim 1, wherein $L^1$ is
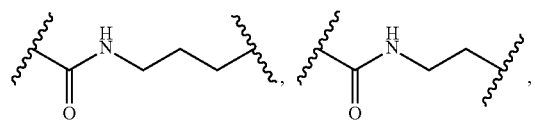
6. The compound of claim 5, wherein $L^1$-A is
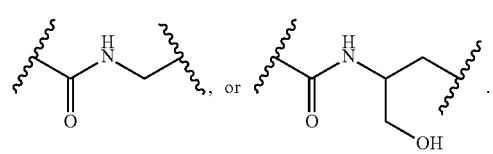
7. The compound of claim 1, wherein $L^1$ is
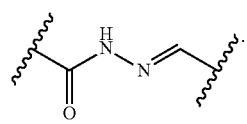 [SMILES: */C=N/NC(*)=O]
8. The compound of claim 7, wherein $L^1$-A is
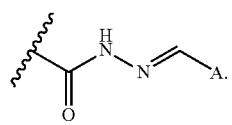
9. A compound selected from
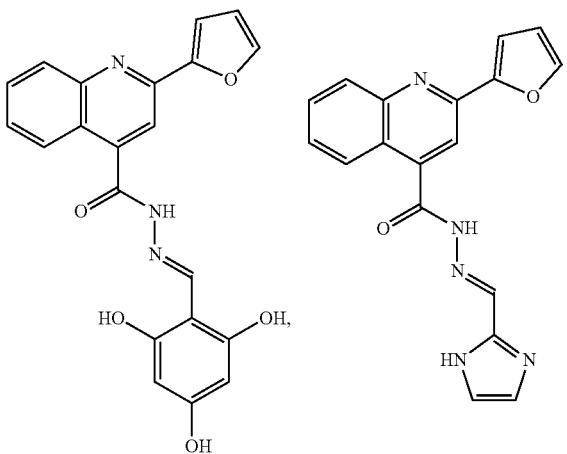
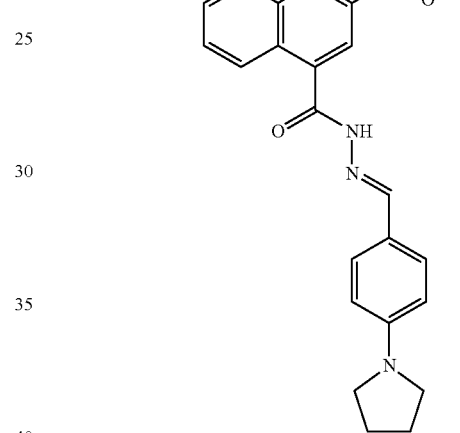
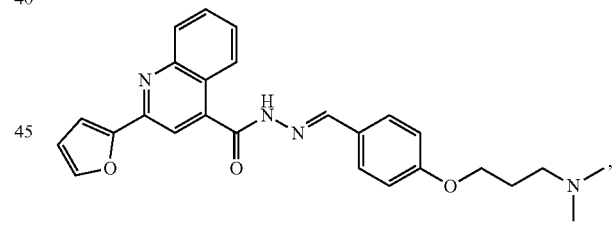
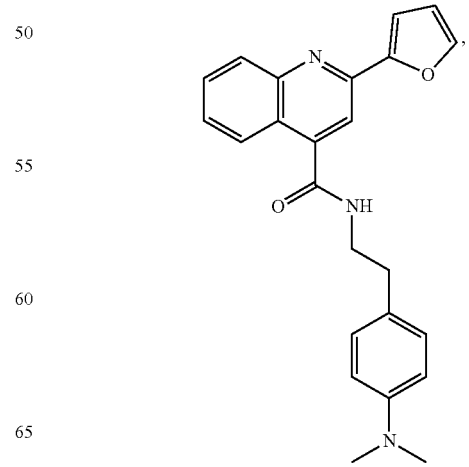

105
-continued
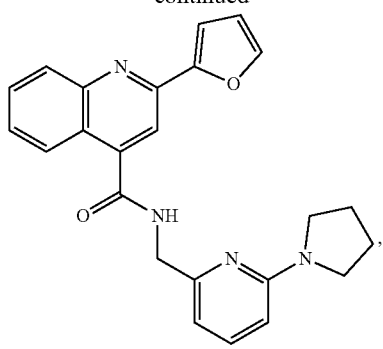
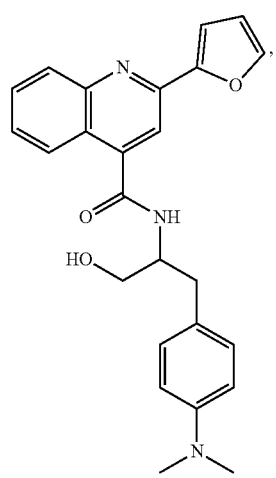
106
-continued
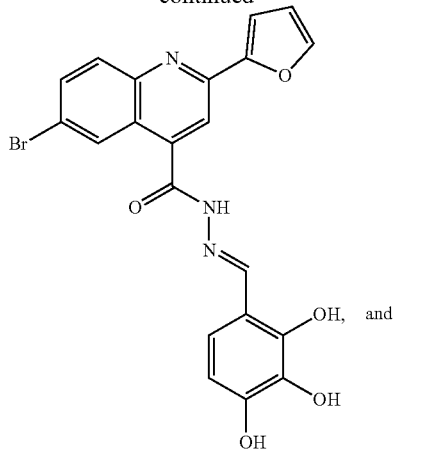
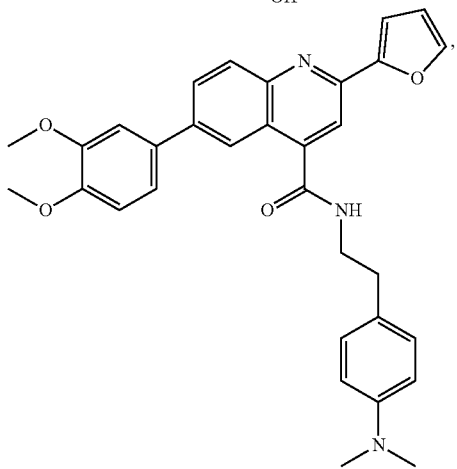
or a pharmaceutically acceptable salt thereof.
10. A pharmaceutical composition comprising a compound of claim 1 and a pharmaceutically acceptable carrier.
* * * * *